US010324920B2

(12) United States Patent
Malcolm

(10) Patent No.: US 10,324,920 B2
(45) Date of Patent: Jun. 18, 2019

(54) RESIDENTIAL MANAGEMENT SYSTEM

(71) Applicant: Douglass Malcolm, Collaroy (AU)

(72) Inventor: Douglass Malcolm, Collaroy (AU)

( * ) Notice: Subject to any disclaimer, the term of this patent is extended or adjusted under 35 U.S.C. 154(b) by 438 days.

(21) Appl. No.: 14/905,720

(22) PCT Filed: Jul. 16, 2014

(86) PCT No.: PCT/AU2014/000729
§ 371 (c)(1),
(2) Date: Jan. 15, 2016

(87) PCT Pub. No.: WO2015/006810
PCT Pub. Date: Jan. 22, 2015

(65) Prior Publication Data
US 2016/0188648 A1    Jun. 30, 2016

(30) Foreign Application Priority Data

Jul. 17, 2013    (AU) .............................. 2013902662

(51) Int. Cl.
| | | |
|---|---|---|
| G06F 17/30 | (2006.01) | |
| G06F 16/22 | (2019.01) | |
| G16H 10/60 | (2018.01) | |
| G06F 19/00 | (2018.01) | |

(52) U.S. Cl.
CPC .......... *G06F 16/2291* (2019.01); *G06F 19/00* (2013.01); *G16H 10/60* (2018.01); *G06F 19/3456* (2013.01); *G06F 19/3475* (2013.01); *G06F 19/3481* (2013.01); *Y02A 90/26* (2018.01)

(58) Field of Classification Search
None
See application file for complete search history.

(56) References Cited

U.S. PATENT DOCUMENTS

| | | | |
|---|---|---|---|
| 9,076,152 B2 * | 7/2015 | Khosravy | G06Q 30/02 |
| 9,135,770 B2 * | 9/2015 | Alberth, Jr. | G07F 15/10 |
| 9,419,735 B2 * | 8/2016 | McCrea | G06F 19/3418 |
| 2007/0112939 A1 | 5/2007 | Wilson et al. | |
| 2010/0205471 A1 | 8/2010 | Vavilala et al. | |
| 2010/0218108 A1 * | 8/2010 | Crabtree | G06Q 50/06 |
| | | | 715/738 |
| 2010/0332373 A1 * | 12/2010 | Crabtree | G06Q 40/04 |
| | | | 705/37 |
| 2012/0260194 A1 | 10/2012 | Kennedy et al. | |

(Continued)

OTHER PUBLICATIONS

"International Search Report and Written Opinion of the International Searching Authority", issued in corresponding International Application No. PCT/AU2014/000729 dated Aug. 18, 2014.

*Primary Examiner* — Hung D Le
(74) *Attorney, Agent, or Firm* — Kaplan Breyer Schwarz, LLP

(57) ABSTRACT

This disclosure relates to a residential management system (200) comprising: a system management module (255), the system management module (255) operably coupled with at least one module (310), and wherein, in use, the system management module (255) is adapted for: sending, to the least one module (310), operational instruction data; receiving, from the at least one module (310), operational data; and generating module reporting data at least in accordance with the operational data.

20 Claims, 17 Drawing Sheets

(56) References Cited

U.S. PATENT DOCUMENTS

| | | | |
|---|---|---|---|
| 2013/0103622 A1* | 4/2013 | Matsuoka | H04L 12/2825 |
| | | | 706/12 |
| 2013/0232138 A1* | 9/2013 | Calvert | G06F 16/24569 |
| | | | 707/722 |
| 2014/0101082 A1* | 4/2014 | Matsuoka | H04L 12/2829 |
| | | | 706/12 |
| 2015/0286731 A1* | 10/2015 | Khosravy | G06Q 30/02 |
| | | | 707/722 |
| 2015/0379533 A1* | 12/2015 | Alberth | G07F 15/10 |
| | | | 705/7.31 |
| 2017/0070362 A1* | 3/2017 | Tappeiner | G05B 11/01 |
| 2017/0158327 A1* | 6/2017 | Willford | B64C 25/34 |

* cited by examiner

RESIDENTIAL MANAGEMENT SYSTEM

FIELD OF THE INVENTION

The present invention relates to a residential management system.

The invention has been developed primarily for use in residences and will be described hereinafter with reference to this application. However, it will be appreciated that the invention is not limited, to this particular field of use.

BACKGROUND

According to existing arrangements, residential management systems provide certain home automation abilities such as dimming lights, controlling air-conditioning and the like. However, such existing arrangements do not cater for more advanced functionality demanded by today's modern lifestyle.

It is to be understood that, if any prior art information is referred to herein; such reference does not constitute an admission that the information forms part of the common general knowledge in the art, in Australia or any other country.

SUMMARY

The invention seeks to provide a residential management system which will overcome or substantially ameliorate at least some of the deficiencies of the prior art, or to at least provide an alternative.

According to one aspect, there is provided a residential management system comprising a system management module, the system management module operably coupled with at least one module, and wherein, in use, the system management module is adapted for sending, to the least one module, operational instruction data; receiving, from the at least one module, operational data; and generating module reporting data at least in accordance with the operational data.

Preferably, the system management module is adapted for configuration using a configuration file configured in accordance with a residence.

Preferably, the system management module is adapted for implementing authenticated access control.

Preferably, the authenticated access control is adapted for authenticating a plurality of users.

Preferably, comprising a network interface operably coupled to the Internet, and wherein at least one of the system management module and the at least one module is adapted for sending and receiving data, via the network interface, to a web service.

Preferably, the web service comprises at least one of environmental, public health department, product filament, resource provider and telecommunications provider web services.

Preferably, the at least one module comprises a resource management module.

Preferably, the resource management module comprises at least one of an electrical power management module, water management module and a gas management module.

Preferably, the resource management module is operably coupled to at least one household appliance supply so as to be adapted for measuring the consumption of the at least one household appliance.

Preferably, the resource management module further comprises at least one of usage log and costing and premium usage planning functionality.

Preferably, the resource management module is adapted for receiving, via the network interface, power rate schedule data.

Preferably, the resource management module is adapted for detecting leakages in accordance with a discrepancy between a supply and consumption of a resource.

Preferably, the electrical power management module is adapted to monitor the supply and consumption of electrical power.

Preferably, the electrical power management module is adapted for selecting a source of electrical power.

Preferably, the power management module is adapted for selecting the source at electrical power in accordance with the power source available and the level of power available within the battery bank or direct source from Alternate Power Source.

Preferably, the water management module is adapted for monitoring the consumption and supply of water.

Preferably, the water management module is adapted for monitoring the supply levels of residential water storage facilities.

Preferably, the water management module is adapted for selecting a water source.

Preferably, the water management module is adapted for assisting in the selection of a hot water source in accordance with the Solar Hot Water Temperature Watch (3.6.6) data.

Preferably, the hot water source comprises at least one of electrical heating tank and gas heating tank water sources.

Preferably, the water management module is adapted for identifying water leakage.

Preferably, the gas management module is adapted for monitoring the consumption of gas.

Preferably, the gas management module is adapted for selecting a gas supply.

Preferably, the gas management module is adapted for monitoring a supply level of a tank gas supply.

Preferably, the gas supply comprises at least one of mains gas supply and tank gas supply.

Preferably, the at least one module comprises a contacts and diaries module adapted for recording contacts and associated data and schedule data for at least one user.

Preferably, the contacts and diaries module is operably coupled to the telecommunications network interface so as to be adapted for providing caller identification.

Preferably, the contacts and diaries module is adapted for calculating activity duration data representing the duration of at least one activity in accordance with the scheduled data and generating an alert if the activity duration data exceeds a recommended threshold.

Preferably, the at least one module comprises a telecommunications management module Preferably, the telecommunications management module is adapted for recording telecommunications usage information.

Preferably, the telecommunications management module is operably coupled, via the network interface, to a telecommunications web service.

Preferably, the telecommunications management module is adapted for receiving, via the network interface, from the telecommunications web service telecommunications usage data.

Preferably, the telecommunications management module is adapted for receiving, via the network interface, from the telecommunications web service telecommunications cost data.

Preferably, the at least one module comprises a Internet access management module.

Preferably, the Internet access management module is operably coupled, via the network interface, to an Internet service provider web service.

Preferably, the Internet access management module is adapted for receiving, via the network interface, from the Internet service provider web service Internet usage data.

Preferably, the telecommunications management module is adapted for receiving, via the network interface, from the Internet service provider web service, Internet service cost data.

Preferably, the at least one module comprises a healthcare module adapted for recording healthcare data in relation to at least one user.

Preferably, the healthcare management module is operably coupled, via the network interface, to a health provider practice management system web service.

Preferably, the healthcare management module is adapted for sending, to the health provider practice management system web service, healthcare data comprising at least one of medical record, medical appointment schedule and medical condition healthcare data.

Preferably, the healthcare data comprises symptom data and wherein the healthcare management module is adapted and the healthcare provider may provide diagnosis data in accordance with the symptom data.

Preferably, the healthcare data comprises a prescription regime and wherein the healthcare management module is adapted for generating reminders in accordance with the prescription regime.

Preferably, the at least one module comprises a household inventory and ordering module.

Preferably, the household inventory and ordering the module is adapted for recording inventory data relating to at least one inventory of a household.

Preferably, a household inventory and ordering module is adapted for receiving supply and consumption data relating to the supply or consumption of the at least one inventory and updating the inventory data in accordance with the supply and consumption data.

Preferably, the household inventory and ordering module is operably coupled, via the network interface, to an order fulfillment web service and wherein the inventory and ordering module is adapted to send, to the order fulfillment web service order the representing an order for a least one product.

Preferably, the household inventory comprises grocery inventory, and wherein the household inventory and ordering module is adapted for maintaining it grocery inventory in accordance with a dietary regime.

Other aspects of the invention are also disclosed.

BRIEF DESCRIPTION OF THE DRAWINGS

Notwithstanding any other forms which may kill within the scope of the present invention, preferred embodiments of the invention will now be described, by way of example only, with reference to the accompanying drawings in which:

FIG. 15 shows a schematic of the household ordering and inventory module in accordance with an embodiment of the present invention;

FIG. 16 shows a schematic of the MOBILE APPLICATION as Stand-Alone Product ran on a hand-held peripheral device module in accordance with an embodiment of the present invention.

DESCRIPTION OF EMBODIMENTS

Figure 1:
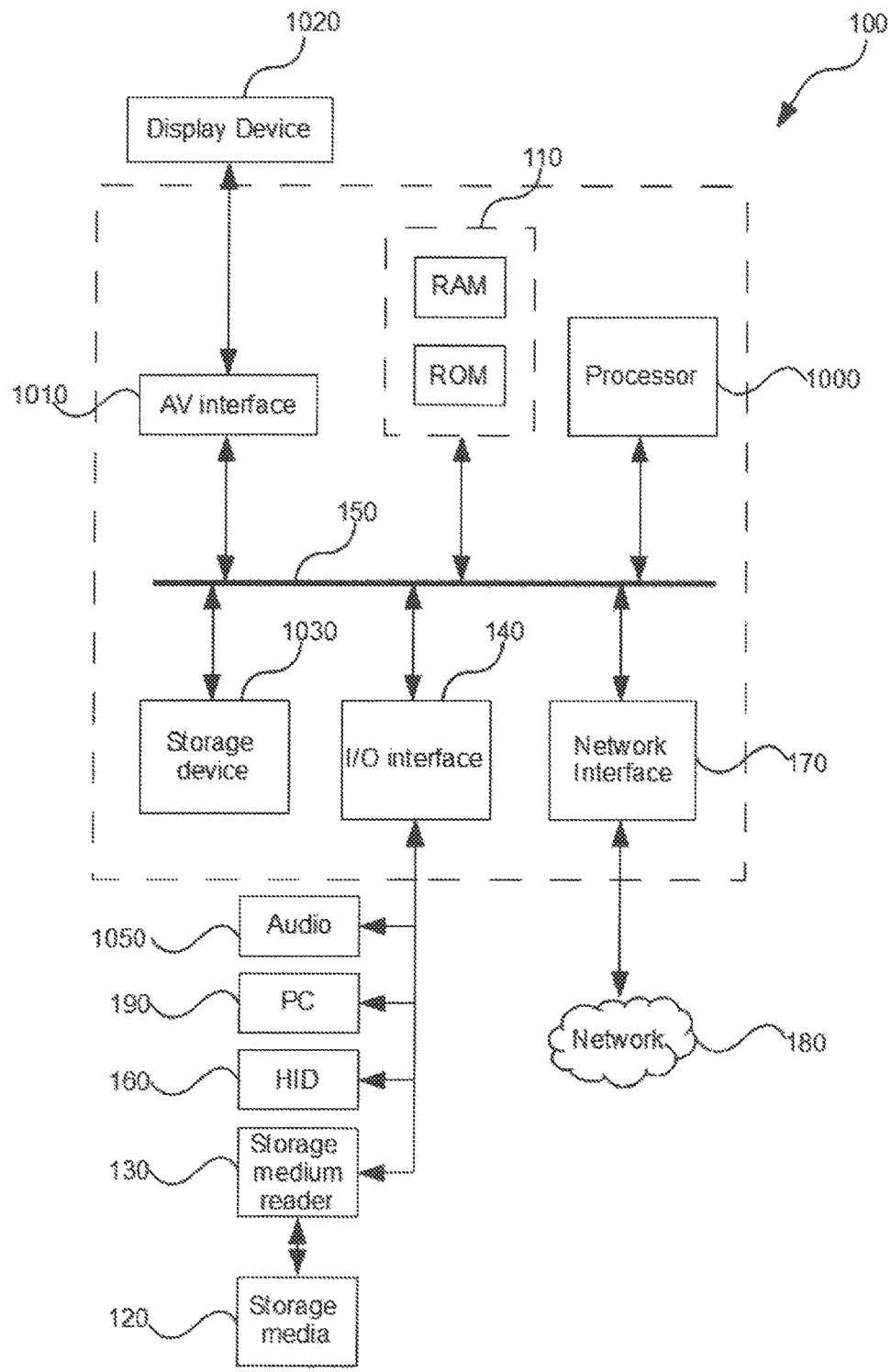
FIG. 1 shows a computing device on which the various embodiments described herein may be implemented in accordance with an embodiment of the present invention.

It should be noted in the following description that like or the same reference numerals in different embodiments denote the same or similar features.

Computing Device 100

FIG. 1 shows a computing device 100 on which the various residential management modules described herein may be implemented. The computing device 100 may take on differing embodiments depending on the application, including, as an embedded controller for remote deployment within, various areas of a residence, server computing device adapted for serving various computing devices 100 across the network 180 (as described below), stand-alone computing device for use by a resident, mobile computing device (such as a mobile telecommunication device, mobile tablet computing device or the like) coupled to the network 180.

In particular the steps of residential management may be implemented as computer program code instructions executable by the computing device 100. The computer program code instructions may be divided into one or more computer program code instruction libraries, such as dynamic link libraries (DLL), wherein each of the libraries performs a one or more steps of the method. Additionally, a subset of the one or more of the libraries may perform graphical user interface tasks relating to the steps of the method.

The device 100 comprises semiconductor memory 110 comprising volatile memory such as random access memory (RAM) or read only memory (ROM). The memory 100 may comprise either RAM or ROM or a combination of RAM and ROM.

The device 100 comprises a computer program code storage medium reader 130 for reading the computer program code instructions from computer program code storage media 120. The storage media 120 may be optical media such as CD-ROM disks, magnetic media such as floppy disks and tape cassettes or flash media such as USB memory sticks.

The device further comprises I/O interface 140 for communicating with one or more peripheral devices. The I/O interface 140 may offer both serial and parallel interface connectivity. For example, the I/O interface 140 may comprise a Small Computer System Interface (SCSI), Universal Serial Bus (USB) or similar I/O interface for interfacing with the storage medium reader 130. The I/O interface 140 may also communicate with one or more human input devices (HID) 160 such as keyboards, pointing devices, joysticks and the like. The I/O interface 140 may also comprise a computer to computer interface, such as a Recommended Standard 232 (RS-232) interface, for interfacing the device 100 with one Or more personal computer (PC) devices 190. The I/O interface 140 may also comprise an audio interface for communicate audio signals to one or more audio devices 1050, such as a speaker or a buzzer.

The device 100 also comprises a network interface 170 for communicating with one or more computer networks 180. The network 180 may be a wired network, such as a wired Ethernet™ network or a wireless network, such as a Bluetooth™ network or IEEE 802.11 network. The network 180 may be a local area network (LAN), such as a home or office computer network, or a wide area network (WAN), such as the Internet or private WAN.

The device 100 comprises an arithmetic logic unit or processor 1000 for performing the computer program code instructions. The processor 1000 may be a reduced instruction set computer (RISC) or complex instruction set computer (CISC) processor or the like. The device 100 further comprises a storage device 1030, such as a magnetic disk hard drive or as solid state disk drive.

Computer program code instructions may be loaded into the storage device 1030 from the storage media 120 using the storage medium reader 130 or from the network 180 using network interface 170. During the bootstrap phase, an operating system and one or more software applications are loaded from the storage device 1030 into the memory 110. During the fetch-decode-execute cycle, the processor 1000 fetches computer program code instructions from memory 110, decodes the instructions into machine code, executes the instructions and stores one or more intermediate results in memory 100.

In this manner, the instructions stored in the memory 110, when received and executed by the processor 1000, may configure the computing device 100 as a special-purpose machine that may perform the functions described herein.

The device 100 also comprises a video interface 1010 for conveying video signals to a display device 1020, such as a liquid crystal display (LCD), cathode-ray tube (CRT) or similar display device.

The device 100 also comprises a communication bus module 150 for interconnecting the various devices described above. The bus module 150 may offer parallel connectivity such as Industry Standard Architecture (ISA), conventional Peripheral Component Interconnect (PCI) and the like or serial connectivity such as PCI Express (PCIe), Serial Advanced Technology Attachment (Serial ATA) and the like.

Residential Management System 200

Figure 2:
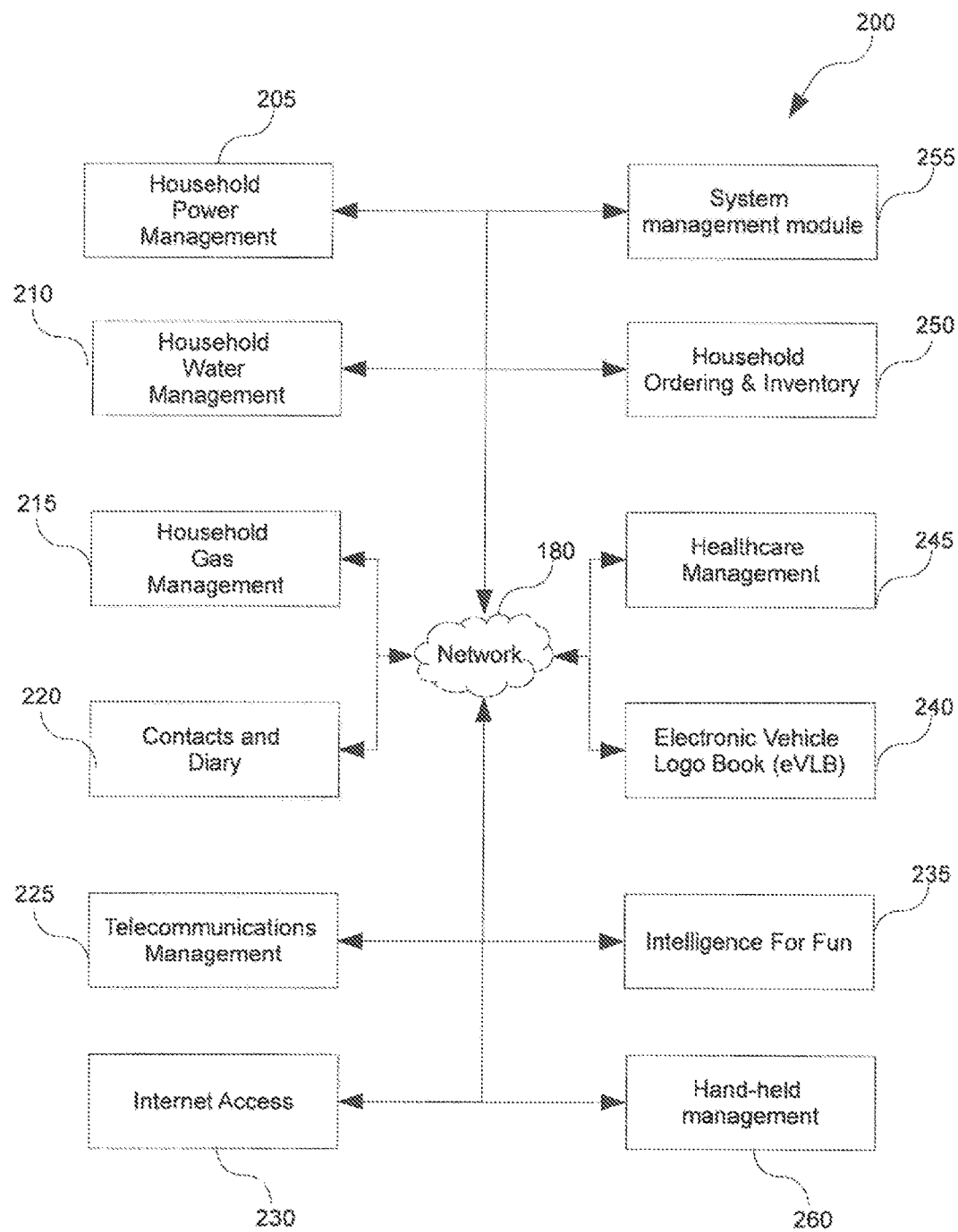
FIG. 2 shows a residential management system in accordance with an embodiment of the present invention.

Turning now to FIG. 2, there is shown a residential management system 200 for managing the various aspects of a residence some of which are described in further detail below. It should be noted that the description herein of the residential management system 200 should be cross-referenced with Appendix A comprising further technical detail in relation to the residential management system 200.

In general, the system 200 is adapted for assisting residents in various aspects, including functional management; resource management; budgetary management in both savings to be made from more prudent consumption and also planning and the final, personal health management and the like.

The system 200 comprises a number of modules (labelled 205 to 260 in FIG. 2) with reference to their purpose. It should be noted that the term "module" as used herein should not be construed in a technical limiting manner and should rather be construed as a technical implementation adapted for the purpose for which the module is designed. Therefore, a module, as described herein, may be implemented purely as software (whether firmly or software), as hardware (such as a computing device 100 or the like) or a combination of both. Furthermore, modules need not necessarily be discreet as represented in FIG. 2, and various functionality described herein may be shared or distributed amongst modules.

The modules are adapted to communicate with each other, including, via the network 180 and directly. Various communication protocols may be employed, such as Ethernet, current loop, Insteon™, Wi-Fi, X-10™, ZigBee™, Z-Wave™ and the like.

System Management Module 255

The system 200 comprises system management module 255 adapted for managing the various aspects of the system 200. The system management module 255 may comprise a stand-alone computing, device 100 provided with sufficient processing and storage ability to manage the various modules described herein. The system management module 255 may be located within the residence (such as within a secure location) or at a remote location and accessed via web services as the case may be.

Figure 3A:
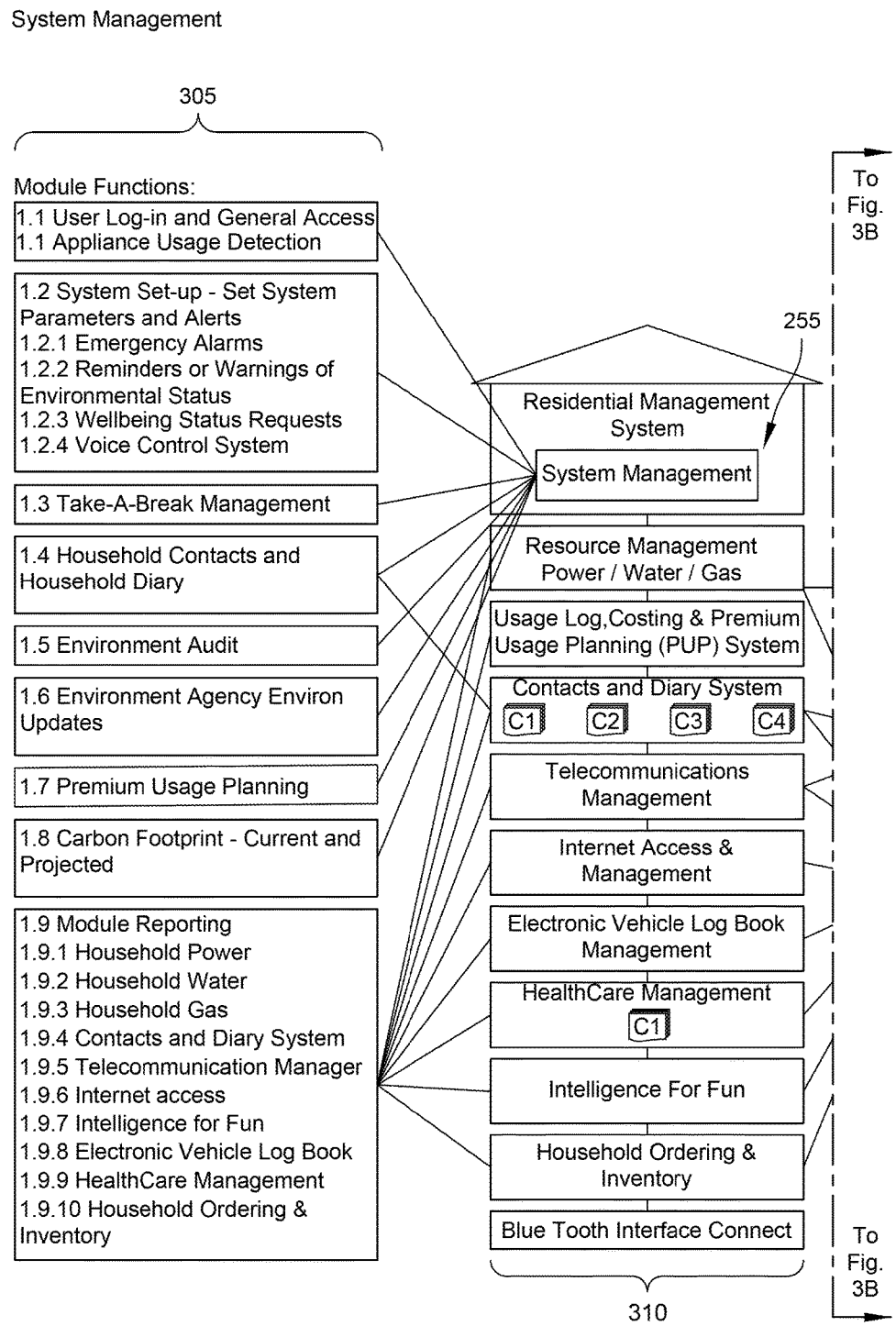
FIGS. 3A and 3B show a schematic of the system management module in accordance with an embodiment of the present invention.
Figure 3B:
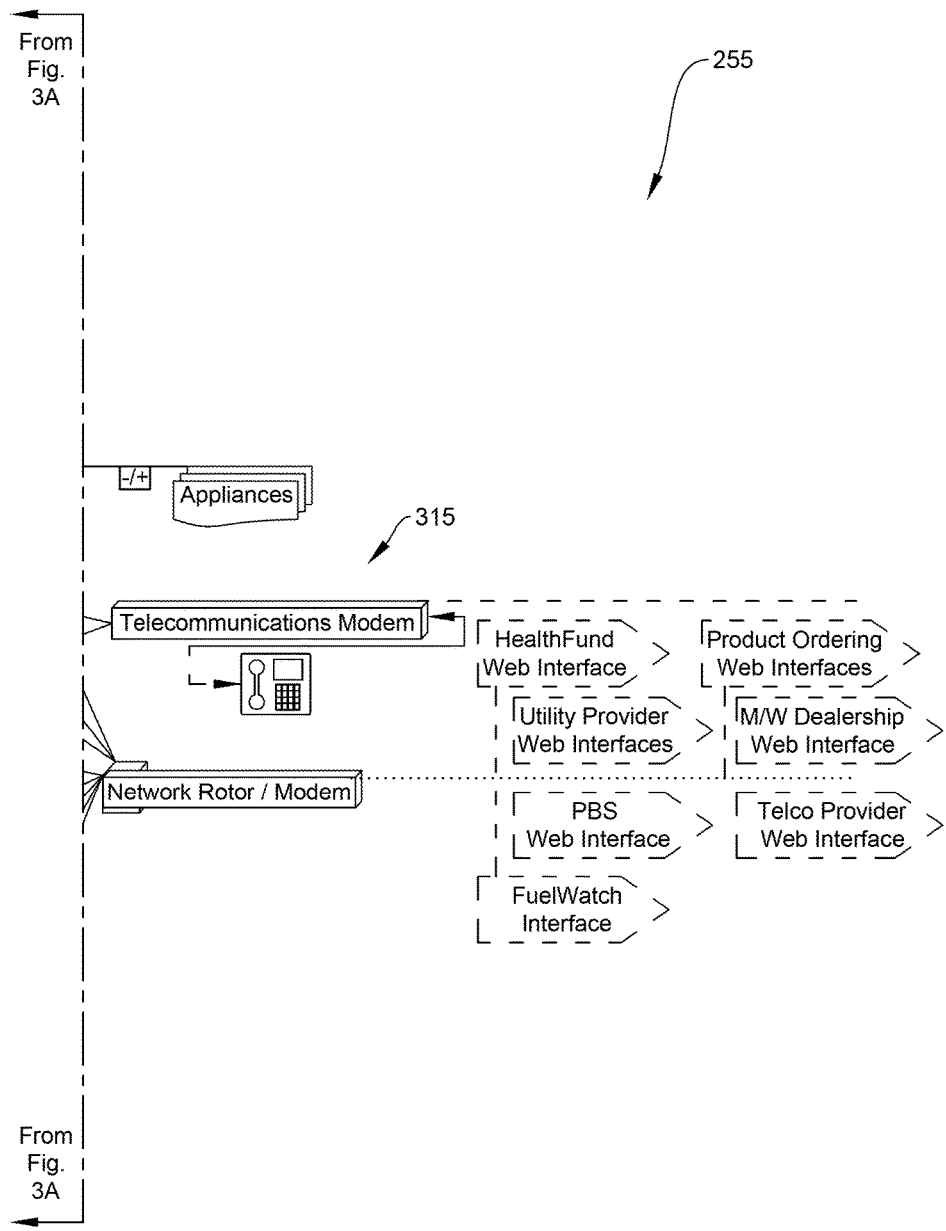

Referring to FIGS. 3A and 3B, there is shown the residential management system schematic 300 in further detail and wherein the interface between the system management module 255 and the other components of the residential management system schematic 300 are apparent. Specifically, the system management module 255 is operably coupled with at least one module 310 such that the system management module 255 is adapted for sending, to the least one module 310, operational instruction data; receiving, from the at least one module, operational data; and generating module reporting data at least in accordance with the operational data.

As is apparent from the residential management schematic 300, the system management module 255 is adapted for providing module functionality as indicated by items 305 with the schematic 300. The module functionality generally comprises operational functionality in the control of the modules 310 and also for the reporting of the operation of the modules 310. In a preferred embodiment, the system management module 255 comprises a touchscreen display device 1020 adapted for displaying operational and reporting data relating to the modules 310 and receiving operational instructions therefore.

The reporting functionality provided by the system management module 255 may differ depending on the application, but such reporting functionality is generally adapted for providing reporting of the operation of the at least one module 310 as described in further detail below.

The system management module 205 may be configured in accordance with a configuration file for differing residences. As such, the configuration file is adapted for allowing the configuration of the residential management system 300 in accordance with the particular requirements of a particular residence. The configuration file may be adapted for configuring the residential management system 300 for a variety of configurations but may include the configuration of system parameters and alerts, emergency alarms (such as security alarms and smoke detection) the configuration of reminders or warnings of environment or status (some of which may be configured for requiring action by the user), voice control customization and the like.

Also, the system management module 255 is adapted for implementing authenticated access control which access control may be adapted for single user access authentication or multi-user authentication access control.

Further, the residential management system comprises a network interface 315 operably coupled to the Internet and adapted for allowing the system management module for the at least one module 310 to communicate with web services across the Internet. Various of these web services will be described in further detail below but, for example, the well services may comprise environmental, health fund, product filament, resource provider, telecommunications provider web services and the like.

It should be noted that while in the preferred embodiment as shown in schematic 300, the residential management system 300 comprises a system management module 255 acting as the master for each of the slave module 310, in other embodiments a decentralised nonhierarchical topology may be employed wherein each module 310 interfaces with each other module 310 depending on the particular requirements of the module 310.

Household Resource Management Module 205, 210, 215

As is apparent from the schematics, the residential management system 300 further comprises a household resource management modules 205, 210, 215. The household resource management modules comprise modules including an electrical power management module 205, water management module 210 and a gas management module 215, adapted for monitoring electrical generation and consumption, water collection and consumption and gas consumption. It should be noted that the household resource management modules need not necessarily be employed for the purposes of measuring consumption only, but may also be adapted for monitoring supply, such as where a residential hostel comprises solar panels and supplies electrical energy back to the grid.

The household resource management modules are operably coupled to at least one household appliance supply so as to be adapted for measuring the consumption of at least one household appliance. For example, the residential management system may comprise of number of consumption meters, such as water flow rate meters, gas flow rate meters and electrical power consumption meters operably coupled to the household resource management module for the purposes of reporting on consumption and supply.

The household resource management modules may further comprise log functionality to log power consumption and supply fir later analysis or for forwarding via the network interface 315 usage and supply information to a resource provider web service.

Furthermore, the household resource management modules may comprise premium usage planning module adapted fir determining applicable consumption and supply rates in accordance with a schedule so as to be able to either automate the timing of consumption and supply or at least advising thereon. For example, the premium usage planning module may be adapted for automating the disconnection of non-critical appliances (such as hot water tanks) and during peak periods or for supplying power to a grid (such as from storage such as batteries) during peak periods.

It should be noted that the system management module 255 may be adapted to retrieve operational data from the household resource management module so as to report on household power, water, gas usage supply and cost and for the calculation of a carbon footprint.

Household Power Management Module 205

Figure 4:
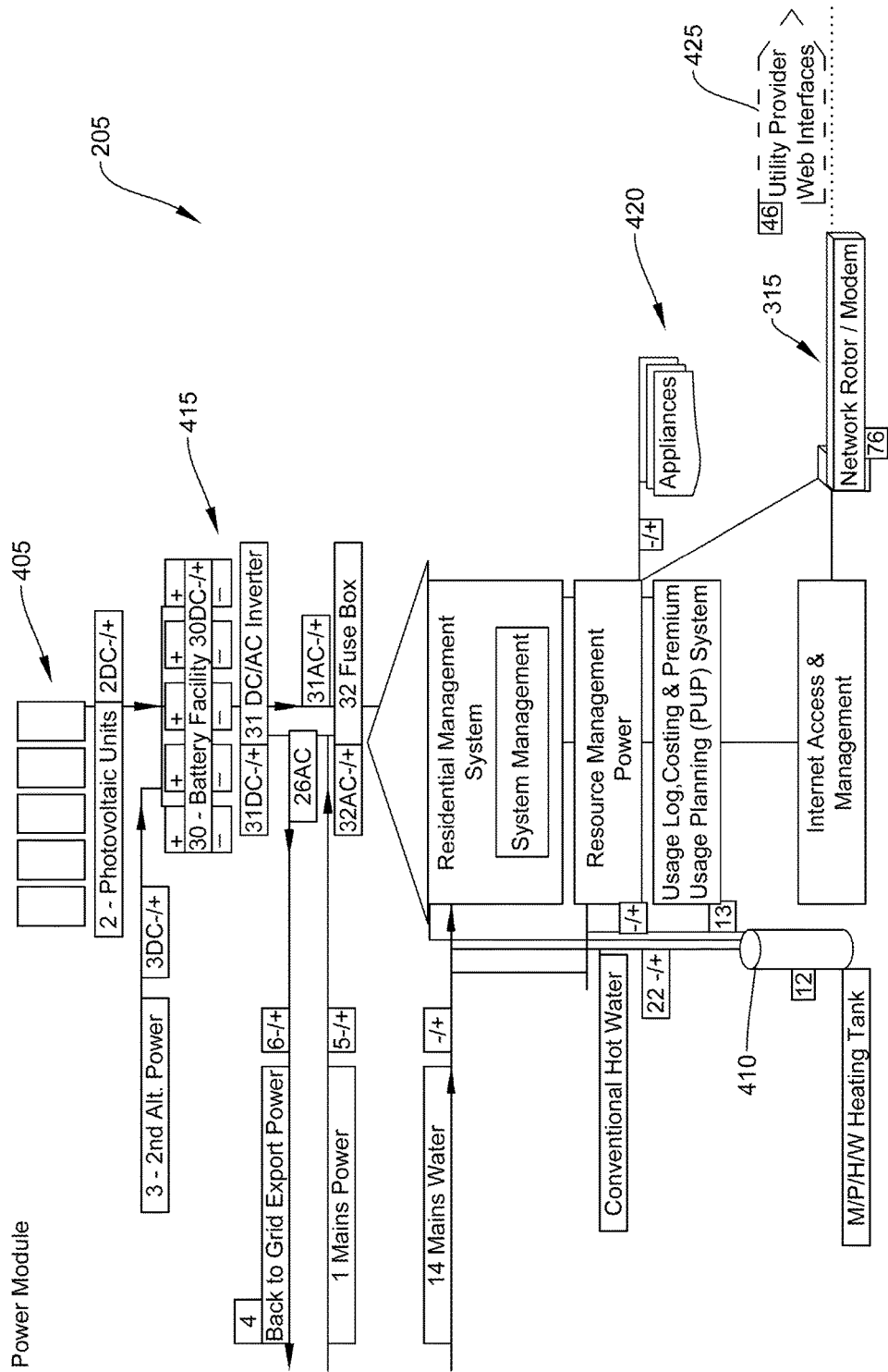
FIG. 4 shows a schematic of the power module in accordance with an embodiment of the present invention.

Referring now to FIG. 4, there is shown an exemplary household power management module 205 adapted for managing the electrical power management requirements of a residence and the reporting thereon. As is apparent from the schematic 400, the power management module 205 is adapted for interfacing with a variety of electrical apparatus and appliances within a residence, including photovoltaic units 405, heating tanks 410, battery storage 450, household appliances 420 and the like.

Also, the power management module 205 is adapted to send and receive information via the network interface 315 to a resource provider web service, for a variety of purposes, including for the reporting of consumption and supply, the retrieval of premium usage information (including applicable rates in accordance with a time schedule) and the like.

It should be noted that the residential management system may be configured to control the power management of the residents using the power management module 205 so as to, for example in an automated manner, controlled the connection and disconnection of various critical and non critical appliances, determine the timing of supply and consumption in accordance with the premium usage schedule and the like. Alternatively, the residential management system 200 may be configured in an advisory manner wherein rather than automating the control of the power of the residence, the user is a advised accordingly, such as by being advised to turn off certain appliances.

Water Management Module 210

Figure 5A:
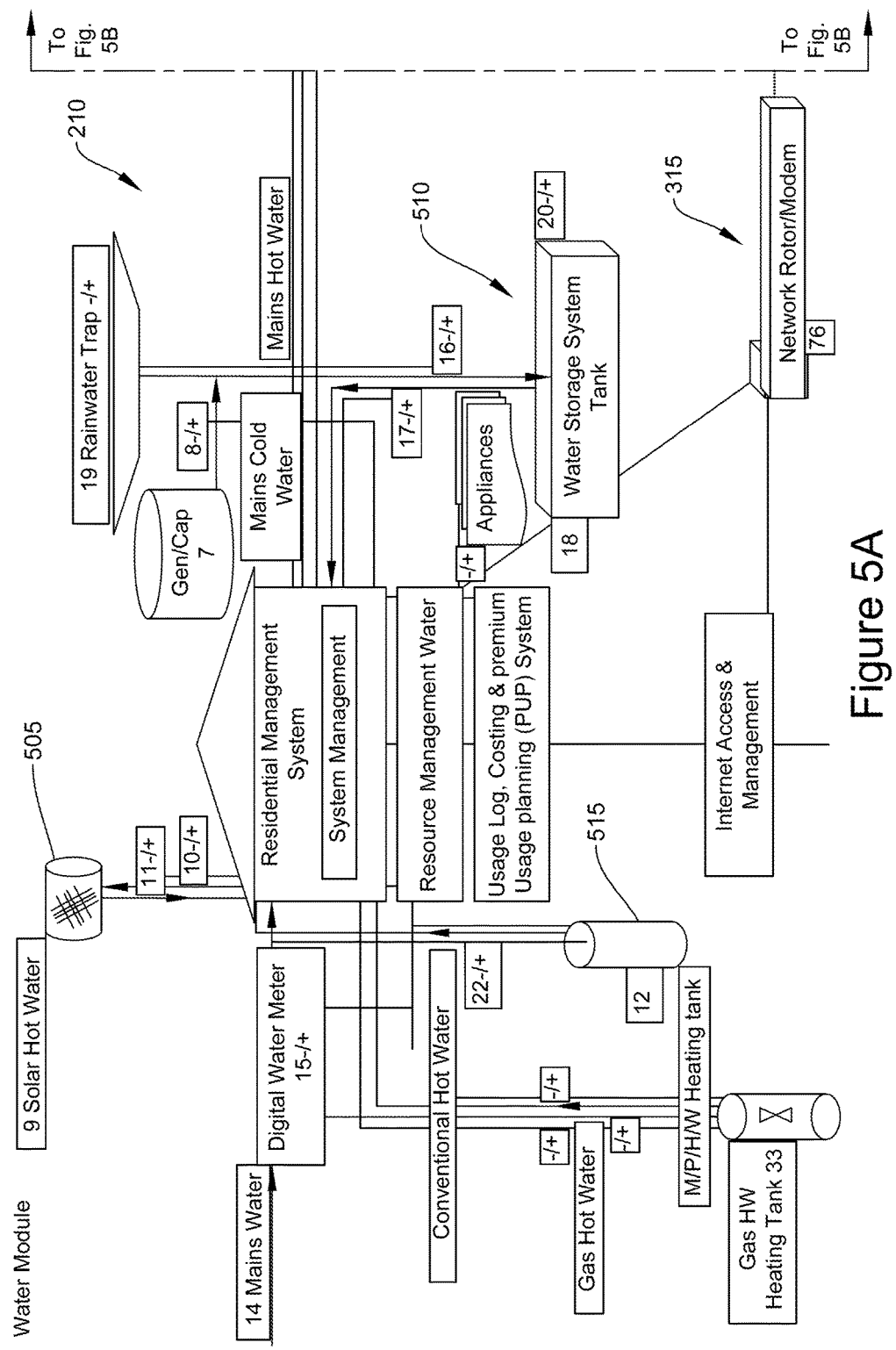
FIGS. 5A and 5B show a schematic of the water module in accordance with an embodiment of the present invention.
Figure 5B:
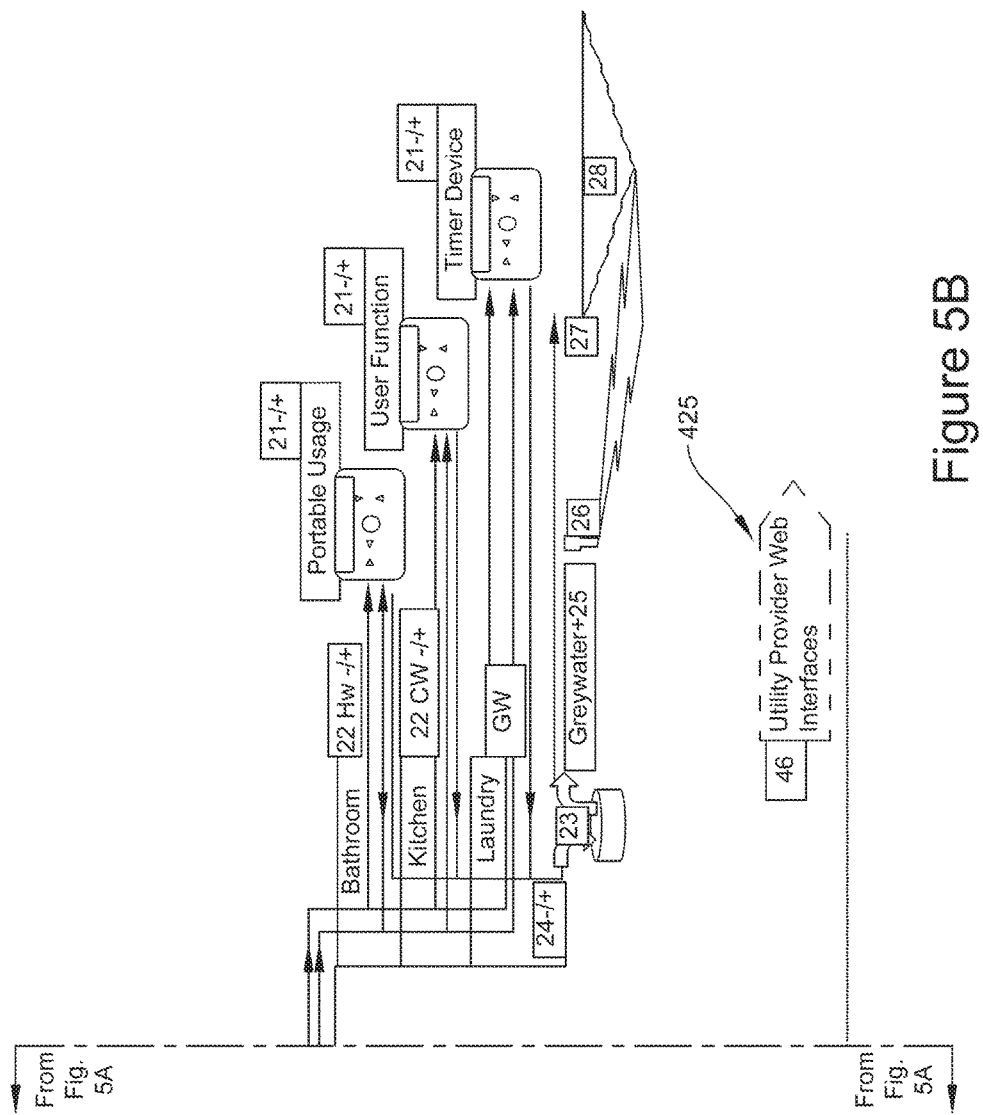

Turning now to FIGS. 5A and 5B, there is shown a schematic of the water management module 210 in further detail. As is apparent, the water management module 210 is adapted for monitoring the supply and consumption of water within the residence, including the supply state (i.e. level) of various water storage facilities, including rainwater storage system 510. Furthermore, the water management module 500 may be adapted for selecting the supply of water in accordance with instructional information from the power management module 400. For example, depending on the power requirements of the residence as determined by the power management module 400, the water management module 500 may select hot water supply from the heating tank 515 or the solar heating tank 505 as the case may be. Furthermore, the water management module 500 may further control the supply of waste (grey) water, including whether the wastewater is returned to the municipal drain system or rather routed to the garden, for example.

Furthermore, the water management module 500 may further interface with the gas management module 600 (as will be described further below) for the purposes of selecting the most appropriate means for heating water, whether it be by electricity, or gas.

Gas Management Module 215

Figure 6:
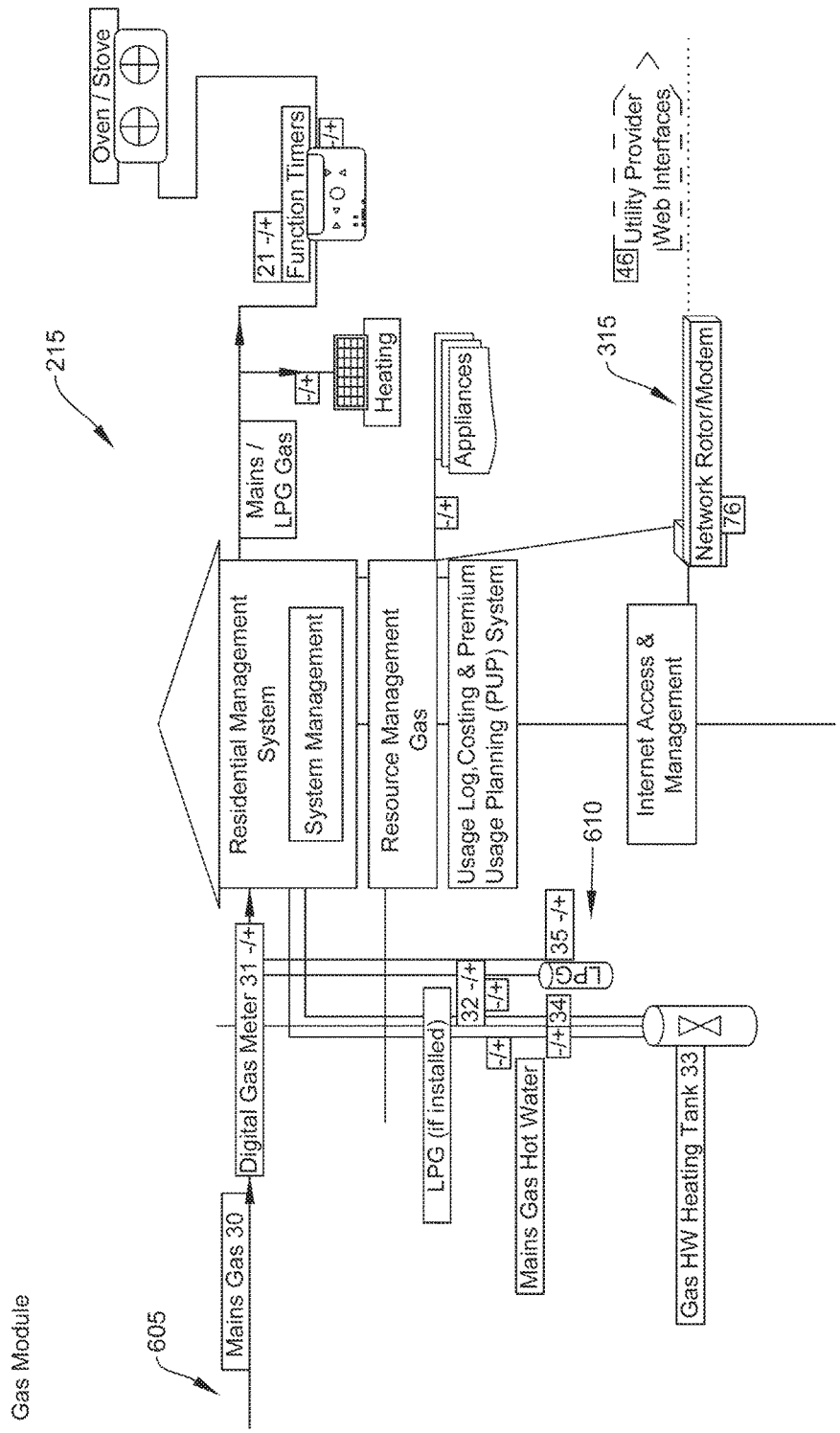
FIG. 6 shows a schematic of the gas module in accordance with an embodiment of the present invention.

Turning now to FIG. 6, there is shown a schematic of the gas management module 215 showing the functionality of the gas management module 215 in further detail. The gas management module 215 is adapted for monitoring the consumption of gas within a residence. Furthermore, the gas management module 215 is adapted for selecting a gas supply so as to, for example be able to select whether to use mains has 605 or tank gas 610.

In this embodiment, the gas management module 215 is adapted for monitoring a supply level of the gas tank 610 so as to determine the remainder supply of the gas tank so as to be able to switch over to mains gas 610 in order to preserve at least a minimum gas tank supply. At the resupply of the gas tank 610, the user may configure the system management module to reset the gas supply level.

It should be noted that the resource management modules may be adapted for detecting leakages within the residence. For example, by monitoring the water supply and the water consumption, the resource management modules may be adapted to identify a water leak in accordance with a discrepancy between the supply and consumption. Similarly, the resource management module may be adapted for detecting was and power leakages.

Contacts and Diaries Module 220

Referring again to FIG. 2, the residential management system 200 further comprises a contacts and diaries module 220. The contacts and diaries module 220 is adapted for allowing users to keep accurate records of contact information and diary (schedule) information. It should be noted that the contacts and diaries module 220 may be configured for sharing contacts and diaries information for multi-user application.

Figure 7:
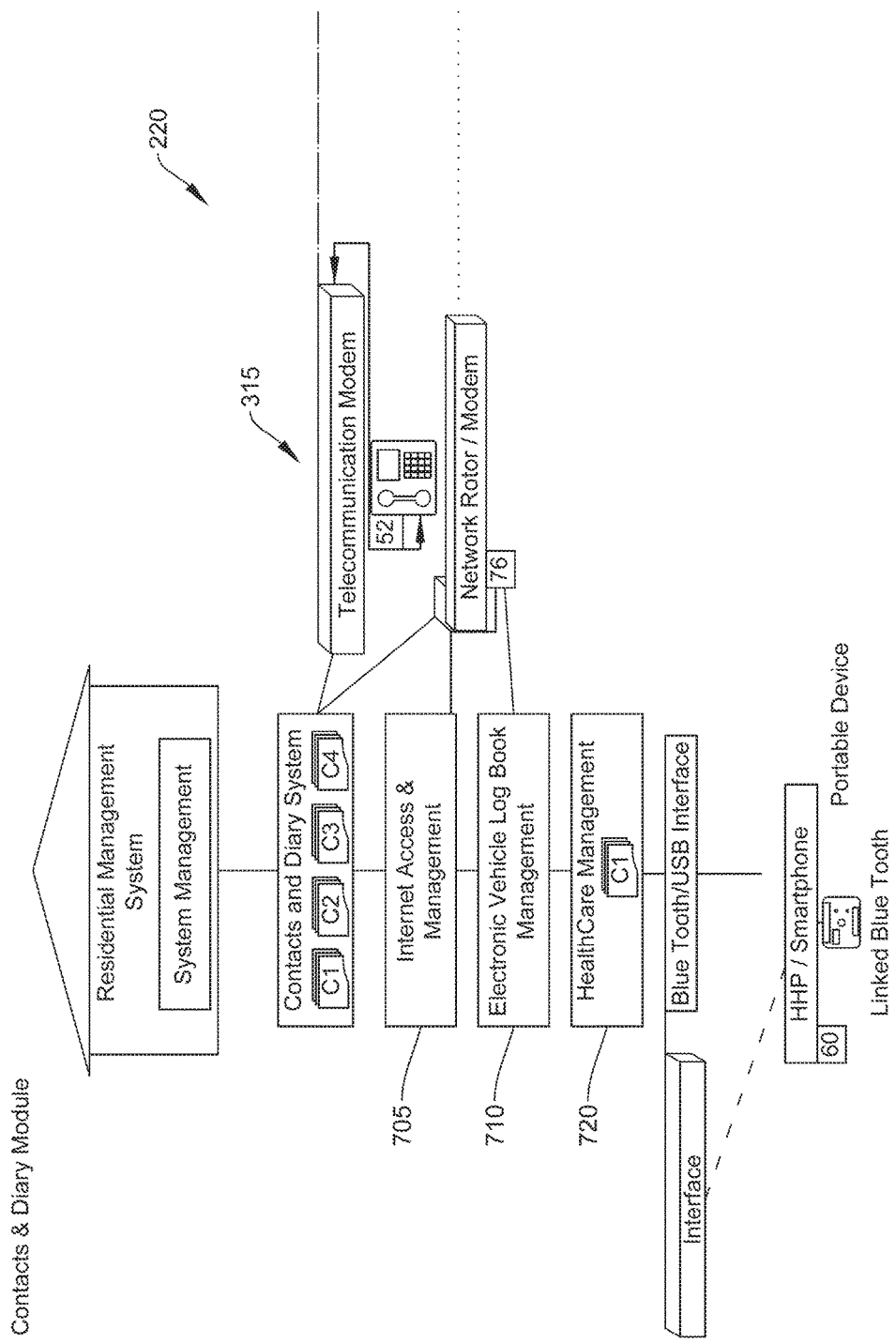
FIG. 7 shows a schematic of the household accounts module in accordance with an embodiment of the present invention.

Turning now to FIG. 7, there is shown the contacts and diaries module 700 in further detail. The contacts and diaries module 700 may be adapted for receiving contact and diary information directly from a user, or alternatively interface with a third-party applications (such as e-mail applications and the like) to receive or Synchronise with contact and diary information.

Furthermore, as is apparent from the figure, the contacts and diaries module 700 may be operably coupled with the network interface 315 so as to be able to provide caller identification for inbound telecommunication calls and the like. Furthermore, the contacts and diaries module 700 may be adapted for automating dialed outbound calls so as to, for example, be able to initiate an outbound telecommunication call upon receipt of a name of a contact from a user.

Furthermore, the contacts and diaries module 700 may be operably coupled with other modules including the electronic vehicle log book management module 710 and healthcare management modules 720 as substantially shown in the schematics 700 for the purposes of scheduling events relating to vehicles and healthcare. For example, the contacts and diaries module 700 may be adapted for reminding a user to take medication in accordance with a treatment regime. Alternatively, the contacts and diaries module 700 may be adapted for scheduling vehicle services and the like.

Household Accounts Management Module 265

Referring again to the residential management system 200, the residential management system 200 further comprises a household accounts management module 265. The accounts management module 265 is adapted for providing users with the ability to keep accurate records of personal and household accounts of both debtors and creditors.

Figure 8:
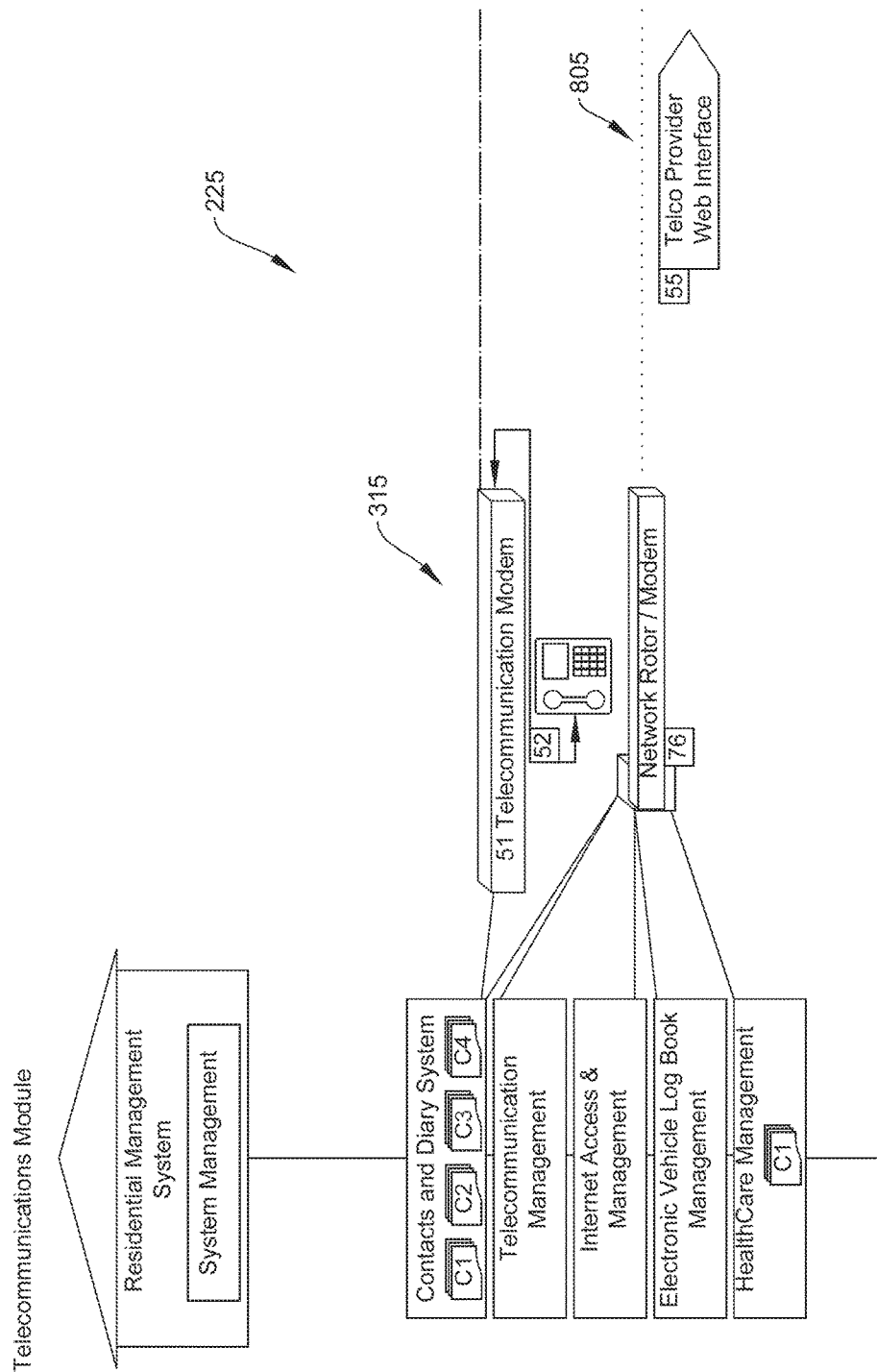
FIG. 8 shows a schematic of the security module in accordance with an embodiment of the present invention.

Referring now to FIG. 8, there is shown a schematic of the accounts management module 265 in further detail.

In one embodiment, the accounts management module 265 is adapted for interfacing with the internet access module 230 for the purposes of obtaining account information from a financial institution web service.

Similarly, the household accounts management module 265 may be adapted for report period transactional statements to be reconciled with financial institutional transactional statements for the same period in order to ensure accuracy.

Security Management Module 270

Referring again to the residential management system 200, the residential management system 200 thither comprises a security management module 270, in one embodiment the to security management module 270 may be adapted through integration with a $3^{rd}$ party residential alarm system, for providing users with the ability to keep accurate records of security alarm activations and deactivations including, those users responsible for these actions.

In another embodiment the security management module 270 may be adapted through integration with a $3^{rd}$ party motor vehicle remote security system, for providing users with the ability to keep accurate records of security alarm activations and deactivations including those users responsible for these actions.

Telecommunications Management Module 225.

Referring again to the residential management system 200, the residential management system 200 thither comprises a telecommunications management module 225. The telecommunications management module 225 is adapted for providing users with the ability to keep accurate records of personal and household telecommunication usage, including phone usage.

Referring now to FIG. 8, there is shown a schematic of the telecommunications management module 225 in thither detail. In one embodiment, the telecommunications management module 225 is adapted for interfacing with the network interface 315 (which may comprise a number of telecommunications interfaces such as phone, fax, sms, Internet and the like network interfaces) for the purposes of recording telecommunications usage.

The telecommunications management module 225 may further be adapted to send and receive data across the network interface 315 to a telecommunication provider web service 805 for the purposes of reporting telecommunications usage, retrieving telecommunications usage, retrieving telecommunication rates and the like.

As is apparent from the figure, the telecommunications management module 225 may interface with the contacts and diaries module 700 for the purposes of supplementing telecommunication usage information, for example with contact information and the like.

Internet Access and Management Module

Figure 9:
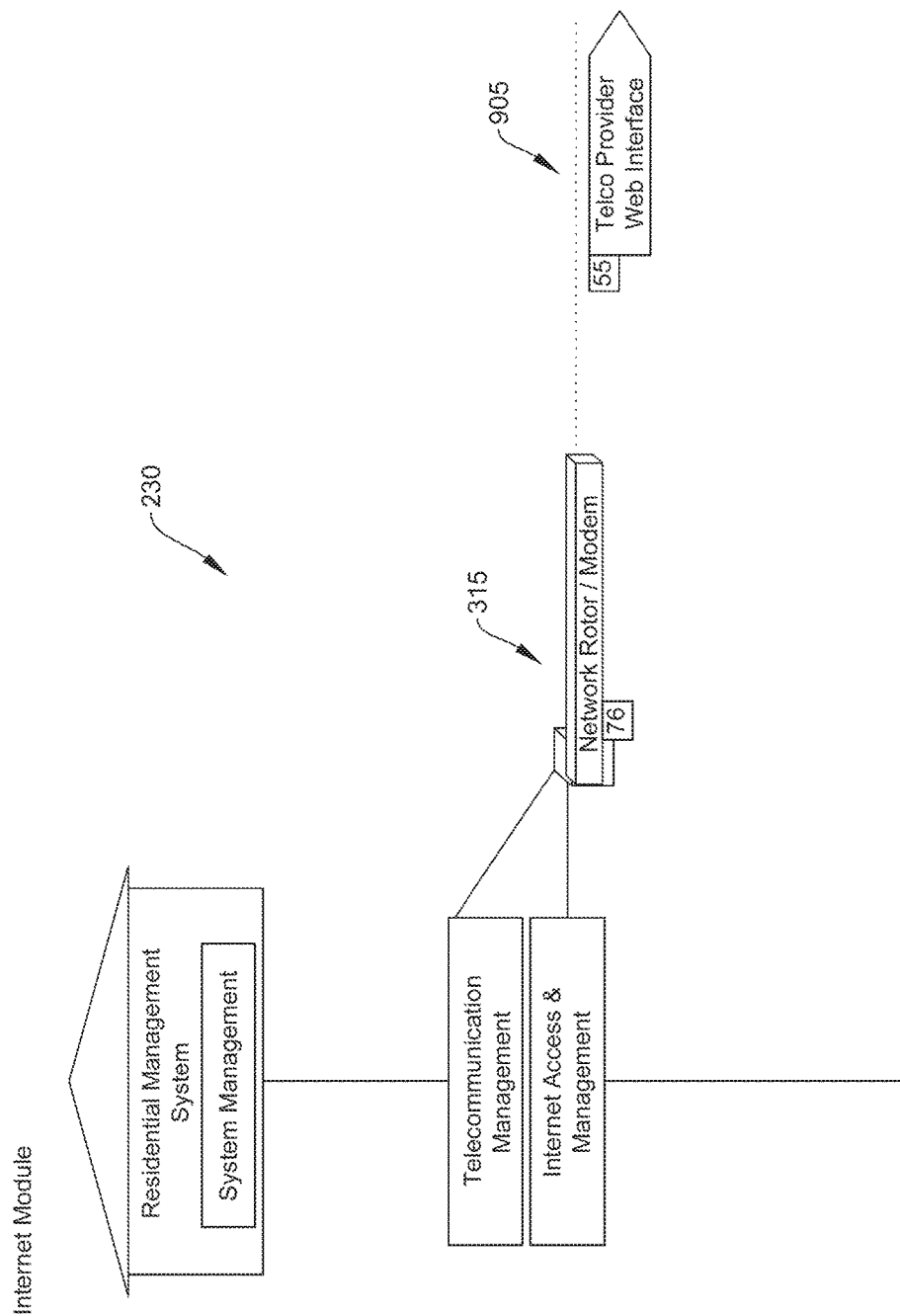
FIG. 9 shows a schematic of the contacts and diaries module in accordance with an embodiment of the present invention.

In a similar manner for which the telecommunications management module 225 is employed, the residential management system 200, referring specifically to FIG. 9, comprises a Internet access management module 230 adapted for keeping accurate records of personal and shared Internet access and usage.

The Internet access management module 230 may determine Internet access and usage in a number of manners, such as by interlacing with the network interface 315, or by receiving Internet usage information from an Internet provider web service 905.

The access and usage information may comprise the total usage, individual usage breakdown, cost and the like.

Intelligence for Fun Module 235

Referring again to FIG. 2, there is shown the residential management system comprising a intelligence for fun module 235 adapted for providing teaching and learning functionality for users, including by way of interactive games.

Figure 10:
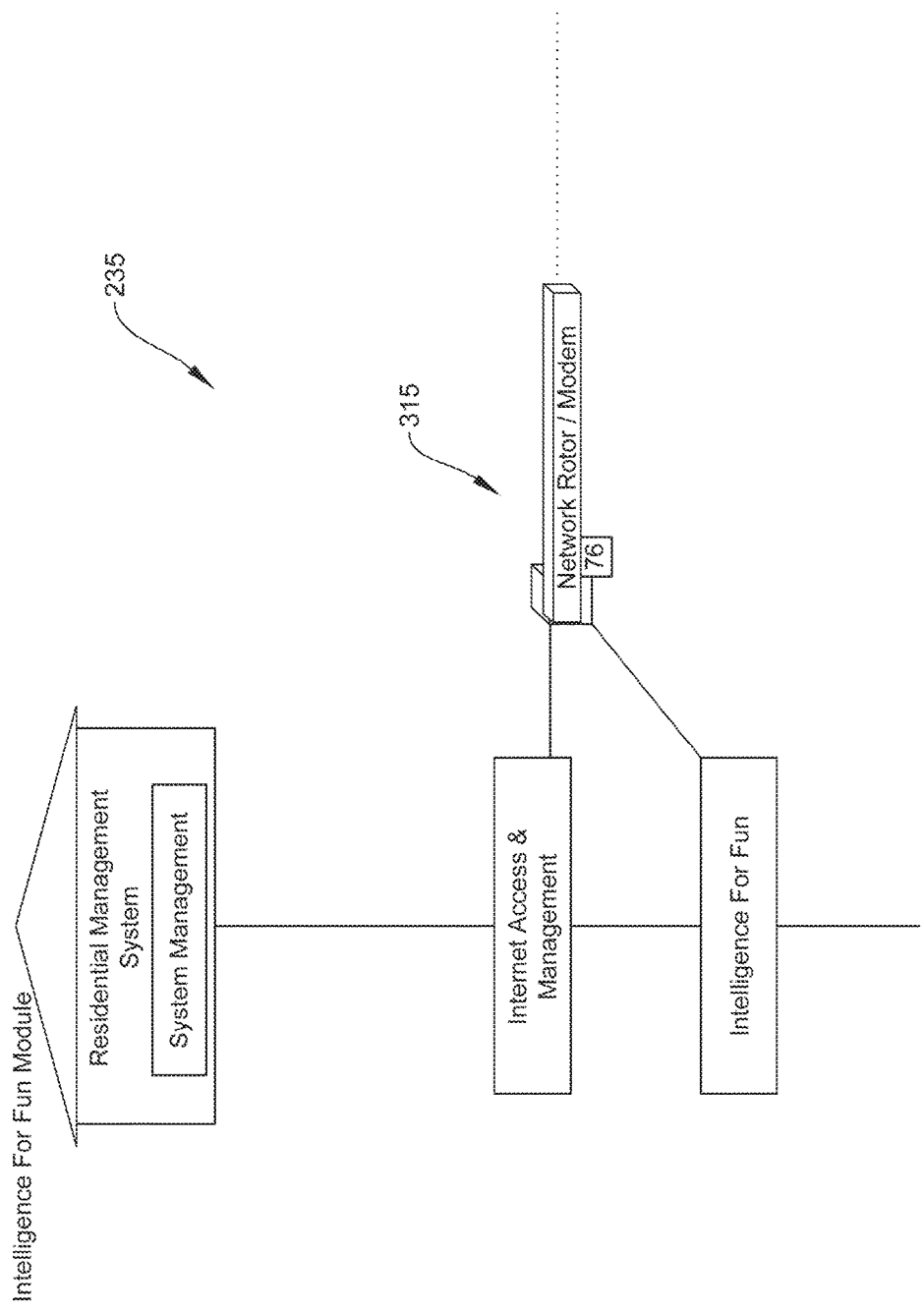
FIG. 10 shows a schematic of the telecommunications module in accordance with an embodiment of the present invention.

Specifically, referring to FIG. 10, there is shown the intelligence for fun module 235 in further detail.

The intelligence for fun module 235 may provide learning and teaching functionality in accordance with different interaction levels for users within a household, which interaction levels may be determined in accordance with the user's age for example.

It should be noted that the games and activities provided by the intelligence for fun module 235 may be supplied by the system and/or downloaded from specifically accredited third-party game providers via the network interface 315.

Electronic Vehicle Log Book 240

Figure 11:
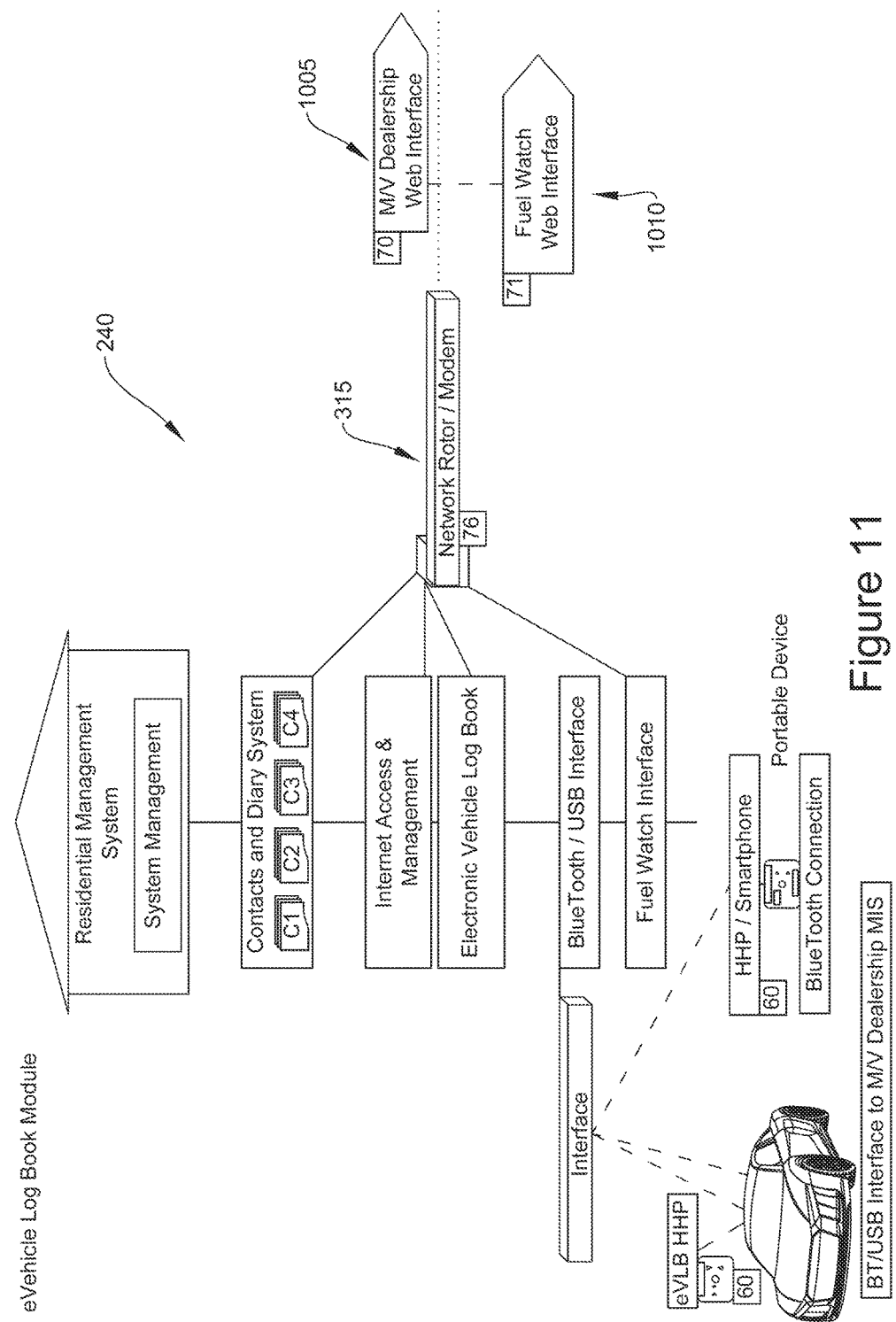
FIG. 11 shows a schematic of the Internet module in accordance with an embodiment of the present invention.

Referring again to the residential management system 201) as substantially shown in FIG. 2, the residential management system 201) further comprises an electronic vehicle log book module 240. Referring also to FIG. 11, there is shown the electronic vehicle log book module 240 in further detail.

The electronic vehicle log book module 240 provides an electronic log of the use of specified motor vehicle. During configuration, the residential management system 200 is provided with vehicle identification data which may include the vehicle identification number chassis number and the like so as to create a vehicle log within the residential management system 200. Again, the electronic vehicle log book module 240 may be single user or multi-user and may provide data sharing abilities for multi-user application.

The electronic vehicle log book module 240 may provide various functionality including a vehicle scheduling diary wherein, by interfacing with the contacts and diaries module 220, the electronic vehicle log book module 240 is adapted for scheduling vehicle booking with a vehicle administrator. The electronic vehicle log book module 240 may be adapted to log the vehicle service history as a vehicle service log whereas also export this vehicle service log. In this regard, the electronic vehicle log book module 240 may be adapted for interfacing, via the network interface 315, with a dealership's Management Information System's Web interface 1005 for the purposes of confirming availability and the resulting scheduling for a vehicle's service booking and the like.

Furthermore, the electronic vehicle log hook module 240 may provide travel planner functionality, allowing users to input details relating to proposed travel plans, including travel destination, sundry costs and the like. In this regard, the electronic vehicle logbooks of module 240 may Interface, via the network interface 315 with a fuel watch web service 1010 for the purposes of retrieving fuel pricing information in accordance with location. In this manner, the electronic vehicle log hook module 240 may be adapted for completing fuel pricing in accordance with travel plan information input by the user.

Health Care Management Module 245

Referring again to FIG. 2, there is shown the residential management system 200 comprising a healthcare management module 245 adapted for assisting users in improving or maintaining health through improved management of health records which may include health records from birth through to old age. Specifically, during differing phases of a user's life, the user may require differing health care management. For example, during childhood, immunisation may be required.

Figure 12:
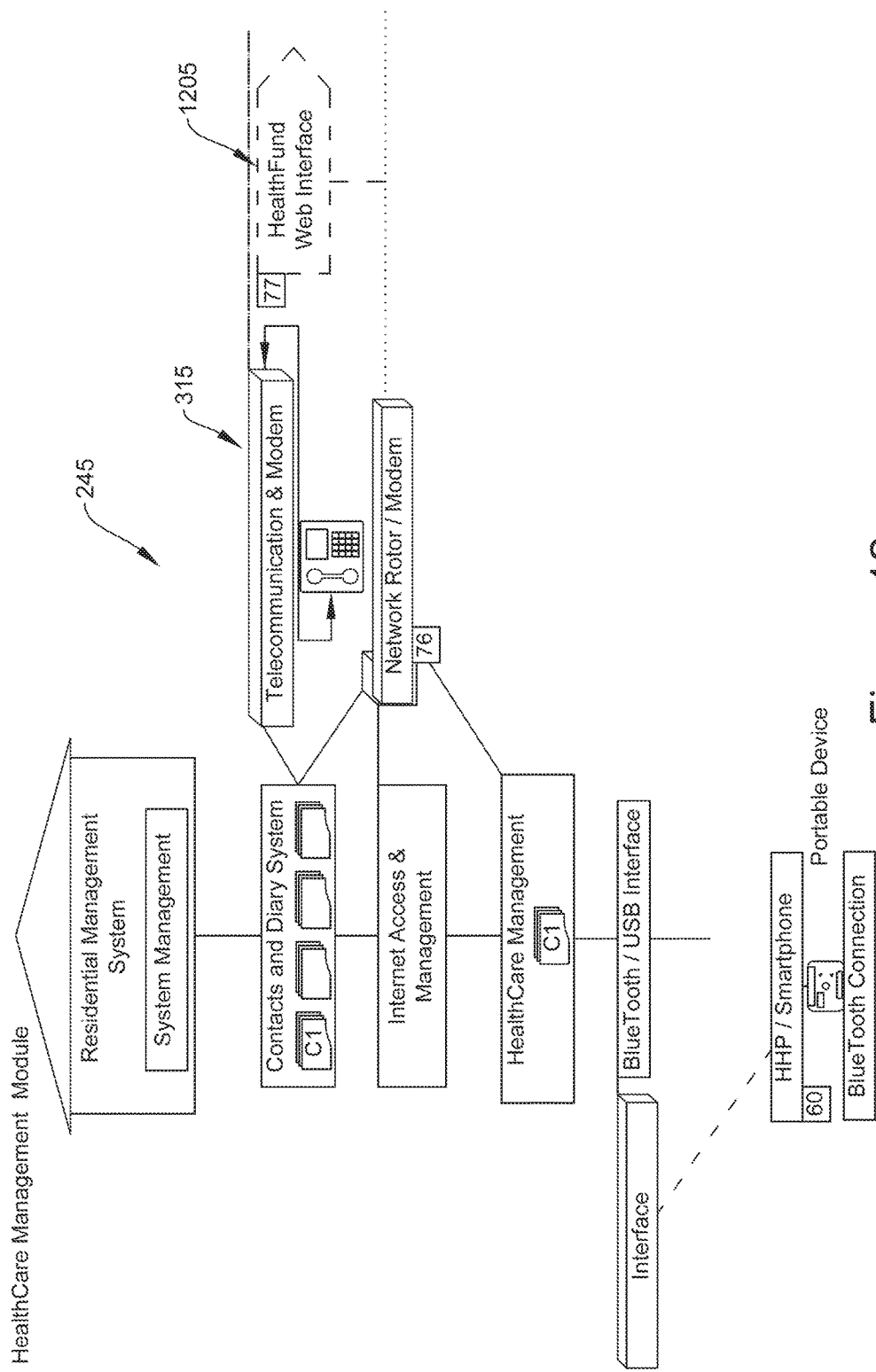
FIG. 12 shows a schematic of the intelligence for fun module in accordance with an embodiment of the present invention.
Figure 13:
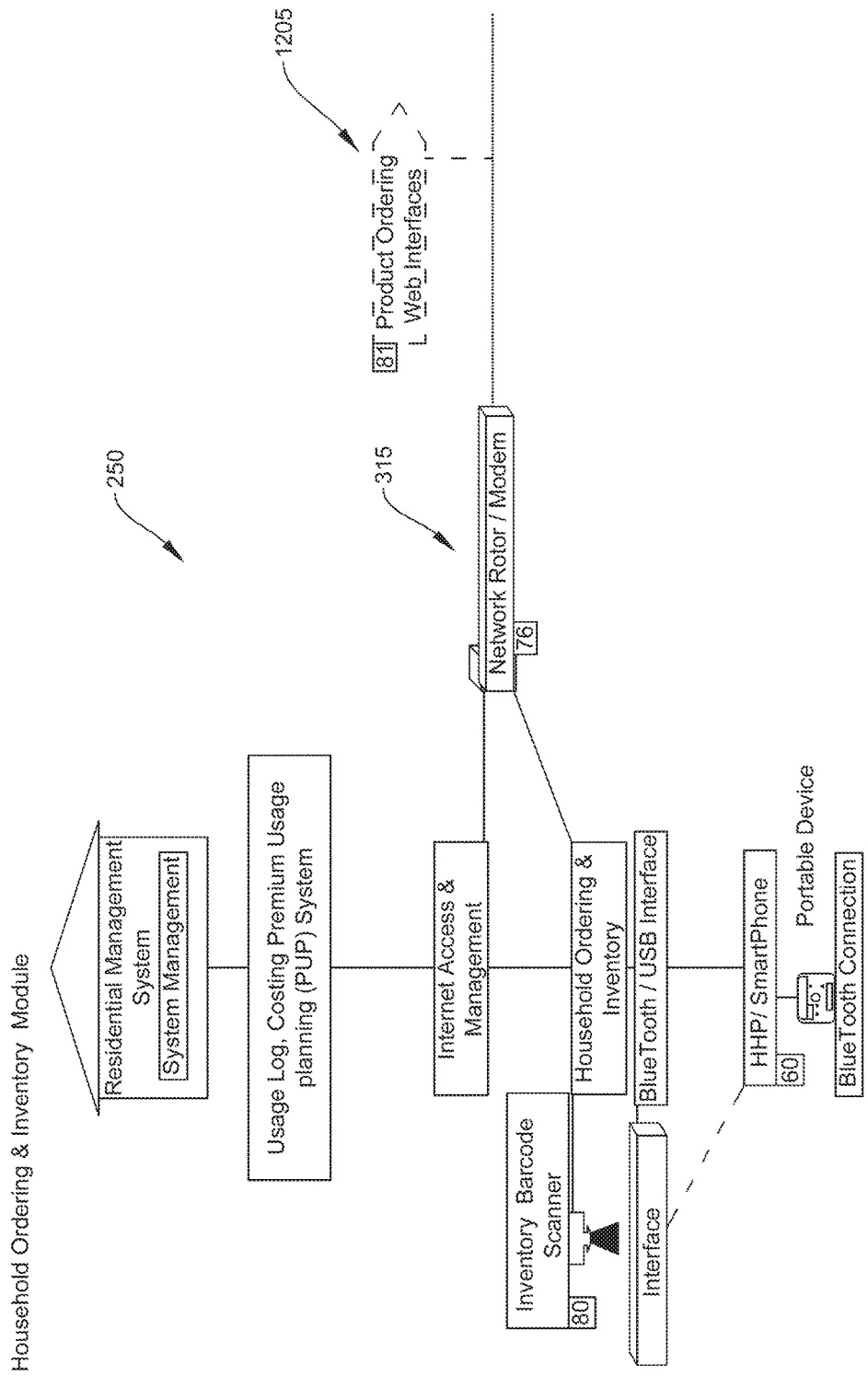
FIG. 13 shows a schematic of the electronic log book module in accordance with an embodiment of the present invention.
Figure 14A:
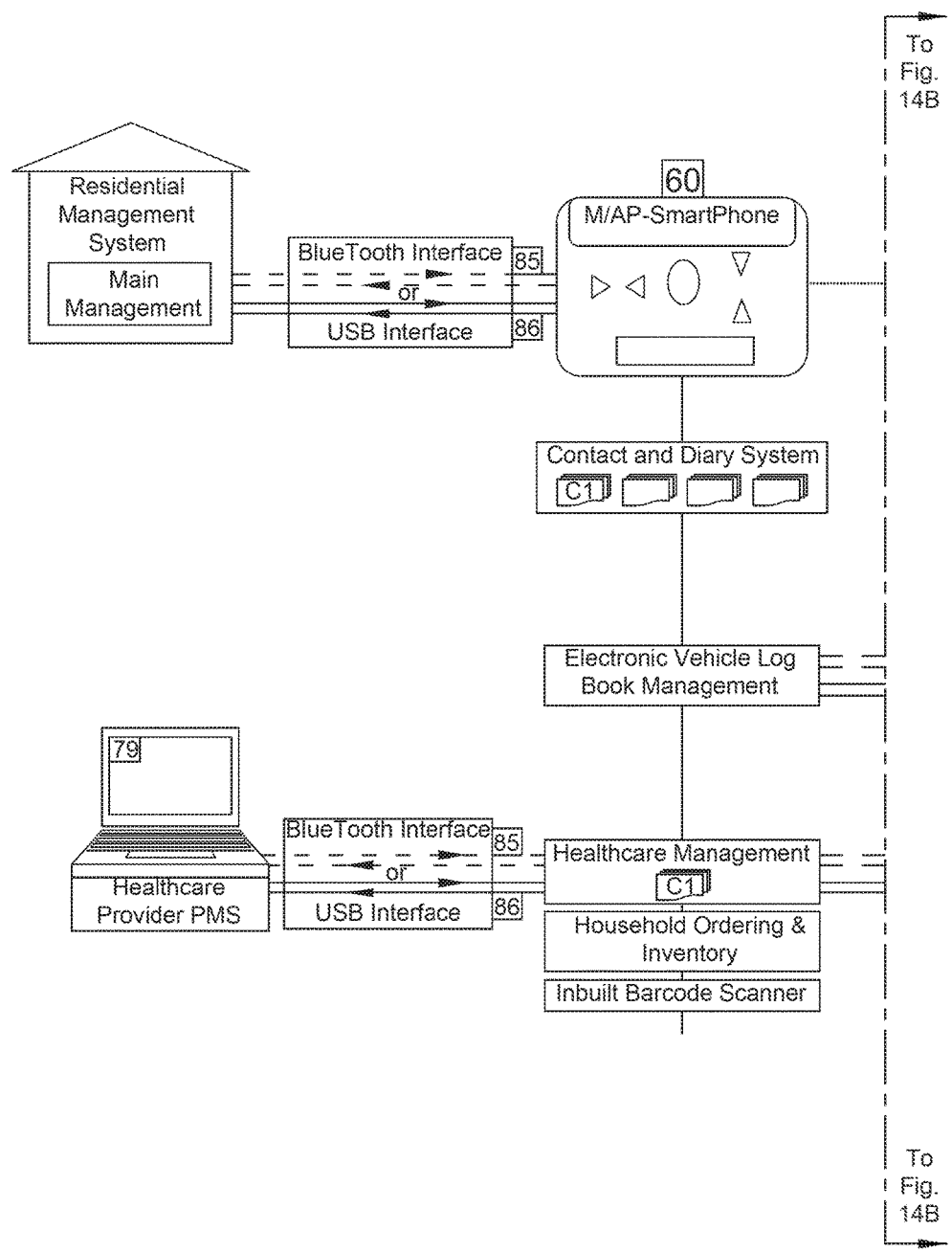
FIGS. 14A and 14B show a schematic of the healthcare management module in accordance with an embodiment of the present invention.
Figure 14B:
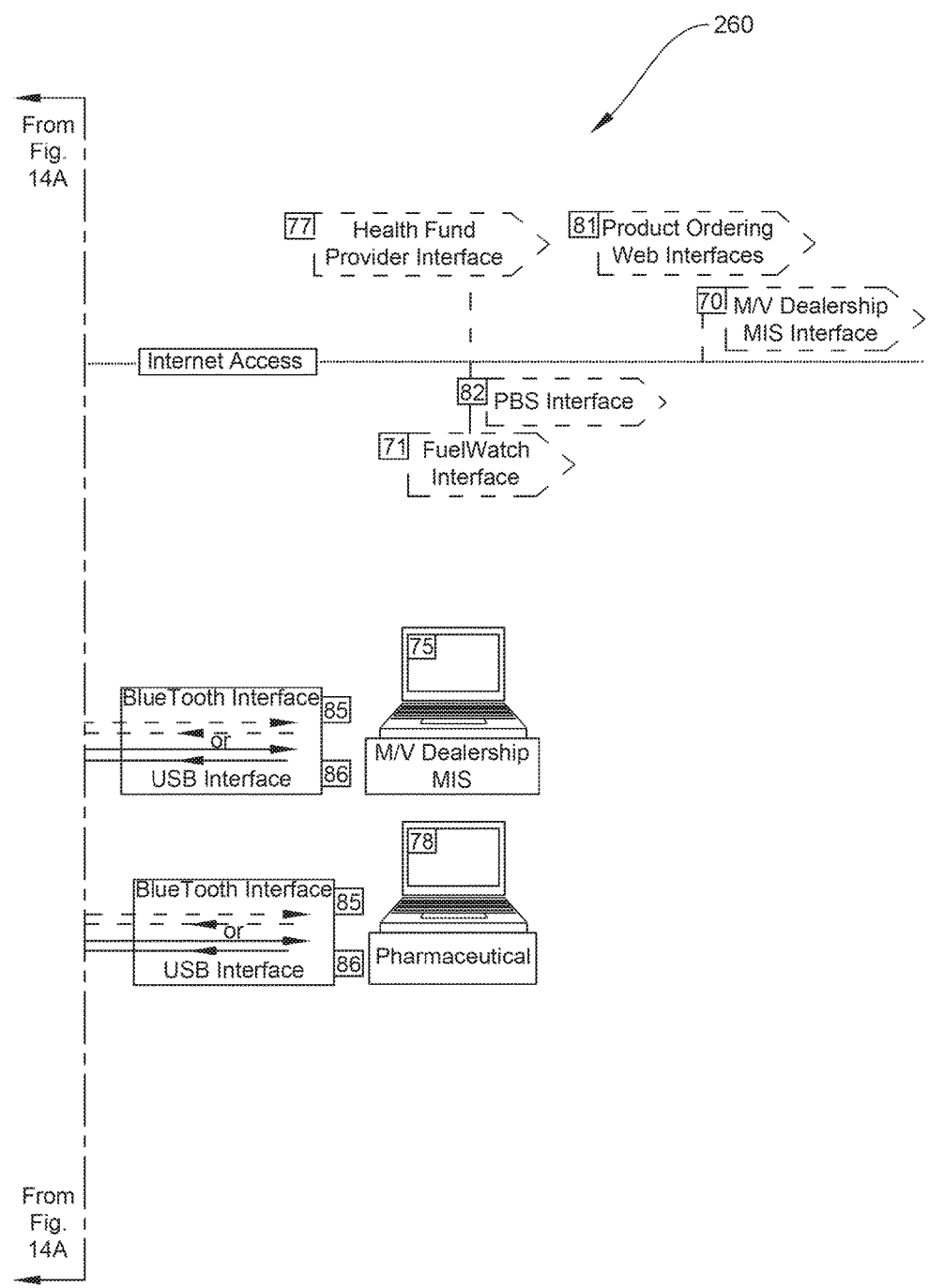

Referring to FIG. 12, there is shown the healthcare management module 245 in further detail.

During configuration, the residential management system 200 is provided with User/Healthcare identification data which may include the Healthcare or as in Australia, the user's Medicare identification number and the like so as to create a User Healthcare log within the residential management system.

As such, the healthcare management module 245 may be adapted for communicating, via the network interface 315 with a healthcare provider's practice management system, a healthcare clinic or hospital patient management system or healthcare web service 1205 for the purposes of updating and retrieving medical records, retrieving medical information, scheduling and confirming availability of medical appointments, reporting on medical conditions and the like.

In another embodiment, the healthcare management module 245 is adapted for the purpose of privacy control over what information is allowed to be merged, transferred and/or synchronised as user personal health records.

In one embodiment, the healthcare management module 245 is adapted for monitoring symptoms of a user by allowing the user to periodically input symptom data into the healthcare management module 245. In this manner, the healthcare management module, either in an automated manner or by sending and receiving information across the network interface 315 may be adapted for assisting a healthcare provider in diagnosing illness in accordance with the symptoms input by the user.

In another embodiment, the healthcare management module 245 is adapted for ensuring compliance of a user with a prescription regime. For example, a medical practitioner may prescribe a prescription regime and enter the prescription regime into the medical practitioner's practice management system or a health services database web service. The healthcare management module 245 is adapted to receive, via a bus device or the network interface, from the practice management system or health services database web service, the prescription regime, so as to be able to generate alerts in accordance with the prescription regime to remind the user to adhere to the prescription regime.

In another embodiment, the healthcare management module 245 is adapted for managing the exercise regime of a user which may or may not be prescribed by a health provider and if entered into the user diary as an activity using the exercise option, will become part of the user personal health records.

In another embodiment, the healthcare management module 245 is adapted for developing or to be invited to or to manage, personal and/or group exercise activities and/or regimes and if entered into the user diary as an activity using the exercise option, will become part of the user personal health records.

In another embodiment, the healthcare management module 245 is adapted for managing the dietary requirements of the individual user and/or family and if entered into the user or shared diary as an activity using the food consumption option, will become part of the user's personal health records.

In another embodiment, the healthcare management module 245 is adapted for integrating the recipe' library; exercise management and dietary requirements into personal and/or shared diaries to help users better manage food intake, exercise and dietary requirements for better management of various health conditions and requirements.

In another embodiment, the healthcare management module 245 is adapted for assisting the user to manage their Healthcare fund membership and associated payments and receipts accordance with the user's financial and medical needs.

Household Ordering Inventory Module 250

Referring again to FIG. 2, the residential management system 200 further comprises a household ordering and inventory module 250 adapted in assisting users in managing household inventory, including grocery inventory so as to assist in meal planning and the like.

Specifically, referring FIG. 12, there is shown the household ordering and inventory module 250 in further detail. The household ordering and inventory module 250 is adapted recording inventory data relating to at least one inventory of a household. In this regard, the household ordering and inventory module 250 may be adapted for updating the inventory data upon receipt of supply and consumption data in relation to the inventory. The supplier of such supply and consumption data may be input mainly by a user, or may be automated such as when, for example a user removes an item from a fridge, the user scans the barcode of the item from which the household ordering and eventually module 250 is adapted for identifying the removed item so as to note the depletion of the item from the inventory.

In one embodiment, the household ordering an inventory module 250 is adapted for automating the ordering of items for the replenishment of a depleted inventory. In this regard, the household ordering and inventory module 250 is adapted for requesting, via the network interface 315, front a remote product ordering fulfillment web service 1205 one or more items for order. The items ordered in this manner may be ordered in an automated manner by the household ordering and inventory module 250, car alternatively upon prompt from a user or alternatively upon receiving the listed items, manually by the user and manually recorded as ordered by the user.

In another embodiment the household ordering and invent module 250 is adapted for maintaining a record of various recipes' as a recipe' library including nutritional values.

In one embodiment, the inventory relates to a grocery inventory, and wherein the household ordering and inventory module 250 is adapted for maintaining the grocery inventory accordance with a dietary regime of the user. In this regard, the household ordering and inventory module 250 may be furthermore adapted for the purposes of recommended to one or more users the groceries recommended for use in meals.

HANDHELD MOBILE APPLICATION as Stand-Alone Product 260

Referring now to FIG. 2, there is shown the handheld mobile application 260 adapted for providing portable access to specific modules only available on the Mobile application 260. Specifically, using the handheld mobile application 260, the user is able to use the various functional aspects oldie specific modules of the mobile application 260 as described herein. Furthermore, the user, using the handheld mobile application 260 is able to view various information provided by those specific modules of the mobile application 200.

It should be noted that in one embodiment, the handheld mobile application 260 take the form of an off-the-shelf mobile computing device, such as a mobile telecommunication to device which functionality described herein may be provided by way of the mobile application 260 being a downloadable software application, such as a software application downloaded from the Apple iTunes store.

Interpretation

Bus

In the context of this document, the term "bus" and its derivatives, while being described in a preferred embodiment as being a communication bus module for interconnecting various devices including by way of parallel connectivity such as Industry Standard Architecture (ISA), conventional Peripheral Component Interconnect (PCI) and the like or serial Connectivity such as PCI Express (PCIe), Serial Advanced Technology Attachment (Serial ATA) and the like, should be construed broadly herein as any system for communicating data.

In Accordance with:

As described herein, 'in accordance with' may also mean 'as a function of' of and is not necessarily limited to the integers specified in relation thereto.

Composite Items

As described herein, 'a computer implemented method' should not necessarily be inferred as being performed by a single computing device such that the steps of the method may be performed by more than one cooperating computing devices.

Similarly objects as used herein such as 'web server', 'server', 'client computing device', 'computer readable medium' and the like should not necessarily be construed as being a single object, and may be implemented as a two or more objects in cooperation, such as, for example, a web server being construed as two or more web servers in a server farm cooperating to achieve a desired goal or a computer readable medium being distributed in a composite manner, such as program code being provided on a compact disk activatable by a license key downloadable from a computer network.

Database:

In the context of this document, the term "database" and its derivatives may be used to describe a single database, a set of databases, a system of databases or the like. The system of databases may comprise a set of databases wherein the set of databases may be stored on a single implementation or span across multiple implementations. The term "database" is also not limited to refer to a certain database format rather may refer to any database format. For example, database formats may include MySQL, MySQLi, XML or the like.

Wireless:

The invention may be embodied using devices conforming to other network standards and for other applications, including, for example other WLAN standards and other wireless standards. Applications that can be accommodated include IEEE 802.11 wireless LANs and links, and wireless Ethernet.

In the context of this document, the term "wireless" and its derivatives may be used to describe circuits, devices, systems, methods, techniques, communications channels, etc., that may communicate data through the use of modulated electromagnetic radiation through a non-solid medium. The term does not imply that the associated devices do not contain any wires, although in some embodiments they might not. In the context of this document, the term "wired" and its derivatives may be used to describe circuits, devices, systems, methods, techniques, communications channels, etc., that may communicate data through the use of modulated electromagnetic radiation through a solid medium. The term does not imply that the associated devices are coupled by electrically conductive wires.

Processes:

Unless specifically stated otherwise, as apparent from the following discussions, it is appreciated that throughout the specification discussions utilizing terms such as "processing", "computing", "calculating", "determining", "analysing" or the like, refer to the action and/or processes of a computer or computing system, or similar electronic computing device, that manipulate and/or transform data represented as physical, such as electronic, quantities into other data similarly represented as physical quantities.

Processor:

in a similar manner, the term "processor" may refer to any device or portion of a device that processes electronic data, e.g., from registers and/or memory to transform that electronic data into other electronic data that, e.g., may be stored in registers and/or memory. A "computer" or a "computing device" or a "computing, machine" or a "computing platform" may include one or more processors.

The methodologies described herein are, in one embodiment, performable by one or more processors that accept computer-readable (also called machine-readable) code containing, a set of instructions that when executed by one or more of the processors carry out at least one of the methods described herein. Any processor capable of executing a set of instructions (sequential or otherwise) that specify actions to be taken are included. Thus, one example is a typical processing system that includes one or more processors. The processing system further may include a memory module including main RAM and/or a static RAM, and/or ROM.

Computer-Readable Medium:

Furthermore, a computer-readable carrier medium may form, or be included in a computer program product. A computer program product can be stored on a computer usable carrier medium, the computer program product comprising a computer readable program means for causing a processor to perform a method as described herein.

Networked or Multiple Processors:

in alternative embodiments, the one or more processors operate as a standalone device or may be connected, e.g., networked to other processor(s), in a networked deployment, the one or more processors may operate in the capacity of a server or a client machine in server-client network environment, or as a peer machine in a peer-to-peer or distributed network environment. The one or more processors may form a web appliance, a network router, switch or bridge, or any machine capable of executing a set of instructions (sequential or otherwise) that specify actions to be taken by that machine.

Note that while some diagram(s) only show(s) a single processor and a single memory that carries the computer-readable code, those in the art will understand that many of the components described above are included, but not explicitly shown or described in order not to obscure the inventive aspect. For example, while only a single machine is illustrated, the term "machine" shall also be taken to include any collection of machines that individually or jointly execute a set (or multiple sets) of instructions to perform any one or more of the methodologies discussed herein.

Additional Embodiments:

Thus, one embodiment of each of the methods described herein is in the form of a computer-readable carrier medium carrying a set of instructions, e.g., a computer program that are tot execution on one or more processors. Thus, as will be appreciated by those skilled in the art, embodiments of the present invention may be embodied as a method, an apparatus such as a special purpose apparatus, an apparatus such as a data processing system, or a computer-readable carrier medium. The computer-readable carrier medium carries computer readable code including a set of instructions that when executed on one or more processors cause a processor or processors to implement a method. Accordingly, aspects of the present invention may take the form of a method, an entirely hardware embodiment, an entirely software embodiment or an embodiment combining software and hardware aspects. Furthermore, the present invention may take the form of carrier medium (e.g., a computer program product on a computer-readable storage medium) carrying computer-readable program code embodied in the medium.

Carrier Medium:

The software may further be transmitted or received over a network via a network interface device. While the carrier medium is shown in an example embodiment to be a single medium, the term "carrier medium" should be taken to include a single medium or multiple media (e.g., a centralized or distributed database, and/or associated caches and servers) that store the one or more sets of instructions. The term "carrier medium" shall also be taken to include any medium that is capable of storing, encoding or carrying a set of instructions for execution by one or more of the processors and that cause the one or more processors to perform any one or more of the methodologies of the present invention. A carrier medium may take many forms, including but not limited to, non-volatile media, volatile media, and transmission media.

Implementation:

It will be understood that the steps of methods discussed are performed in one embodiment by an appropriate processor (or processors) of a processing (i.e., computer) system executing instructions (computer-readable code) stored in storage. It will also be understood that the invention is not limited to any particular implementation or programming technique and that the invention may be implemented using any appropriate techniques for implementing the functionality described herein. The invention is not limited to any particular programming language or operating system.

Means for Carrying Out a Method or Function

Furthermore, some of the embodiments are described herein as a method or combination of elements of a method that can be implemented by a processor of a processor device, computer system, or by other means of carrying out the function. Thus, a processor with the necessary instructions for carrying out such a method or element of a method forms a means for carrying out the method or element of a method. Furthermore, an element described herein of an apparatus embodiment is an example of a means for carrying out the function performed by the element for the purpose of carrying out the invention.

Connected

Similarly, it is to be noticed that the term connected, when used in the claims, should not be interpreted as being limitative to direct connections only. Thus, the scope of the expression a device A connected to a device B should not be limited to devices or systems wherein an output of device A is directly connected to an input of device B. It means that there exists a path between an output of A and an input of B which may be a path including other devices or means, "Connected" may mean that two or more elements are either in direct physical or electrical contact, or that two or more elements are not in direct contact with each other but yet still co-operate or interact with each other.

Embodiments:

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined, in any suitable manner, as would be apparent to one of ordinary skill in the art from this disclosure, in one or more embodiments.

Similarly it should be appreciated that in the above description of example embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description of Specific Embodiments are hereby expressly incorporated into this Detailed Description of Specific Embodiments, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

Specific Details

In the description provided herein, numerous specific details are set forth. However, it is understood that embodiments of the invention may be practiced without these specific details. In other instances, well-known methods, structures and techniques have not been shown in detail in order not to obscure an understanding of this description.

Terminology

In describing the preferred embodiment of the invention illustrated in the drawings, specific terminology will be resorted to, for the sake of clarity. However, the invention is not intended to be limited to the specific terms so selected, and it is to be understood that each specific term includes all technical equivalents which operate in a similar manner to accomplish a similar technical purpose. Terms such as "forward", "rearward", "radially", "peripherally", "upwardly". "downwardly", and the like are used as words of convenience to provide reference points and are not to be construed as limiting terms.

Different Instances of Objects

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporarily, spatially, in ranking, or in any other manner.

Comprising and Including

In the claims which follow and in the preceding description of the invention, except where the context requires otherwise due to express language or necessary implication, the word "comprise" or variations such as "comprises" or "comprising" are used in an inclusive sense, i.e. to specify the presence of the stated features but not to preclude the presence or addition of further features in various embodiments of the invention.

Any one of the terms: including or which includes or that includes as used herein is also an open term that also means including at least the elements/features that follow the term, but not excluding others. Thus, including is synonymous with and means comprising.

Scope of Invention

Thus, while there has been described what are believed to be the preferred embodiments of the invention, those skilled in the art will recognize that other and farther modifications may be made thereto without departing from the spirit of the invention, and it is intended to claim all such changes and modifications as fall within the scope of the invention. For example, any formulas given above are merely representative of procedures that may be used. Functionality may be added or deleted from the block diagrams and operations may be interchanged among functional blocks. Steps may be added or deleted to methods described within the scope of the present invention.

Although the invention has been described with reference to specific examples, it will be appreciated by those skilled in the art that the invention may be embodied in many other forms.

Industrial Applicability

It is apparent from the above, that the arrangements described are applicable to the residential management system industry.

Appendix A—Technical Data

The overall Residential Management System hereafter referred to as RMS will help Resident Users focus on aspects of their Household and Lives that are more easily managed using the benefits of technology currently available and that of the fixture.

The Residential Management System also provides areas of Personal Management that due to technology, are now more easily and more practically managed through this technology. The management advantages the technology delivers in each area of the System are seen as Functional Management; Resource Management; Budgetary Management in both Savings to be made from more prudent Consumption and also Planning and the final, Personal Health Management.

Terminology and Standards
  a. System Design and Structure:
    Database Structure will be—
      SQL Relational Database
  b. Terminology:
    User and/or User/Patient refers to User, the System is Registered to
    HCP refers to Healthcare Provider of User/Patient, the System is Registered to
      This can include both Public Institutions; Hospitals & Clinics and Private Institutions; Hospitals; Clinics & Private Practices
    Institutional De-Identified PHR Datashare (dID-PHR)—Only available to Preset Institutions
    PHR refers to Personal Health Records of User/Patient
    R/T refers to Real-Time
    HHP refers to a Portable Hand-held Peripheral device such as a Mobile or Smart Phone ideally capable of Internet access and sufficient memory for running the Mobile Application module The HHP must provide a sufficient level of Log-on Password Security M/APP refers to the Mobile Application version/module of the System c. System Principals:
  Access/Data/Entry Principals
    All Access/Entries/Changes Synchronise only made by Approved Level Access
    All Diary Entries/Changes—ID/Time/Date Logged to establish Audit Trail
    All PHR Diary Entries/Changes—ID/Time/Date Logged, maintained and available as PHR d. System Integration:
  $3^{RD}$ Party Systems Integration
  Voice Recognition System
  PDF Writer
  Email and Calendar System
  Barcode Scanner
  Peripheral Integration—Industry Standard Interface
    Mouse—Cable, Inferred & Bluetooth
    Keyboard—Cable, Inferred & Bluetooth
    Proprietary Interface for Tablet integration and use e. Diary System:
  Diary System Offers—
  Personal Diary—by default includes PHR Appointments/Entries/Reminders
    NO PHR will be Merging. Transfer and/or Synchronisation unless Target Diary System has HL7 Gateway (HL7g)
    PHR Appointments/Entries/Reminders will show PHR Identification in Personal Diary
      If PHR Appointments/Entries/Reminders are set from other Diaries (Business/Household), they will show only P Identification (Id) & Colour Coded (CC) in the Diary set from
  PHR Diary—can be set as a separate PHR Diary if required by User
    Once a Child has a required Medicare number, a separate PHR Diary may be created and used within a Parent's Diary
      This Child's PHR Diary is Automatically Synchronised between Parent PHR Diaries
  Business Diary—Can be set to Synchronise on Demand with Office Diary
  Household Diary—All Users Access
    Each User has their Entries Colour Coded to the same Defaulted Colour—This Colour can be changed by the User
  All Diaries can be set to have Personal Diary entries Inserted and marked P(CC)
  Business and Household Diaries can be set to have Personal (P) and Personal Health Records (PHR) Appointments/Entries/Reminders made from within and marked either P(CC) or PHR(CC)
    In these cases, they will automatically insert (as pre-set) with Default Tag Eg.—
    P—"9:00 am P(CC)"—Available in Household Diary
    PHR—"9:00 am PHR(CC)"—Available in Household Diary
  When Multiple Diaries are used by the User, All Diary Entries outside their Specified Diary and if pre-set to show, are Default Tagged by the User: P (Personal); PHR (Personal Health Records); B (Business) and HH (Household)

f. Synchronisation and One/Two Way Data Transfer:
  Synchronisation of—
    i. All Diary Records including—
      User Personal Diary carrying PHR/PBS Records
      PHR Diary carrying PHR/PBS Records
      Business Diary
      Household Diary
    ii. Other Standard Communication and Information Synchronisation and one/two way data transfer
  Software Development Kit (SDK) will be provided to Specific and Approved System and Software Vendors requiring System Integration
  Synchronisation and one/two way data transfer of M/APP with:
    Any PHR Merging, Transfer and/or Synchronisation will require the User/Patient to confirm merging, transfer and/or Synchronisation with their PHR Validation Log-in (secondary) PHR Validation Code
    Main System—HL7 Gateway—PBS/PHR
    Healthcare Provider's Practice Management System—HL7 Gateway—PBS/PHR
    Pharmacy Point of Sale System—HL7 Gateway—PBS
  Synchronisation and one/two way data transfer Access Method
    via USB Cable
    via Bluetooth
    via Web Portal—Only available to Preset Institutions
    Non Specific Direct Communications link
  Synchronisation/Communication/Integration Standard
    HL7 Gateway
      Australia—NEHTA prescribed: Standards Australia Point to Point Secure Messaging Standards
      De-Identified PHR Datashare (dIDPHR) (Proprietary Standard)
      Point to Point Secure Messaging—National (Country Dependent) or International Standards (ISO)

Please Note—

This invention relates to the overall management of a Residential Household including in as many areas as seen practical, employing Artificial Intelligence including again in the areas seen practical, Voice Controlled through User Voice Recognition to both facilitate and encourage use, security and functionality of the system.

This is a unique use of such features within the everyday use of any type of management system. The system provides many areas of Household and Individual Resident Personal and Healthcare Management.

The system covers the following areas of management—
Module Index—
  1. System Management
  2. Household Power Management
  3. Household Water Management
  4. Household Gas Management
  5. Contacts & Diaries
  6. Household Accounts
  7. Security
  8. Telecommunications Management
  9. Internet Access
  10. Intelligence For Fun
  11. Electronic Vehicle Logo Book (eVLB)—Household/Main System
  12. Healthcare Management (Personal Health Records)—Household/Main System
  13. Household Ordering & Inventory 1.0 System Management
Module Overview:

The overall Residential Management System is designed to help residents focus on aspects of their premises that are more easily managed using the benefits of technology currently available and that of the future.

The System Management module provides the overall management capabilities to the Main System providing the Administrator and Users the ability to configure and manage the Main System to best suit their operational and interactive use of the System Initial Setup:
The Main System:

When creating an RMS Residential or User Start-up File, the system will require an Access License Code (Yet to be defined) from which it will create its own RMS Residential File and User File Codes.

The RMS Residential File
- i) The active RMS Residential File will be replaced with each New Address and Address Change
- ii) Only One RMS Residential Address at a time can be used for the System as an Active RMS Residential File
- iii) If a new RMS Residential Address is entered, the System creates an RMS Residential History File from the active RMS Residential File, with the RMS Residential History File Locked to that Address. This can be retained as an RMS Residential History File within the Main System indefinitely, with sufficient memory capacity.
  - (a) History Files can be set to Archived Status which then stores the file as a Compressed File
- iv) An active RMS Residential File can also be saved to any hard disk drive device including a HHP or USB device providing the device is compatible and has sufficient memory capacity
- v) An RMS Residential Back-up File can be created at anytime onto the System hard disk or any hard disk drive device including a HHP or USB device providing the device is compatible, with sufficient memory capacity
  This file can only be activated from the RMS System from which it was created or from a system that has been set-up by using the same Access License Code
- vi) An RMS Residential History File can be Exported and Transferred when a residence is sold and/or left The RMS User Files Codes (UFC) will be
- i) The System will not allow more than one User File per User at a time to be Active within the Active RMS Residential File.
  This means if a second User with the same given and surnames are the same as an existing User, the system will ask for clarification stating, "System will Archive existing duplicate—Do you wish to transfer History?"
- ii) To Create a User File, depending on the country of use, the System may require certain User ID
  - (a) Australia
    - (i) Given Name and Surname
    - (ii) Healthcare Management module—Medicare number is required
      Once the User is logged into the System, to access Personal Health Records (PHR) or associated PHR files, a PHR Validation Log-in (secondary) Code is required.
    - (iii) If a User with a PHR File has a Dependant Child and wishes to create a separate PHR File for the child
      1. This can be done by creating a Child Dependant PHR File if the Child has their own Medicare number
         a. The File will be Attached by default to both Parent PHR Files—An option will be given to Prevent this with a Warning Pop-up explaining the advantages to Parents always carrying PHR for the Dependant Children in case of Accidents and other Medical Emergencies or Situations
      2. Dependant Child PHR Files remain attached to the Parent PHR Files
      3. Dependant Child PHR Files can be Un-attached from the Parent PHR File/s once the Dependant Child reaches a permissible age and has been issued their own Medicare Card—This is done by the System Creating a New Contact with the Dependant Child's Details and Attaching the Child's PHR File
         a. Once Un-attached, the Child's PHR File will carry Parent Lineage History Only from Parent PHR
         b. Parent PHR Files will carry Previously Dependant Children PHR Files and can be Set to Archive Status at any time by each Parent within their own PHR File
    - (iv) eVLB module—Motor Vehicle Driver's License number if a Vehicle User
  - iii) Personal Health Records of the User can be sent as Personal Health Records Electronic Package Transfer (EPT) (Secured data)
  - iv) If a User wishes to leave the Household permanently, their Complete User File can be packaged into an EPT File and Exported to any hard disk drive device including a HHP or USB device providing the device is compatible and has sufficient memory capacity.
    - (a) This will require the User to be logged-in with Validation Log-in (secondary) Code. The User File including PHR will be Archived with access only available by the Access License Code with PHR not available without User Log-in and Validation Log-in (secondary) Code.

Specified Functions:
1.1 User Log-in and General Access provides User General Access to the system once Access Code Approved and logged to database—Once each of the system's modules are set-up.
  General Access will include—
  1.1.1 Appliance Usage Detection
    i. Single User Logged-in to Overall System
    ii. Multiple Users Logged-in to Overall System
    iii. Records Access
1.2 System Set-up—Set System Parameters and Alerts—
  i. Set All System Parameters
  ii. Set System Alarms & Alerts for Actions and Events
  1.2.1 Emergency Alarms—
    i. Security Alarm
    ii. Smoke Detection
  1.2.2 Reminders or Warnings of Environmental Status—
    i. Actions Required
    ii. Appliance Dollar Usage
    iii. Carbon Impact of specific Appliances and/or Entire Household
  1.2.3 Wellbeing Status Requests
    i. Wellbeing Requests are connected to the HealthCare Management module. They are to help any Individual Users with Illnesses that may require intervention such as Diabetics, Asthmatics and alike.

ii. Logic Questions are set-up by these Individuals Users so that where selected in the HealthCare Management section of System Set-up, the User defines their own Parameters and Questions to be asked by the system
iii. System Responses are also set-up by the User to match the individual medical condition and User needs 1.2.4 Voice Control System—
The System will offer Levels of Personality Nuances that will have a level of Artificial Intelligence giving The System the capacity to Learn from Ongoing Interaction with Users, learning each User's interaction styles and preferences.
i. Setup Mode will set system to match the User/s and Household Requirements
ii. Voice Recognition Teaching teaches the system voices of the User/s and statements to be recognised for certain Functional Commands of the system's operation
iii. Audible Response Teaching teaches the system the various Command and Answer Statements the system will use during particular operational functions
a. Operation Functions chosen by selection in Setup Mode
b. Answer Statements chosen by selection during Setup Mode 1.3 Take-A-Break Management provides the System Administrator and Backup Administrator the ability to set ongoing reminders at certain interval for Users to take a break from using the computer over an extended period of time. To encourage the User's compliance, these are provided with humorous or more serious consequences if ignored.

1.4 Household Contacts and Household Diary—
i. When selected, the Household's Contacts and Diary button gives the Household User access to the Household Contacts and Diary
ii. When selected, the User Contacts and Diary button and entering Personal User Code, gives the User access to the User's Personal User Contacts (C1 to C4) and Diary 1.5 Environment Audit produces an Audit of Entire Household and Individual Users at Their Choice including Motor Vehicles
This includes—
i. All Power Systems
ii. Water Systems
iii. Gas Systems—If used
iv. Motor Vehicles—If used
v. Air—If used
vi. Waist Management—If used
This includes comparisons of pre-selected Time Frames and pre-selected Past Periods.
The system then requests authority to send the Household Audit Results to the EPA in a De-Identified Format via EPA Web Portal Interface (42)

1.6 Environment Agency Enviro Updates
Acquisition of Environmental Updates, which means—
When the system needs to report on Environmental Updates it will source up to date Environmental Updates from Environmental Report Provider Web Portal Interface (40) depending on availability via Provider 1.7 Premium Usage Planning (PUP) System calculates the best use of Resources, certain Appliances and other Products that may be monitored by the system 1.8 Carbon Footprint—Current and Projected calculates the Actual and Projected Carbon Footprint of the Entire Household and Individual Users at Their Choice including Motor Vehicles
This includes comparisons of pre-selected Time Frames and pre-selected Past Periods.

1.9 Module Reporting sets parameters for the System Reports the Household and Individual Users require.
1.9.1 Household Power
i. Delivered Mains Power Validation—Mains Only
ii. Household Carbon Footprint
iii. Individual User usage
1.9.2 Household Water
i. Delivered Mains Water Validation
ii. Household Water Usage
iii. Individual User usage
1.9.3 Household Gas
i. Delivered Mains Gas Validation
ii. Household Gas Usage
iii. Individual User usage
1.9.4 Contacts & Diaries
i. Household Contacts
ii. Individual User Contacts
1.9.5 Household Accounts
i. All Household Accounts/Account Numbers
1.9.6 Security
i. Household Security
ii. Remote Motor Vehicle Security
1.9.7 Telecommunication Manager
i. Various Billing
1.9.8 Internet Access
i. Various Billing
1.9.9 Intelligence for Fun
i. Chess Challenge
ii. Championship Reporting
iii. Krazy Teacher
iv. Learning Reports
1.9.10 Electronic Vehicle Log Book
i. Vehicle Log Book
ii. Vehicle and User Log
iii. Vehicle Service History
iv. Projected Vehicle Costs
v. Individual Trip History Report
vi. Planned Trip Report
1.9.11 HealthCare Management
i. New Providing Practitioner PHR Full Report
ii. New Providing Practitioner PHR Report
iii. PBS Annual Report
iv. Full Meds Report
v. Current Medications
vi. Existing Providers PHR Limitations
1.9.12 Household Inventory & Ordering
i. Household Inventory
ii. Collective Report
iii. Individual Report 2.0 Household Power Management:
Module Overview:
The Household Power Management Module is specifically designed to be an aid in assisting Users to achieve and maintain more economic and predictable overall power usage.

With good Usage and Appliance Monitoring integration, the System allows Users to also understand better what areas of their individual and household lifestyle uses the power resource. For those households supplementing their power via $3^{RD}$ Party Catchment and/or Generating Systems, the System provides a means to also oversee the Management of such systems depending on the integration capabilities provided by the $3^{rd}$ Party System.

Module Functionality—

2.1 User Log-in:
  User Log-in for General Module Access is only necessary if User is NOT logging into the Main System
    User Log-in provides—
      i. Records Access
      ii. User Recognition—Date/Time Logged
      iii. Source Usage by User—Date/Time Logged
      iv. Appliance Usage by User—Date/Time Logged
      v. Timed Usage—Date/Time Logged 2.2 Power Usage:
  Power Usage—as measured through—
    2.2.1 User Usage—as assigned through Assign User function used in conjunction with Usage Monitoring will Capture—
      i. Current User Usage in Real-Time
      ii. Total Historical User Usage
      iii. Current Appliance/User Usage in Real-Time
      iv. Total Historical Appliance/User Usage
    2.2.2 Usage Monitoring—as measured through—
      i. Source Usage Detection, which means—when the System detects Usage (Levels pre-set within System Set-up) via hard wired feed direct from fitted Digital Power Usage Meters System (Schematic Location) where installed at Source
      ii. Appliance Usage Detection, which means—System detects Extra Power Usage (Levels pre-set within System Set-up) via hard wired feed direct from either—
        a. Fitted Digital Power Usage Meters at Appliances and/or Outlet/s (Schematic Locations)
        or
        b. Built-in Digital Power Usage Meters at Power Outlets (Schematic Locations)
      iii. Portable Digital Power Usage Meters (No Schematic Location), which means—meters that are specifically designed and are inbuilt into specific Powerboards, In-line and Power-point Outlets and hard wired feed direct to System
        All Fitted and Portable Digital Power Usage Meters must carry a Unique Digital ID Signal Code, which is Logged to System for Specific Function/s and/or Location/s
      iv. Portable Power Usage/User/Function Timer (21), which means—timers that are specifically designed and are hard wired or Bluetooth feed direct from specific function location and Manually Operated by the User undergoing a Selected Function using a Selected Appliance
      v. Timed Usage, which means as Usage Detection triggers System, the Usage Timer will be triggered and run until Usage is detected to stop. The Usage Time will be logged against the Appliance or Source it has been triggered by and User.
    2.2.3 Power Leakage Recognition as identified through—
      i. Volume Calculation under pre-set Source and Appliance Usage levels Once alerted to the Power Leakage by the System, Users can apply Location identification methods such as Circuit and Appliance Isolation to identify and remedy leakage where possible.

2.3 Mains Power:
  2.3.1 Mains Power Delivered (1)—as measured through—
    i. Source Usage Detection via hard wired feed direct from Power Provider's In-house Digital Power Meter System (5) (where installed)
    And/or
    ii. Appliance Usage Detection via hard wired feed direct from Set Locations
    And/or
    iii. Portable Usage/User/Function Timer/s
  2.3.2 Monitor Current Mains Power Delivered Real-Time Feed (R/T) via Source Usage Detection 2.4 Photovoltaic Power:
  2.4.1 Overview
    This Section is designed for the Home using or intends installing a commercially available Photovoltaic Power Generation System that is wired to the household as either Primary or Secondary Supply of Power with Digital Power Meter/s installed and tested according to System Specifications capable of feeding data back to System
  2.4.2 Generation and Delivery
    Photovoltaic Units will generate power from captured sunlight and deliver DC Power to either—
      a. Battery Storage System (30) (Storage Option)
      or
      b. AC/DC Inverter (31) to then deliver AC power (Non-Storage Option)
        If secondary Power Generation Systems are installed, the Battery Storage System will become the Common Household Battery Storage System from where power will then deliver to AC/DC Inverter
  2.4.3 Implementation
    Components to be installed—
      i. Photovoltaic Units (2)
      ii. Complete Wiring including Wiring Harnesses
      iii. Digital Power Meters
      iv. Portable Digital Power Usage Meter/s
      v. DC/AC Inverter (31)
      vi. Battery Storage System (30) (Optional)
      vii. Fuse Box (32) (Existing Household Standard)
        To be installed by Local Standards graded tradesman as a minimum and made operational in a Professional Manner to meet Local Government Standards
  2.4.4 Supply Costs
    Once the Photovoltaic Power Implementation Category is started, a Table of Costs will be created. This table once created, will be the ongoing Record of Costs associated with Photovoltaic System
      a. Supply Cost, which means—at the time of report, shall be the Total of the ongoing Record of Costs amortised over the Volume of Used Photovoltaic Power for the Period of Report.
      b. Mains Delivery, which means—at the time of report, the Cost of Mains Power Delivered amortised over the volume delivered for the Period of Report according to the Last Account. That per/unit (yet to be defined) Cost used to calculate against the Volume of Mains Power Delivered for Period of The Report.

2.4.5 Photovoltaic Power Usage
  i. User Usage—is assigned through Assign User function used in conjunction with Usage Monitoring
  ii. Usage Monitoring—as measured through—
    a. Source Usage Detection via fitted Digital Power Meter (2DC) at Battery Storage System (30) (if installed)
  And/or
    b. Appliance Usage Detection via hard wired feed direct from Set Locations
  And/or
    c. Portable Usage/User/Function Timer/s
2.5 2nd Alt. Power:
  2.5.1 Overview
    This Section is designed for the Home using or intends installing a commercially available 2nd Alt. Power Generation System that is wired to the household as either Primary or Secondary Supply of Power with Digital Power Meter/s installed and tested according to System Specifications capable of feeding data back to System
  2.5.2 Generation and Delivery
    $2^{nd}$ Alt. Power Unit/s will generate power from Alternative Source and deliver DC Power (2DC) to either—
      a. Battery Storage System (30) (Storage Option)
      or
      b. AC/DC Inverter (31) to then deliver AC power (Non-Storage Option)
        If secondary Power Generation Systems are installed, the Battery Storage System will become the Common Household Battery Storage System from where power will then deliver to AC/DC Inverter
  2.5.3 Implementation
    Components to be installed—
      i. 2nd Alt. Power Units (3)
      ii. Complete Wiring including Wiring Harnesses
      iii. Digital Power Usage Meter/s
      iv. Portable Digital Power Usage Meters (PDPUM)
      v. DC/AC Inverter (31)
      vi. Battery Storage System (30) (Optional)
      vii. Fuse Box (32) (Existing Household Standard)
  2.5.4 Supply Costs
    Once the 2nd Alt. Power Implementation Category is started, a Table of Costs will be created. This table once created, will be the ongoing Record of Costs associated with 2nd Alt. Power System
      a. Supply Cost, which means—at the time of report, shall be the Total of the ongoing Record of Costs amortised over the Volume of Used 2nd Alt. Power for the Period of Report.
      b. Mains Delivery, which means—at the time of report, the Cost of Mains Power Delivered amortised over the Volume Delivered for the Period of Report according to the Last Account. That per/unit (yet to be defined) Cost used to calculate against the Volume of Mains Power Delivered for the Period of Report.
  2.5.5 2nd Alt. Power Usage
    i. User Usage—is assigned through Assign User function used in conjunction with Usage Monitoring
    ii. Usage Monitoring—as measured through—
      a. Source Usage Detection via fitted Digital Power Meter (31AC) at DC/AC Inverter (31)
    And/or
      b. Appliance Usage Detection via hard wired feed direct from Set Locations
    And/or
      c. Portable Usage/User/Function Timer/s
2.5 Battery Bank Storage:
  2.5.1 Overview
    This Section is designed for the Home using or intends installing a commercially available battery Bank Storage Facility that is wired to the household as either Primary or Secondary Supply of Power with Digital Power Meter/s installed and tested according to System Specifications capable of feeding data back to System
  2.5.2 Power Storage and Delivery
    Battery Bank Unit/s will store DC power from Alternative Generation Sources and deliver DC Power to DC/AC Inverter
  2.5.3 Implementation
    Components to be installed—
      i. Battery Bank Units (30)
      ii. Complete Wiring including Wiring Harnesses
      iii. Digital Power Usage Meter/s
      iv. DC/AC Inverter (31)
  2.5.4 Supply Costs
    Once the Battery Bank Storage facility Category is started, a Table of Costs will be created. This table once created, will be the ongoing Record of Costs associated with Battery Bank Facility
      i. Supply Cost, which means—at the time of report, shall be the Total of the ongoing Record of Costs amortised over the Volume of Used Power Used for the Period of Report
      ii. Mains Delivery, which means—at the time of report, the Cost of Mains Power Delivered amortised over the Volume Delivered for the Period of Report according to the Last Account. That per/unit (yet to be defined) Cost used to calculate against the Volume of Mains Power Delivered for the Period of Report
  2.5.5 Battery Bank Power Usage:
    i. User Usage—is assigned through Assign User function used in conjunction with Usage Monitoring
    ii. Usage Monitoring—as measured through—
      a. Source Usage Detection via Fitted Digital Power Usage Meters (31DC) at Battery Bank Power Delivered to DC/AC Inverter (31)
    And/or
      b. Appliance Usage Detection via hard wired feed direct from Set Locations
    And/or
      c. Portable Usage/User/Function Timer/s
2.6 Back to Grid Export Power:
  2.6.1 Overview
    Mains Power Provider may pay Home Owner a Feed-In Tariff for each Kilowatt Hour produced by the grid connected Power Generating System This Section is designed for the Home Generating or intending to Generate Excess Power with the ability to use a Feed-In Tariff for each Kilowatt of Back To Grid facility provided by Power Providers that is wired to the household with Digital Power Meter/s installed and tested according to System Specifications capable of feeding data back to System
  2.6.2 Generate and Deliver
    This Section will deliver Excess Generated Power via Power Provider's Outbound Digital Power Meter, AC Power direct from the Household Inverter. This AC Power will be delivered resulting from either— i. Excess AC Power undrawn from Inverter
or
ii. Excess AC Power due to constant un-used Supply of DC Power to Battery Bank Storage Facility
2.6.3 Implementation
Components to be installed
i. Complete Wiring including Wiring Harnesses
ii. Digital Power Usage Meter (26AC) fitted after DC/AC Inverter hard wired feed to System
iii. Outbound Digital Power Meter (6) (Power Provider Supplied)
iv. DC/AC Inverter (31)
2.6.4 Supply Costs
Once the Back to Grid Export Power Implementation Category is started, a Table of Costs will be created. This table once created, will be the ongoing Record of Costs associated with Back to Grid Export Power
i. Supply Cost, which means—at the time of report, shall be the Total of the ongoing Record of Costs amortised over the Volume of Delivered Back to Grid Export Power for the Period of Report.
ii. Mains Delivery, which means—at the time of report, the Cost of Mains Power Delivered amortised over the Volume Delivered for the Period of Report according to the Last Account. That per/unit (yet to be defined) Cost used to calculate against the Volume of Mains Power Delivered for the Period of Report.
2.6.5 Power Exported
i. Exported monitoring as measured through—
a. Digital Power Usage Meter (26AC) fitted after DC/AC Inverter hard wired feed to System
b. Outbound Digital Power Meter (6) (Power Provider Supplied)
2.7 Power Buy Rates:
Acquisition of Mains Power Time/Rate Buy Rates, which means—When the system needs to report on Current Mains Power Buy Rates it will source upto date Time/Rate Buy Rates from Mains Power Provider Web Portal Interface (46) depending on availability via Provider
2.8 Module Reporting:
All Reports are Date/Time Logged
The System will Report on—
2.8.1 Mains Power
i. Mains Power Delivered—Source Usage Detection—Date/Time logged
ii. Monitor Current Mains Power Delivered R/T
iii. Monitor Current Power Usage R/T
iv. Acquisition of Mains Power Time/Rate Buy Rates via Network Rotor/Internet Modem (76) to Mains Power Provider Web Portal Interface and account access
v. Power & Appliances Usage—Date/Time logged
vi. Validation of Usage against Delivered
vii. Usage at Fuse box
viii. Delivered at Provider's Digital Power Meter
ix. Validation of Mains Provider Billing against Provider Delivered
x. Power & Appliance Usage Costing—Date/Time logged
2.8.2 Photovoltaic/2nd Alt. Power
i. Photovoltaic/2nd Alt. Power Cost/Return Analysis
ii. User Usage at Source (if NO Battery Storage installed)—Date/Time logged
iii. Battery Facility/Maintenance Schedule (If installed)
a. Existing Storage Level & Actual Volume of DC Power Held—Date/Time of Request & Pre-set Date/Time—logged
iv. Volume of DC Power Delivered & Split (If applicable) to Battery Storage System R/T (if installed)—Date/Time logged
v. Volume of DC Power Usage & Split (If applicable) from Battery Storage System R/T (if installed)—Date/Time logged
vi. Generated & Delivered vs Usage Validation
2.8.3 User Usage
i. Mains Usage
ii. Photovoltaic/2nd Alt. Power Usage
iii. Appliance Usage
iv. Total Power Usage
2.8.4 Back to Grid Export Power
i. Back to Grid Power Exported measured at Fitted Digital Power Meter (26AC)—Date/Time logged
ii. Back to Grid Power Exported measured at Power Provider's In-house Out-Bound Digital Power Meter System (6)—Date/Time logged vs Metered Power Exported, Date/Time logged
iii. Exported Power Validation of Fitted Digital Power Meter (26AC) against Power Provider's In-house Out-Bound Digital Power Meter System (6)
iv. Cost—Generated Only—
b. Costs Amortised over defined periods
c. vs Mains Delivered
2.8.5 Appliance Premium Usage Planning (PUP) against Mains Time/Rate Charges—
i. The system will cost out specific appliance usage against the available Time/Rate Zones and Best Photovoltaic Generation Times and make recommendations of better Appliance Usage Times
Other Efficiency recommendations
The extent of System Functionality and Effectiveness within a household environment will always depend on—
The level of Meter and Sensor Equipment integration with the System
The commitment and physical interaction Household Users of the System apply to the ongoing and regular use of the System. The more User interaction applied to the System, the better the return of quality and worthwhile information by the System
3.0 Household Water Management:
Module Overview:
The Household Water Management Module is specifically designed to be an aid in assisting Users to achieve and maintain more economic and predictable overall water usage.
With good Usage and Appliance Monitoring integration, the System allows Users to also understand better what areas of their individual and household lifestyle uses the water resource. For those households supplementing their water via $3^{RD}$ Party Catchment and/or Generating Systems, the System provides a means to also oversee the Management of such systems depending on the integration capabilities provided by the $3^{rd}$ Party System.
Module Functionality—
3.1 User Log-in:
User Log-in for General Module Access is only necessary if User is NOT logging into the main system
User Log-In provides—
i. Records Access
ii. User Recognition—Date/Time Logged
iii. Source Usage by User—Date/Time Logged
iv. Appliance Usage by User—Date/Time Logged
v. Timed Usage—Date/Time Logged 3.2 Water Usage:
Water Usage—as measured through—
3.2.1 User Usage—as assigned through Assign User function used in conjunction with Usage Monitoring will Capture—
   i. Current User Usage in Real-Time
   ii. Total Historical User Usage
   iii. Current Appliance/User Usage in Real-Time
   iv. Total Historical Appliance/User Usage
3.2.2 Usage Monitoring—as measured through—
   i. Source Usage Detection, which means—when the System detects Usage (Levels pre-set within System Set-up) via hard wired feed direct from fitted Digital Water Flow Rate Sensors/Meters System (Schematic Location) where installed at Source
   ii. Appliance Usage Detection, which means—System detects Extra Water Usage (Levels pre-set within System Set-up) via hard wired feed direct from fitted Digital Water Flow Rate Sensors/Meters at Appliances (Schematic Location/s) and/or Outlet/s
      All fitted Digital Water Flow Rate Sensors/Meters must carry a Unique Digital ID Signal Code, which is Logged to System for Specific Function/s and/or Outlet/s
   iii. Portable Water Usage/User/Function Timer (21), which means—timers that are specifically designed and are hard wired or Bluetooth feed direct from specific function location and Manually Operated by the User undergoing a Selected Function using a Selected Appliance
      Usage of Portable Water Usage/User/Function Timers is Manually Calibrated to an Estimated Volume of Water Usage per/second per/valve clearance against each Selected Appliance/Outlet
   iv. Timed Usage, which means as Usage Detection triggers System, the Usage Timer will be triggered and run until Usage is detected to stop. The Usage Time will be logged against the Appliance or Source it has been triggered by and User.
3.2.3 Water Leakage Recognition as identified through—
   i. Volume Calculation under pre-set Source and Appliance Usage levels Once alerted to the Water Leakage by the System, Users can apply Location Identification methods such as Forcett/Valve Isolation to identify and remedy leakage where possible.
3.3 Mains Water:
3.3.1 Mains Water Usage (14)—as measured through—
   i. Source Usage Detection via hard wired feed direct from Water Provider's In-house Digital Water Meter System (15) (where installed)
   And/or
   ii. Appliance Usage Detection via hard wired feed direct from Set Locations
   And/or
   iii. Portable Usage/User/Function Timer/s
3.3.2 Monitor Current Mains Water Delivered Real-Time Feed (R/T) via Source Usage Detection
3.4 Rainwater:
3.4.1 Overview
   This Section is designed for the Home using or intends installing a commercially available Rainwater Capture system that is plumbed to the household as either Primary or Secondary Supply of Water with Digital Flow Rate Sensor/s/Meter/s installed and tested according to System Specifications capable of feeding data back to System
3.4.2 Capture and Delivery
   Rainwater Storage System Tank will capture rainwater that lands and is drained into it from the Catchment Area and/or System Trap. If secondary Water Capture Systems are installed, the Storage System Tank will become the Common Household Storage System Tank from where water will then deliver to Appliances and other Outlet/s
3.4.3 Implementation
   Components to be installed—
   i. Rainwater Catchment Trap (19)
   ii. Complete Piping; Channel Plumbing and Plumbing Fittings
   iii. Digital Flow Rate Sensors/Meters
   iv. Water Storage System Tank (18) including Digital Water Level Gauge (20)
      To be installed by Local Standards Graded Tradesperson as a minimum and made operational in a Professional Manner to meet Local Government Standards
3.4.4 Supply Costs
   Once the Rainwater Implementation Category is started, a Table of Costs will be created. This table once created, will be the ongoing Record of Costs associated with Rainwater System
   a. Supply Cost, which means—at the time of report shall be the total of the ongoing Record of Costs amortised over the Volume of Used Rainwater for the Period of Report.
   b. Mains Delivery, which means—at the time of report, the cost of Mains Water Delivered amortised over the volume delivered for the Period of Report according to the Last Account. That Per Liter Cost used to calculate against the Volume of Mains Water Delivered for the Period of Report.
3.4.5 Rainwater Usage
   i. User Usage—is assigned through Assign User function used in conjunction with Usage Monitoring
   ii. Usage Monitoring—as measured through—
      a. Source Usage Detection via fitted Digital Flow Rate Sensor/Meter (17) at Water Storage System Tank feed (18)
      And/or
      b. Appliance Usage Detection via hard wired feed direct from Set Locations
      And/or
      c. Portable Usage/User/Function Timer/s
3.5 2nd Alt. Water Generate/Capture (Gen/Cap):
3.5.1 Overview
   This Section is designed for the Home using or intends installing a commercially available Water Gen/Cap system that is plumbed to the household as either Primary or Secondary Supply of Water with Digital Flow Rate Sensor/s/Meter/s installed and tested according to System Specifications capable of feeding data back to System
3.5.2 (Gen/Cap) and Delivery
   Unless the Gen/Cap Water System requires its own Self Contained Storage System Tank, the Gen/Cap Water System will deliver its water to the Common Household Storage System Tank. From the Household Storage System Tank, water will then be delivered to Appliances and other Outlet/s.
3.5.3 Implementation
   Components to be installed—
   i. Gen/Cap System (7) Complete Piping; Channel Plumbing and Plumbing Fittings
   ii. Digital Flow Rate Sensor/Meter (8)

iii. Water Storage System Tank (Self Contained) including Water Level Gauge

To be installed by Local Standards Graded Tradesperson as a minimum and made operational in a Professional Manner to meet Local Government Standards 3.5.4 Supply Costs Once the Gen/Cap Implementation Category is started, a Table of Costs will be created. This table once created, will be the ongoing Record of Costs associated with Gen/Cap System a. Supply Cost, which means—at the time of report shall be the total of the ongoing Record of Costs amortised over the Volume of Used Gen/Cap Water for the Period of Report.

b. Mains Delivery, which means—at the time of report, the cost of Mains Water Delivered amortised over the volume delivered for the Period of Report according to the Last Account. That Per Liter Cost used to calculate against the Volume of Mains Water Delivered for the Period of Report.

3.5.5 Gen/Cap Water Usage i. User Usage—is assigned through Assign User function used in conjunction with Usage Monitoring ii. Usage Monitoring—as measured through— a. Source Usage Detection via fitted Digital Flow Rate Sensor/Meter (8) at— i. Self Contained Water Storage System or ii. Common Household Storage System Tank feed (18)

b. Appliance Usage Detection via fitted Digital Water Flow Rate Sensors/Meters at Appliances (Schematic Location) and/or Outlet/s c. Portable Usage/User/Function Timer/s 3.6 Solar Hot Water:

3.6.1 Overview

This Section is designed for the Home using or intends installing a commercially available Solar Hot Water system that is plumbed to the household as either Primary or Secondary Supply of Hot Water with Digital Flow Rate Sensor/s/Meter/s installed and tested according to System Specifications capable of feeding data back to System 3.6.2 Generate and Deliver Solar Hot Water Cells will generate Hot Water from sunlight and deliver Hot Water (9) to Appliances and/or Outlet/s 3.6.3 Implementation Components to be installed— i. Solar Hot Water Cells (9)

ii. Complete Piping and Plumbing Fittings iii. Digital Flow Rate Sensors/Meters iv. Switch Watch (where fitted)

v. Electronic Temperature Gauge (where fitted)

To be installed by Local Standards Graded Tradesperson as a minimum and made operational in a Professional Manner to meet Local Government Standards The Solar Hot Water (SHW) Management System will remain independently responsible for Management of the Solar Hot Water with System monitoring the Solar Hot Water Management System where integration has been possible.

3.6.4 Supply Costs

Once the Solar Hot Water Implementation Category is started, a Table of Costs will be made available. This table once started, will be the ongoing Record of Costs associated with the Solar Hot Water System 3.6.5 Switch Watch, which means—the hot water delivery can be switched from solar generated to conventional gas or electrically heated at user selection or in the case of Temperature Watch (Sec. 3.6.6) where fitted, may switch automatically (Levels pre-set within System Set-up)

3.6.6 Temperature Watch, which means—the Solar Hot Water System (9) Electronic Temperature Gauge (where fitted) will deliver constant Current R/T Temperature readings.

i. The System will constantly monitor the Current R/T Temperature and capture at five (5) minute intervals—Date/Time Logged 3.6.7 Solar Hot Water Usage i. User Usage—is assigned through Assign User function used in conjunction with Usage Monitoring ii. Usage Monitoring—as measured through— a. Source Usage Detection via fitted Digital Flow Rate Sensor/Meter (17) at Solar Hot Water System (9)

b. Appliance Usage Detection via fitted Digital Water Flow Rate Sensors/Meters at Appliances (Schematic Location) and/or Outlet/s c. Portable Usage/User/Function Timer/s 3.7 Greywater:

3.7.1 Overview

This Section is designed for the Home presently using or plans installing a commercially available Greywater Capture and Treatment System that is plumbed to the household by local standards graded tradesperson as a minimum. To be monitored, using non-specific digital flow rate sensor/s/meter/s and digital volume level gauge/s installed and tested according to RMS System Specifications capable of feeding data back to The System.

3.7.2 Generate and Deliver

This Section will deliver Greywater drained directly from the Domestic Cloths Washing and Bathing Facilities. The system will maintain its own Internal Storage and Treatment Tank from which the Greywater will be delivered directly from, to the Required Usage Outlet/s 3.7.3 Implementation Components to be installed— i. Greywater Capture and Treatment System (23)

ii. Treatment Tank (23) (self contained)

iii. Digital Flow Rate Sensor/Meter (25)

To be installed by Local Standards Graded Tradesperson as a minimum and made operational in a Professional Manner to meet Local Government Standards The Greywater (GW) Management System will remain independently responsible for management of the Greywater with The System monitoring the GW Management System where integration has been possible 3.7.4 Supply Costs Once the Greywater Implementation Category is started, a Table of Costs will be made available. This table once started, will be the ongoing Record of Costs associated with the Greywater System 3.7.5 Greywater Usage
  i. User Usage—will not be monitored
  ii. Usage Monitoring as measured through—
    a. Appliance Usage Detection via fitted Digital Water Flow Rate Sensors/Meters at Appliances (Schematic Location) and/or Outlet/s
3.8 Water Buy Rates:
  Acquisition of Mains Water Buy Rates, which means—when the system needs to report on Current Mains Water Buy Rates it will source upto date Buy Rates from Mains Water Provider Web Portal Interface (46) depending on availability via Provider
3.9 Module Reporting:
  All Reports are Date/Time Logged
  System will Report on—
  3.9.1 Mains Water
    i. Mains Water Delivered—Source Usage Detection
    ii. Mains Water Used—Appliance Usage Detection
    iii. Current Mains Water Delivered R/T
    iv. Current Usage—R/T
    v. Hot Water Appliances Usage
    vi. Acquisition of Mains Water Buy Rates via Network Rotor/Internet Modem (76) to Mains Water Provider Web Portal (46) and account access
    vii. User Usage
    viii. Cost—Mains Power Heated & Usage vs Solar Hot Water Supply Costs (if installed)
    ix. Water & Appliances Usage
    x. Mains Water & Appliance Usage Costing
    xi. Validation of Usage against Delivered via—
      a. Source Usage Detection
      b. Appliance Usage Detection
    xii. Validation of Mains Provider Billing vs Provider Delivered
  3.9.2 Rainwater
    i. Rainwater Cost/Return Analysis
    ii. Current Rainwater Stored and Available R/T
    iii. Volume of Water Incoming & Outgoing to and from Rainwater Storage System Tank
    iv. Cost—Rainwater vs Mains Delivered
    v. % Mains Water Savings R/T & Historical
    vi. Rainwater Levels Held
      a. Current—R/T
      b. Pre-set—Date/Time
  3.9.3 Solar Hot Water
    i. Solar Hot Water Cost/Return Analysis
    ii. Solar Hot Water Cell Temperature Levels
      a. Current—R/T
      b. Historic—Nominated
    iii. Volume of Water Incoming & Delivered to and from Solar Hot Water System
    iv. Hot Water Usage at Digital Flow Rate Sensors/Meters
    v. Hot Water Appliances Usage
    vi. Appliance Usage Costing
    vii. User Usage
  3.9.4 Greywater
    i. Cost—Greywater Supply Costs vs Mains Water Delivered
  3.9.5 User Usage
    i. Mains Usage
    ii. Rainwater Usage
    iii. Hot Water Usage
    iv. Greywater Usage
    v. Appliance Usage
    vi. Total Water Usage—excluding Greywater
  3.9.6 Appliance Premium Usage Planning (PUP) against Mains Buy Rate—
    i. Efficiency recommendations
  The extent of System Functionality and Effectiveness within a household environment will always depend on—
    The level of Meter and Sensor Equipment integration with the System
    The commitment and physical interaction Household Users of the System apply to the ongoing and regular use of the System. The more User interaction applied to the System, the better the return of quality and worthwhile information by the System 4.0 Household Gas Management
Module Overview:
  The Household Gas Management Module is specifically designed to be an aid in assisting Users to achieve and maintain more economic and predictable overall gas usage.
  With good Usage and Appliance Monitoring integration, the System allows Users to also understand better what areas of their individual and household lifestyle uses the gas resource. For those households storing LPG via $3^{RD}$ Party Storage Systems, the System provides a means to also oversee the Management of such systems depending on the integration capabilities provided by the $3^{rd}$ Party System.
Module Functionality—
4.1 User Log-in:
  User Log-in for General Module Access is only necessary if User Is NOT logging into the main system
  User Log-in provides—
    i. Records Access
    ii. User Recognition—Date/Time Logged
    iii. Source Usage by User—Date/Time Logged
    iv. Appliance Usage by User—Date/Time Logged
    v. Timed Usage—Date/Time Logged
4.2 Gas Usage:
  Gas Usage—as measured through—
  4.2.1 User Usage—as assigned through Assign User function used in conjunction with Usage Monitoring will Capture—
    i. Current User Usage in Real-Time
    ii. Total Historical User Usage
    iii. Current Appliance/User Usage in Real-Time
    iv. Total Historical Appliance/User Usage
  4.2.2 Usage Monitoring—as measured through—
    i. Source Usage Detection, which means—when the System detects Usage (Levels pre-set within System Set-up) via hard wired feed direct from fitted Digital Gas Flow Rate Sensors/Meters System (Schematic Location) where installed at Source
    ii. Appliance Usage Detection, which means—System detects Extra Gas Usage (Levels pre-set within System Set-up) via hard wired feed direct from fitted Digital Gas Flow Rate Sensors/Meters at Appliances (Schematic Location/s) and/or Outlet/s
      All fitted Digital Gas Flow Rate Sensors/Meters must carry a Unique Digital ID Signal Code, which is Logged to System for Specific Function/s and/or Outlet/s
    iii. Portable Usage/User/Function Timer (21), which means—timers that are specifically designed and are hard wired or Bluetooth feed direct from specific function location and Manually Operated by the User undergoing a Selected Function using a Selected Appliance
      Usage of Portable Usage/User/Function Timers is Manually Calibrated to an Estimated Volume of Gas Usage per/second per/valve clearance against each Selected Appliance/Outlet iv. Timed Usage, which means as Usage Detection triggers System, the Usage Timer will be triggered and run until Usage is detected to stop. The Usage Time will be logged against the Appliance or Source it has been triggered by and User.

4.2.3 Gas Leakage Recognition as identified through—
  i. Volume Calculation under pre-set Source and Appliance Usage levels Once alerted to the Gas Leakage, the System will display a Flashing Pop-up Alert Warning GAS LEAK FOUND and sub-texted with a pre-determined recommendation message.

4.3 Mains Gas:
  4.3.1 Mains Gas Usage (30)—as measured through—
    i. Source Usage Detection via hard wired feed direct from Gas Provider's In-house Digital Gas Meter System (31) (where installed)—
    And/or
    ii. Appliance Usage Detection via hard wired feed direct from Set Locations
    And/or
    iii. Portable Usage/User/Function Timer/s
  4.3.2 Monitor Current Mains Gas Delivered Real-Time Feed (R/T) via Source Usage Detection 4.4 LP Gas:
  4.4.1 Overview
    This Section is designed for the Home using or intends installing a commercially available LP Gas system that is plumbed to the household as either Primary or Secondary Supply of Gas with Digital Flow Rate Sensor/s/Meter/s installed and tested according to System Specifications capable of feeding data back to System
  4.4.2 Storage and Delivery
    LP Gas Storage System Tank will hold LP Gas from where water will then deliver to Appliances and other Outlet's
  4.4.3 Implementation
    Components to be installed—
    i. Digital Flow Rate Sensors/Meters
    ii. LP Gas Storage System Tank (34) including Digital Gas Level Gauge (35)
      To be installed by Local Standards Graded Tradesperson as a minimum and made operational in a Professional Manner to meet Local Government Standards
  4.4.4 Supply Costs—
    Once the LP Gas Implementation Category is started, a Table of Costs will be made available. This table once started, will be the ongoing Record of Costs associated with the LP Gas System
    i. Supply Cost means—at the time of report, shall be the total of the ongoing Record of Costs amortised over the Volume of Used LP Gas for the Period of Report.
  4.4.5 LP Gas Usage
    i. User Usage—is assigned through Assign User function used in conjunction with Usage Monitoring
    ii. Usage Monitoring—as measured through—
      a. Source Usage Detection via fitted Digital Flow Rate Sensor/Meter (32) at LP Gas Storage System Tank feed (34)
      And/or
      b. Appliance Usage Detection via hard wired feed direct from Set Locations
      And/or
      c. Portable Usage/User/Function Timer/s 4.5 LP Gas Buy Rates:
  Acquisition of Mains Gas/LPG Buy Rates which means—When the system needs to report on Current Mains Gas Buy Rates it will source upto date Buy Rates from the Providers Interface (28) or Providers Web Portal (29) depending on availability 4.6 Module Reporting:
  All Reports are Date/Time Logged
  System will Report on—
  4.6.1 Mains Gas
    The System will Report on—
    i. Mains Gas Delivered—Source Usage Detection—Date/Time logged
    ii. Monitor Current Mains Gas Delivered R/T
    iii. Monitor Current Gas Usage R/T
    iv. Acquisition of Mains Gas Buy Rates via Network Rotor/Internet Modem (76) to Mains Gas Provider Web Portal (46) and account access
    v. Gas & Appliances Usage—Date/Time logged
    vi. Validation of Usage against Delivered
    vii. Delivered at Gas Provider's In-house Digital Gas Meter System
    viii. Validation of Mains Provider Billing against Provider Delivered
    ix. Gas & Appliance Usage Costing—Date/Time logged
  4.6.2 LPG
    i. LPG Cost/Return Analysis (if installed)
    ii. Monitor Current LPG Delivered R/T
    iii. LPG Tank Storage Facility/Maintenance Schedule (If installed)
      a. Existing Storage Level & Actual Volume of LPG Held/Delivered—Date/Time of Request & Pre-set Date/Time—logged
    iv. Delivered vs Usage Validation
  4.6.3 User Usage
    i. Mains Usage
    ii. LPG Usage
    iii. Appliance Usage
    iv. Total Gas Usage
  4.6.4 Appliance Premium Usage Planning (PUP) against Mains Buy Rate—
    Efficiency recommendations
  The extent of System Functionality and Effectiveness within a household environment will always depend on—
    The level of Meter and Sensor Equipment integration with the System
    The commitment and physical interaction Household Users of the System apply to the ongoing and regular use of the System. The more User interaction applied to the System, the better the return of quality and worthwhile information by the System 5.0 Contacts & Diaries:
Module Overview:
  The Contacts & Diaries Module provides Users with the means to keep accurate records of Personal and Shared Household Contacts also providing the ability to manage Personal. Healthcare, Shared Household and Business Activities through Personal and/or Common Diaries.
  With good systems hardware integration, the System also provides the ability to Identify; Register; Track and Record details for Incoming Telecommunication Calls and to Dial On Command; Register; Track and Record details for Outgoing Calls.

Module Functionality—
5.1 User Log-in:
User Log-in for General Module Access is only necessary if User Is NOT logging into the main system
User Log-in provides—
  i. Records Access
  ii. User Recognition—Date/Time Logged
  iii. User Contacts and Interaction—Date/Time Logged
  iv. User Diaries and Interaction: std Personal/PHR Diary; Business Diary and Household—Date/Time Logged
  v. Synchronisation to HHP device (60)—Date/Time Logged
5.2 User & Household Contacts
All Functionality available on HHP device (60)
  5.2.1 Referred Contacts—Means if the User receives a MS Outlook Contact, The System will import this Contact's Details and request of The User that Contact Class be nominated.
  5.2.2 User & Household Contact Classes—Record and Management of Household classified and individually classified and Maintained Contacts.
    i. Class 1 (C1)—HCP (HealthCare Providers)—Contacts listed as Medical and Health Providers to the Individual User can be Assigned/Referred to another User within the Household (Main) system though will only assign/refer basic Contact Details. A Full Contact History and Associated Attachments will be retained only within the referring User's Contacts and Diary Records as they are retained as "Class 1—HCP" records.
      a. Class 1 Contacts and any Activities pertaining to or associated with Class 1 Contacts will become and remain part of the User/Patient Personal Health Records (PHR)
      b. If User has Dependant Child PHR File attached, (as referred to in 1.0/Main Sys/b)/ii)/a)/ii)), C1 Contacts are also Associated to that specific Dependant Child PHR File
        Class 1 Contacts require a Provider Number that is obtained from the HealthCare Provider
    ii. Class 2 (C2)—Contacts held within the Household Contact List and can be common to each Individual User within the Household holding a Full Contact History and Associated Attachments.
    iii. Class 3 (C3)—Contacts held by a specific User within the Household (Main) system holding a Full Contact History and Attachments.
    iv. Class 4 (C4)—Contacts held by a specific User within the Household holding a Full Contact History and Attachments—May have a limitation.
5.3 Auto Dialed Outbound Calls can be made to Contacts selected within the system by the user via Telecommunications Modem (51) Connection where available
Outbound Call History will be kept against All Contacts within the System and available for anytime view by the User whom the Contact belongs to
Please note, User/s must be Logged-in to the System to Activate User Specific Contact and Diary System and all System Functionality—If User/s not Logged-in, Outbound Calls will be Independent of System Contacts and Diary Functionality
5.4 Caller ID Recognition for Inbound Calls will ID the source number of calls made to the Household (Main) System using what is defined as Caller ID Recognition through Telecommunications Provider Caller ID where available and Caller provides Phone Number ID available
Inbound Call History will be kept against All Contacts within the System and available for anytime view by the User whom the Contact belongs to
Please note, User/s must be Logged-in to the System to Activate User Specific Contact and Diary System and all System Functionality—If User/s not Logged-in, Inbound Calls will be Independent of System Contacts and Diary Functionality
  5.4.1 When Caller ID is Provided—System will Search Contact Records for Identified Number
    i. If Contact Record Found—System will create Call Received Pop-up Showing "User Name" of whom the ID In-Coming Caller belongs within the System; Caller/Contact Name of Identified Number—with Call Reason Field to record any information by User
    ii. If Contact Record Not Found—If Option Pre-set, System will provide Optional New Contact Pop-up to Record Contact Details—Name; User; Company; Address; Phone Numbers; Emails
5.5 The User Diary will maintain a Complete Diary of any User Activities also with a History maintained against any User Contacts within the Contacts and User Diary Module associated with that Activity
All Functionality available on HHP device (60)
  5.5.1 The Activity Planner as outlined in eVLB module allows the user to plan any Individual Activity and to also create Default Activities, which can then be selected from a drop-down list each with preset default factors applied including Exercise that will apply default factors from the Healthcare Management Module (Personal Health Records)—Exercise Management (sec. 12.10) if the module is used by the User creating the Activity in which case the Exercise components of the Activity will become part of the User PHR.
  5.5.2 Vehicle Scheduling Diary (VSD) as outlined in eVLB—If a vehicle has Multiple Users, it can also carry its own Vehicle Scheduling Diary (VSD). This VSD will be directly Associated to the Vehicle Specific eVLB and be Synchronised simultaneously with All Other eVLB Records. Any Associated Vehicle User can create a Vehicle Booking for the Specific Vehicle within the VSD. This Booking will then require Booking Approval by the Vehicle Administrator, which will then Schedule the Vehicle Booking within the VSD. This Booking Approval will be requested and can be answered via the System.
    a. If approved by the Vehicle Administrator, the Vehicle Booking will be highlighted as an Approved Booking in both VSD and Booking User Diary—If Booking User holds more than one Diary, Diary selection takes place at time of Booking.
    b. If not approved by the Vehicle Administrator, the Vehicle Booking will be highlighted as an Un-Approved Booking in both the VSD and Booking User Diary.
      At time of Approval Request, the Vehicle Administrator then has the option of—
        i. Creating a Vehicle Booking under their own name or another Associated User.
        ii. Creating a Waiting List with the Requesting User as No. 1 including option of adding other Associated Users.
  5.5.3 Travel Planner as outlined in eVLB module, allows User to add/create details such as Travel Destination; Projected and/or Expected Travel & Sundry Costs (Public or Private Transport inc. Vehicle Allocation via Vehicle Scheduling Diary) and Costs to a New or Existing Vehicle Allocation Entry via Vehicle Scheduling Diary; User Personal and/or Business Diary by—
i. Creating New Details
or
ii. Recalling Existing Details from a Previous or Coming Activity 5.5.4 Fuel Cost Planner as outlined in eVLB module, allows User to add/create Fuel Costs to a New or Existing Diary Activity/Vehicle Allocation Entry by Estimation or by triggering Distance Plotter 5.5.5 Distance Plotter as outlined in eVLB module, is triggered from within either—
i. The Fuel Cost Planner as the next step to complete Fuel Cost Planning
or
ii. Any Activity as a component of planning process Distance Plotter will calculate distances using—
a. "Google Maps" by selecting button where internet access available
or
b. Other $3^{rd}$ party systems available by selecting button where internet access available
iii. Manually Enter Address into Google Maps or other Address Field
or
iv. Select from Contact List will populate the Google Map or other Address Field with Existing Address
v. System will calculate Distance to be Traveled then by request, against a specific Motor Vehicle included in Vehicle Scheduling Diary and Associated to User using Current Mileage 5.5.6 Conventional Vehicle Projected Mileage to as outlined in eVLB module, Purchase Fuel providing the means to project the mileage based on Historical/Current Mileage 5.5.7 Hybrid or Electric Vehicle Projected Mileage to as outlined in eVLB module, Purchase Fuel and/or Plan Battery Charges providing the means to project the mileage based on Historical/Current Mileage 5.5.8 Projected Costs Including Motor Vehicle Service Costs as outlined in eVLB module, which are calculated from existing Specific Vehicle History and amortised over the projected distance the Specific Vehicle is likely to drive for the period nominated for the calculation 5.5.9 Road and Driving Conditions as outlined in eVLB module, will estimate Travel Time based on Expected Road, Weather and Traffic Conditions plus Expected Average Speed 5.5.10 Fuel Type Price Variance/Value Threshold calculates the different consumption rates of different Fuel Octane Level Types, which will vary from vehicle to vehicle. With the different Consumption Levels recorded against the different Mileages, the system calculates a Variance/Value Threshold.

5.6 SMS Contact Messaging where available through Telecommunications Provider. System allows User the ability to enter and send SMS and MMS Messages to Contacts within System with recorded mobile phone numbers and active mobile phones 5.7 Synchronise the Main System with M/APPs' creates the Synchronisation of any Existing User Diary Main System and M/APP data. Once HHP connected via standard Access Method, The System will confirm you are ready to Synchronise both Systems
If PHR's are to be Merging, Transfer and/or Synchronisation, User/Patient is then asked to confirm Merging, Transfer and/or Synchronisation with their PHR Validation Log-in (secondary) PHR Validation Code
i. Once Approved, System will Synchronise
ii. System will Alert when Synchronisation Complete
iii. Disconnect HHP device
iv. Disconnection Registered 5.8 Module Reporting
All Reports are Date/Time Logged
The System will Report on—
5.8.1 Contacts
i. User Contacts Total/Classes
ii. Household Contacts
iii. Contact Activities
5.8.2 Diary
i. User Diaries
ii. User Activities
iii. Household Diary
iv. Household Activities
5.8.3 Calls Made
i. User Call Tracking, which means Calls Made by User can be Tracked to—
a. Number made to each Contact
b. Date/s and Time/s Made
ii. User Call History, which means Calls Made by User will have a History of Contact/s Call/s Made To & showing—
a. Reason/s for Call/s
b. Follow-up Action/s Required & Taken 6.0 Household Accounts
Module Overview:
The Household Accounts Management Module provides the User with the ability to create Accounts and Sub-accounts to represent Expenses; Income; various Credit Accounts such as Superannuation; Investments; Savings Accounts various Debit Accounts such as Credit Cards; Loans and Mortgages and also ATM Transactions. The Accounts Management module then allows the recording of Personal and Family Financial Account Transactions within such accounts all with Web Portal Interface capability. The system also provides Statements and Reconciliations for each Account and Sub-account.
This functionality is subject to the level of system integration provided by each Financial Institution Module Functionality—
6.1 User Log-in
User Log-in—User Must Be already Logged-In to the Main System
6.1.1 Module Log-in—User selects Household Accounts Icon—logs User into Household Accounts module with their personal System Profile (User name) and Password
User Log-in provides—
i. Records Access
ii. User Recognition—Date/Time Logged
iii. All Functionality—Date/Time Logged 6.2 Create Account/s
Create Account/s provides the User with the ability to create an Account or Sub-account for the following—
6.2.1 Income—Multiple possible
6.2.2 Expense—Multiple possible
6.2.3 Credit—Multiple possible
6.2.4 Debit—Multiple possible 6.3 Account Transaction Synchronizing
Account Transaction Synchronizing provides Users with the ability to Synchronise all Account and Sub-account Transactions with Mobile Accounts.

This functionality is only available to Users within the Main Household System 6.4 Web Portal Account Synchronisation Web Portal Account Synchronisation provides Users with the ability to Synchronise all Account and Sub-account Transactions.

This functionality is subject to the level of system integration provided by each Financial Institution 6.4.1 User Log-in—User Must Be already Logged-in to Household Accounts 6.4.2 Function Activation—User selects Web Portal Specific Institution Icon—logs User into the Financial Institution Account via Web Portal Interface (80) from Household Account System with their personal Financial Institution Account System Profile (User name) and Password 6.4.3 User is then asked to Log-in using their Mobile Accounts' Validation Log-in (secondary) Mobile Accounts' Validation Code Although not recommended, this can be made unnecessary if preferred 6.4.4 User specific account details now available for Synchronisation 6.4.5 Log Off discontinues any Synchronisation and disconnects Web Portal session 6.5 System Account Statements and Reconciliations System Account Statements and Reconciliations provides Users with the ability to create—
 i. Period Account Statements
 ii. Account Reconciliations 6.6 Module Reporting All Reports are Date/Time Logged System will report on—
 i. All Existing Accounts/Account Numbers 7.0 Security Module Overview:

The Security Module provides Users with the means to Overview/Report on the 3rd Party Household Security System and $3^{rd}$ Party Motor Vehicle Remote Security systems Module Functionality—

7.1 Household Security

This functionality is subject to each $3^{rd}$ Party Household Alarm matching the defined Security Interface
 i. Operational Control
 ii. User Recognition 7.2 Motor Vehicle Remote Security This functionality is subject to each $3^{rd}$ Party Motor Vehicles Systems matching the defined Security Interface
 i. Security Current Status
 ii. Control of Motor Vehicle Remote Security via Web Portal 7.3 Web Portal System Access Web Portal to Integrate with $3^{rd}$ Party Household Alarm System and $3^{rd}$ Part Motor Vehicle Alarm System—This will be done via a pre-set Web Portal Icons configured to only call up and log onto pre-set $3^{rd}$ Party Household Alarm System and $3^{rd}$ Party Motor Vehicle Alarm System Web Portals.

This functionality is subject to each $3^{rd}$ Party Household Alarm and $3^{rd}$ Part Motor Vehicles Systems matching the defined Security Interface This functionality can't be Triggered from outside the HHP Security System/Module and may require a secondary security login This functionality requires direct Internet Access 7.3.1 User Log-in—User Must Be already Logged-in to Security Module 7.3.2 Function Activation—User selects Specific Household or Motor Vehicle Security module Icon—logs User into either Security Account via specific Security System Web Portal Interface (95) with their personal Security Account System Profile (User name) and Password 7.3.3 User is then asked to Log-in using their Mobile Securities' Validation Log-in (secondary) Mobile Accounts' Validation Code Although not recommended, this can be made unnecessary if preferred 7.3.4 User specific account details now available for Synchronisation 7.3.5 Log Off discontinues any Synchronisation and disconnects Web Portal session 7.4 Module Reporting All Reports are Date/Time Logged System will report on—

7.4.1 Household Security
 i. Report on Security Operational Hours
 ii. User Activations and De-activations 7.4.2 Motor Vehicle Remote Security
 i. Report on Security Operational Hours 8.0 Telecommunications Management Module Overview:

The Telecommunications Management Module provides Users with the means to keep accurate records of Personal and Shared Phone Usage.

With good systems hardware integration, the System also provides the ability to track and record details for Incoming also dialing, tracking and recording details for Outgoing Calls.

Module Functionality—

8.1 User Log-in:

User Log-in for General Module Access is only necessary if User is NOT logging into the Main System User Log-in provides—
 i. Records Access
 ii. User Recognition—Date/Time Logged
 iii. Timed Usage—Date/Time Logged Phone Usage:

Please note—User/s must be Logged-in to System to activate User Call Usage and Tracking; Specific Contact and Diary System and all System Functionality—If User/s Not Logged-in, all Outbound and Inbound Calls will be Independent of System Contacts and Diary Functionality 8.2 Call Functionality:

8.3 Inbound and Outbound Call Functionality within the System is triggered by—

8.3.1 Call Triggered Automation for—
 i. Outbound Calls (Calls Made), which means Call has been activated from Contact Screen also triggering a Call Contact Pop-up activating a Call Timer and Requesting Call Purpose and Associated Notes
 ii. Inbound Calls (Calls received), which means as Caller ID is received, System will Trigger Contact Search Function with—
   Inbound Caller ID can be captured and logged using Caller ID where and when made available through the Telecommunications Provider
   a. It Contact Record Found—System will create Call Received Pop-up showing "User Name" of whom the ID In-Coming Caller belongs within the System; Caller/Contact Name of Identified Number—with Call Reason Field to record any information by User
b. if Contact Record Not Found—If Option Preset, System will provide Optional New Contact Pop-up to record Contact Details—Name; User; Company, Address; Phone Numbers; Emails
or
iii. Call Button Activation, which is a button set in User Interface and triggered by User to activate the Call Timer fir both Outbound and Inbound Calls
a. Outbound Calls are triggered by Call Activation Button set in Front Contact Screen
b. Inbound Calls are triggered by Call Activation Button set into each System Screen 8.4 Call Function Integration:
i. Both Outbound and Inbound Call Functionality is only available where the Phone System Equipment (52) is connected via Phone/Telecommunications Modem (51) to the System's Computer Hardware and is correctly configured within the Computer Operating System 8.5 Outbound Call:
8.5.1 User Call Usage, which means All Calls Made by User showing—
i. Number Of Calls Made
ii. Dates Calls Made
8.5.2 Individual User Usage breakdown
8.5.3 User Usage Logs available
8.5.4 History Tracking, which means an Outbound Call History will be kept against All Contacts within the System and available for anytime view by the User whom the Contact belongs to 8.6 Inbound Calls:
8.6.1 Individual User Usage breakdown
8.6.2 User Usage Logs available
8.6.3 History Tracking, which means an Inbound Call History will be kept against All Contacts within the System and available for anytime view by the User whom the Contact belongs to 8.7 Call Rates:
Acquisition of Call Rates, which means—when the system needs to report on Current Call Rates it will source up to date Call Rates from Telecommunications Provider Web Portal Interface (55) depending on availability via Provider 8.8 Billing:
Billing will be made available for all internal household purposes including
i. Validation of Telecommunications Provider Billing vs Usage Logs
When System needs to report on Current Provider Billing, it will source Current Billing from Telecommunications Provider Web Portal Interface (55) depending on availability via Provider
ii. Split Billing Reporting
iii. Split Bill Payments where Providers makes available 8.9 Module Reporting:
All Reports are Date/Time Logged
System will report on—
8.9.1 Phone Usage
i. Total Usage via—
a. Triggered Automation
b. Call Button Activation
ii. User Call Usage via—
a. Triggered Automation
b. Call Button Activation
iii. User Call Tracking via—
a. Triggered Automation
b. Call Button Activation
iv. User Call History via—
a. Triggered Automation
b. Call Button Activation
v. Validation of Usage against Billed via—
a. Total Usage
b. Telecommunications Provider Billing The extent of System Functionality and Effectiveness within a household environment will always depend on—
The Phone System Equipment integration with the System's Computer Hardware
The commitment and physical interaction Household Users of the System apply to the ongoing and regular use of the System. The more User interaction applied to the System, the better the return of quality and worthwhile information by the System 9.0 Internet Access
Module Overview:
The Internet Access Module provides Users with the means to keep accurate records of Personal and Shared Internet Access and Usage.
Module Functionality—
9.1 User Log-in:
User Log-in for General Module Access is only necessary if User is NOT logging into the Main System
User Log-in provides—
i. Internet Usage Monitoring
ii. User Recognition—Date/Time Logged
iii. Usage Detection—Date/Time Logged Internet Usage:
Please Note—Internet Usage Functionality is triggered by—
i. Internet Usage Monitoring is only available when User selects "Internet Log-In" from within the System
or
ii. Internet Usage Button Activation, which is a button set in User Interface triggered by User to activate the Internet Access Timer 9.2 Internet Usage:
Internet Usage will be captured and logged where Users are Logged-in
i. Total Usage will be made available for all internal household purposes
ii. Individual User Usage breakdown
iii. User Usage Logs available
iv. History Tracking 9.3 Billing:
Billing will be made available for all internal household purposes including
9.3.1 Split Billing Reporting
9.3.2 Split Bill Payments will be calculated for household purposes only 9.4 Reporting:
All Reports are Date/Time Logged
Reports will be made available for all internal household purposes 10.0 Intelligence For Fun (I-4-Fun)
Module Overview:
This will be an ever-changing module based on Current Teaching and Learning Trends. Although the Module Name and Concept of including a fun interactive family and teaching game module is certainly part of the System and therefore covered by IP and included as part of this current patent application, the games themselves will not be components of this current patent application due to their ongoing change. It may be that the games used may be integrated $3^{Rd}$ Party provided and if necessary, each game developed, may undergo a separate patent application.

Module Functionality—

10.1 User Log-in:
  User Log-in for General Module Access is only necessary if User Is NOT logging into the main system
  User Log-in provides—
    i. Records Access
    ii. User Recognition—Date/Time Logged 10.2 Module Usage:
  Module Usage—as measured through—
    10.2.1 User Usage as assigned through Assign User function used in conjunction with Usage Monitoring will Capture—
      i. Current User Usage in Real-Time
      ii. Total Historical Game User Usage
      iii. Current Game/User Usage in Real-Time 10.3 Chess Challenge, which means an Electronic Chess Game that offers the ability to—
  10.3.1 User play another Opponent
  10.3.2 User play the Computer 10.4 Krazy Teacher
  10.4.1 Yet to be specified 10.5 Family Fun
  10.5.1 Yet to be specified Consider different levels of entertainment interaction with Interaction and Content based on Age Bands for example:
  i. Pre School
  ii. Primary—K to Y6
  iii. Secondary—Y7 to Y12
  iv. Adult-Band 1
  v. Adult—Band 2
  vi. Adult—Band 3
  vii. Family—This band would be made up of General, contributed to by the member's Band involved by Nomination. Example: Primary; Secondary; Adult—B1; B2; B3
  viii. Group—This band would be made up of General, contributed to by the member's Band involved by Nomination. This maybe a different style based on the likelihood of a One Off principal rather than a potential of Re-occurrence. Example: Secondary; Adult—B1; B2; B3
  Each Band would contribute to what Interaction and Content is made available.
  This will likely be an On-line Updated model 10.6 Health Condition Specific Integration Interface
  10.6.1 For example, interface to applications that are Condition Specific such as Autism and other Specific Learning Conditions
  Interaction within this module section can be also recorded against PHR 11.0 Electronic Vehicle Log Book: (eVLB)
Module Overview:
  The Electronic Vehicle Log Book (eVLB) within the System is an Electronic Log of all Use and History of Specific Motor Vehicles.
  The eVLB is a stand alone file that is designed to be a Fixed Electronic Record of the Specific Vehicle's Ongoing History. At the time the file is commenced, the file set-up will require a Vehicle Identification Number/Chassis Number (VIN/CN) from which the System will create a Unique Electronic Signature that can't be changed and will remain perpetually assigned to the VIN/CN.

This eVLB can be a multi-user eVLB or a single user eVLB. The Registered Owner of the Motor Vehicle is set-up as Vehicle Administrator of the Vehicle Specific eVLB and has Administrative Rights over that Vehicle Specific eVLB. The Vehicle Administrator can Associate and Un-associate any Resident/User to their Vehicle's eVLB as a Vehicle User. Each Associated Vehicle User within the Household/Main System has access to their Personal Version of the Vehicle Specific eVLB inc. Vehicle Scheduling Diary (VSD) if provided by and at the discretion of Vehicle Administrator. Each Personal Vehicle Specific eVLB is Synchronised with the Main System with All Vehicle History accessible through each Personal Vehicle Specific eVLB and by all Vehicle Users through the Main System eVLB.

Module Functionality—

11.1 User Log-in:
  User Log-in for General Module Access is only necessary if User is NOT logging into the main system
  User Log-in provides—
    i. Records Access
    ii. User Recognition—Date/Time Logged
    iii. Approved eVLB Access—Date/Time Logged
    iv. Synchronisation to HHP device—Date/Time Logged 11.2 Create eVLB:
  Create eVLB provides the Registered Owner (Vehicle Administrator) of a Vehicle the ability to—
    11.2.1 Create an eVLB, which provides the means for the Registered Owner (Vehicle Administrator) of a Vehicle to—
      a. Capture and log their specific use of the Specific Motor Vehicle into an Electronic Vehicle Log Book format. The eVLB is a stand alone file that is a Fixed Electronic Record of the Vehicle's Ongoing History.
      b. At the time the file is commenced, file set-up will require a Vehicle Identification Number/Chassis Number (VIN/CN) from which the System will create a Unique Electronic Signature, which can't be changed and will remain perpetually assigned to the VIN/CN.
      c. At the time the file is commenced, file set-up will require the Vehicle Administrator (Registered Owner) of the Vehicle, Motor Vehicle Drivers License number, which will be taken by default from the Main System. If the Vehicle Administrator does not have their Motor Vehicle Drivers License number registered in the Main System, the System will require this before commencing the file.
      d. Allocate User Rights of the eVLB for the purpose to View and/or Add to
        i. User Recognition/Notification—Date/Time/Kms Logged
        ii. Vehicle Scheduling Diary—View & Request
        iii. Fuel/Oil Purchases—Date/Time/Kms Logged
          An Allocated User of a Specific Vehicle may potentially hold this eVLB file on their individual HHP device 11.3 Vehicle Scheduling Diary (VSD):
  If a vehicle has Multiple Users, it can also carry its own Vehicle Scheduling Diary (VSD). This VSD will be directly Associated to the Vehicle Specific eVLB and be Synchronised simultaneously with All Other eVLB Records. Any Associated Vehicle User can create a Vehicle Booking for the Specific Vehicle within the VSD. This Booking will then require Booking Approval by the Vehicle Administrator, which will then Schedule the Vehicle Booking within the VSD. This Booking Approval will be requested and can be answered via the System.
  a. If approved by the Vehicle Administrator, the Vehicle Booking will be highlighted as an Approved Booking in both VSD and Booking User Diary—If Booking User holds more than one Diary, Diary selection takes place at time of Booking.
  b. If not approved by the Vehicle Administrator, the Vehicle Booking will be highlighted as an Un-Approved Booking in both the VSD and Booking User Diary.
    At time of Approval Request, the Vehicle Administrator then has the option of—
    i. Creating a Vehicle Booking under the Vehicle Administrator name or another Associated User.
    ii. Creating a Waiting List with the Requesting User as No. 1 including option of adding other Associated Users.

11.4 Travel Planner:
  Travel Planner allows User to add/create details such as Travel Destination; Projected and/or Expected Travel & Sundry Costs (Public or Private Transport inc. Vehicle Allocation via Vehicle Scheduling Diary) and Costs to a New or Existing Vehicle Allocation Entry via Vehicle Scheduling Diary; User Personal and/or Business Diary by—
    i. Creating New Vehicle Allocation Entry
    or
    ii. Recalling Existing Details from a Previous or Coming Vehicle Allocation Entry
  11.4.1 Fuel Cost Planner allows User to add/create Fuel Costs to a New or Existing Diary Activity/Vehicle Allocation Entry by Estimation or by triggering Distance Plotter
    The Fuel Cost per Liter can be entered either—
    i. Manually
    or
    ii. Selected via Fuel Watch (or equivalent) Web Portal Interface as described in Item—9.5 Update Fuel Prices
  11.4.2 Distance Plotter is triggered from within either—
    i. The Fuel Cost Planner as the next step to complete Fuel Cost Planning
    or
    ii. Any Vehicle Allocation Entry as a component of planning process Distance Plotter will calculate distances using—
      b. "Google Maps" by selecting button where internet access available
      or
      c. Other 3$^{rd}$ party systems available by selecting button where internet access available
    iii. Manually Enter Address into Google Maps or other Address Field
    or
    iv. Select from Contact List will populate the Google Map or other Address Field with Existing Address
    v. System will calculate Distance to be Traveled then by request, against a specific Motor Vehicle included in Vehicle Scheduling Diary and Associated to User using Current Mileage
  11.4.3 Conventional Vehicle Projected Mileage to Purchase Fuel providing the means to project the mileage based on Historical/Current Mileage
  11.4.4 Hybrid or Electric Vehicle Projected Mileage to Purchase Fuel and/or Plan Battery Charges providing the means to project the mileage based on Historical/Current Mileage
  11.4.5 Projected Costs Including Motor Vehicle Service Costs, which are calculated from existing Specific Vehicle History and amortised over the projected distance the Specific Vehicle is likely to drive for the period nominated for the calculation
  11.4.6 Road and Driving Conditions will estimate Travel Time based on Expected Road, Weather and Traffic Conditions plus Expected Average Speed
  11.4.7 Fuel Type Price Variance/Value Threshold calculates the different consumption rates of different Fuel Octane Level Types, which will vary from vehicle to vehicle. With the different Consumption Levels recorded against the different Mileages, the system calculates a Variance/Value Threshold.

11.5 Update Fuel Prices via 'Fuel Watch' (or equivalent) Web Portal Interface (71) using an Internet Connection
  11.5.1 Fuel Cost Planner in conjunction with 'Fuel Watch' (or equivalent) price monitoring & distance calculations via GPS (or estimation) to—
    i. A nominated number of Closest Fuel Stations (to System Residence; Present Location; other Nominated Location or Plotted Journey via Item—9.4.2 Distance Plotter)
    ii. To calculate the Fuel Cost vs Klm's to travel to identify the most Financially Worthwhile station to purchase fuel from based on—
      a. Distance
      b. Projected Fuel Consumption
      c. Monitor & Input (User Selection)—'Fuel Watch' (or equivalent) will need to capture Trading Hours and confirm Fuel Availability at Time of Report
  This section remains subject to confirmations with 'Fuel Watch' (or equivalent) that these Web Portal Interface functions are possible 11.6 Service and Maintenance Log:
  11.6.1 Motor Vehicle Servicing Program logs all Specific Vehicle Services and Costs into the Electronic Vehicle Log Book (eVLB) file.
    i. This is done by using the Vehicle Manufacturer's Prescribed Service Program as the template with alarms set to warn of upcoming Due Service including the Prescribed or Expected Costs.
    ii. The Alarms will also alert Vehicle Users of Pending Service Due falling during or near Planned Vehicle Usage logged as Activities within the Diary.
  11.6.2 Motor Vehicle Service Booking logs onto the Service Centre Management Information System (MIS) Web Portal Interface (70) using an Internet Connection.
    i. The system will Synchronise Specific Vehicle History with the Service Centre Management Information System and requests a Vehicle Service according to the next Due Service according to the Vehicle Manufacturer's Prescribed Service Program.
    ii. The Service Centre Management Information System will provide the Next Available Service Time according to the Time Prescribed for such a service.
    iii. The User will then be given the opportunity to Accept or Reject the Service Booking.
  11.6.3 Service Centre Synchronisation creates the Synchronisation of Specific Vehicle eVLB Service Data with the Service Centre Management Information System (MIS) (75).

11.7 Synchronise the Main System with M/APPs' creates the Synchronisation of any Existing Vehicle Specific eVLB Main System and M/APP data. Once HHP connected via standard Access Method, The System will confirm you are ready to Synchronise both Systems
   11.7.1 Once Approved, System will Synchronise
   11.7.2 System will Alert when Synchronisation Complete
   11.7.3 Disconnect HHP device
      i. Disconnection Registered
11.8 Module Reporting:
All Reports are Date/Time Logged
System will report on—
   11.8.1 eVLB
      i. Specific Vehicle Fuel/Oil Purchases
      ii. Total Vehicles Fuel/Oil Purchases
      iii. Specific Vehicle Current Mileage
      iv. Total Vehicles Current Mileage
   11.8.2 Vehicle Scheduling Diary
      i. Specific Vehicle Scheduled Diary
      ii. Total Vehicles Scheduled Diary
   11.8.3 Travel Planner
      i. User Planned Travel
      ii. Specific Vehicle Planned Travel
   11.8.4 Service and Maintenance Costing
      i. Previous Specific Vehicle Costs based on Historical Specific Period
      ii. Previous Total Vehicle Costs based on Historical Specific Period
      iii. Projected Specific Vehicle Costs based on Projected Mileage by either—
         a. Historical Specific Period Mileage
         b. Present Vehicle Allocation
   11.8.5 User Fuel/Oil Purchases
   11.8.6 Specific Vehicle Maintenance/Service Costs
   11.8.7 User/Specific Vehicle Maintenance/Service Costs
12.0 Healthcare Management (Personal Health Records)—Household/Main System
Module Overview:

The Healthcare Management Module is specifically designed to be an aid in assisting Users to achieve and maintain better overall Health management through better Healthcare Records from birth through to aged care.

This will include the various immunisation periods of early childhood and adolescent years; ongoing sporting injuries; seasonal infections; PBS medications; specific Healthcare Provider communications and record of exposure to various diagnostic and treatment technologies whether or not chronic or long-term illness is a factor.

Because of the nature of Personal Health Records (PHR) and the general circumstances surrounding where they can sometimes be created, added to or just accessed by the User/Patient and/or by any number of Healthcare Providers and/or Government Institutions, the System records many of these within the Personal Diary format. This allows the User/Patient to more easily relate to their own records based around dates and also Healthcare Provider Appointments and Communications.

The System provides such Personal Health Records in a mobile and self controlled structure to also integrate directly to any government's ongoing eHealth systems and initiatives where required, applying any government's eHealth standards to the module.

Module Functionality—
12.1 User/Patient Log-in
   User/Patient Must Be already Logged-in to the Main System
      i. Module Log-in—User/Patient selects Personal Health Records (PHR) Icon—logs User/Patient into PHR from Main System with their personal System Profile (User name) and Password
      ii. User/Patient is then asked to Log-in with their PHR Validation Log-in (secondary) PHR Validation Code
   Although not recommended, this can be made unnecessary if preferred
      iii. User/Patient Personal Health Records (PHR) Access including Synchronisation Rights
   Any PHR Merging, Transfer and/or Synchronisation will require the User/Patient to confirm merging, transfer and/or Synchronisation with their PHR Validation Log-in (secondary) PHR Validation Code
12.2 Symptoms Entry
   12.2.1 Manual Entry—Symptoms Experienced—Time/Date Stamped
      These will then be highlighted to the Healthcare Provider following Synchronisation with the Healthcare Provider PMS (79):
      i. Synchronisation of User/Patient PHR to the Healthcare Provider—Time/Date Stamped when:
      This functionality is subject to the level of system integration provided by each Healthcare Provider's PMS
         a. Prior to Consultation—User/Patient elects to send Electronic Package Transfer (Secured data) via internet
         b. Prior to Consultation—Synchronisation between User/Patient M/APP & Healthcare Provider PMS (79) at Healthcare Provider reception prior to consultation via BlueTooth (85) or USB (86) Interface
         c. During Consultation—Synchronisation between User/Patient M/APP & Healthcare Provider PMS (79) via BlueTooth (85) or USB (86) Interface
         All Synchs—Time and Date Stamped
      ii. Symptoms Logged—Can be entered and/or Changed by User/Patient and/or the Healthcare Provider
      This functionality is subject to the level of system integration provided by each Healthcare Provider's PMS
         a. Undiagnosed Symptoms are each automatically allocated a Unique Identifying Code, which will then be permanently attached to each symptom and will ID them along with a Time/Date Stamp of when they were Logged and/or Re-logged (if re-occurring) with any notes also attached.
         1. As ensuing symptoms are experienced and Logged by User/Patient, providing each falls within a pre-defined period (Eg. 1 week), each will by default be associated to the previously Logged Symptom/s. Each association by default can be easily overridden.
         2. When the user meets with the appropriate Healthcare Provider, the symptoms are identified and consequently acknowledged and dealt with in-tern.
         3. When the Healthcare Provider makes their final Condition Diagnosis, these Logged and Associated Symptoms can be easily but formally attached to the Condition by the Healthcare Provider or in User/Patient in Consultation with the Healthcare Provider.
4. These will remain as a part of User/Patient PHR so that a Healthcare Provider may look for any outstanding symptoms during consultations and as a matter of PHR, they will remain as part of User/Patient Available PHR.
b. Diagnosed Symptoms can be each delegated (tentatively) to Existing Conditions at entry and automatically allocated a Unique Identifying Code, which will then be permanently attached to each symptom and will ID them along with a Time/Date Stamp of when they were Logged and/or Re-logged (if re-occurring) with any notes also attached.
These will remain as part of User/Patient Available PHR.

12.2.2 Healthcare Provider Entry—Synchronised—Symptoms Experienced—Time/Date Stamped via PMS Patient Records (PHR) Synch allows Healthcare Provider to either:
Manually Enter Symptoms Experienced by User/Patient during Consultation
or
Synchronise PMS Patient PHR with User/Patient PHR via User/Patient HHP device:
This functionality is subject to the level of system integration provided by each Healthcare Provider's PMS
a. Prior to Consultation—Electronic Package Transfer (Secured data) via internet
b. Prior to Consultation—Synchronisation between User/Patient M/APP & Healthcare Provider PMS (79) at Healthcare Provider reception prior to consultation via BlueTooth (85) or USB (86) Interface
c. During Consultation—Synchronisation between User/Patient M/APP & Healthcare Provider PMS (79) via BlueTooth (85) or USB (86) Interface
All Synchs—Time and Date Stamped 12.3 Contacts (PHR)—Manages the contact details, some communications and references to User/Patient Healthcare Providers
12.3.1 Contact Classification—means as any Contact is entered into The System, a Classification is required for various reasons within The System use
  i. Class 1—HCP (C1) (HealthCare Provider)—is the Classification used for any Contact used by User/Patient as a Healthcare Provider
  ii. Class 1 (C1)—HCP (HealthCare Providers)—Contacts listed as Medical and Health Providers to the Individual User can be Assigned/Referred to another User within the Household (Main) system though will only assign/refer basic Contact Details. A Full Contact History and Associated Attachments will be retained only within the referring User's Contacts and Diary Records as they are retained as "Class 1—HCP" records.
  iii. Class 1 Contacts and any Activities pertaining to or associated with Class 1 Contacts will become and remain part of the User/Patient Personal Health Records (PHR)
  iv. If User has Dependant Child PHR File attached, (as referred to in 1.0/Main Sys/b)/ii)/a)/ii)), C1 Contacts are also Associated to that specific Dependant Child PHR File Class 1 Contacts require a Provider Number that is obtained from the HealthCare Provider 12.3.2 Referred Contacts:
a. Means a Referred Contact the User/Patient receives electronically as an MS Outlook Contact file—
  i. If actioned by User/patient, The System will import this Contact's Details as a Contact and request of User/Patient that Contact Class be confirmed as Class 1—HCP (if pre-set to do so) with a "Referred By" field that requires manual entry
  ii. Any Class 1—HCP Contact will always carry the "Referred By" field as a visible reference on the Contact Screen
or
b. Means a Referred Contact the User/Patient enters manually as a Contact and Classed as Class 1—HCP with the "Referred By" field also completed
  i. Any Class 1—HCP Contact will always carry the "Referred By" field as a visible reference on the Contact Screen 12.4 Appointment Manager (PHR)—Sets and Manages Appointments/Entries/Reminders with Healthcare Providers through The User/Patient Diary
12.4.1 User/Patient Appointments/Entries/Reminders Diary Entries:
  i. Parallel Entry—means each time an Appointments/Entries/Reminders is entered into the User/Patient Diary with a Class 1—HCP Contact, the entry (if pre-set to do so) will be simultaneously Parallel Entered (mirror entered) into other User/Patient Diaries and tagged according to which Diary
    a. Personal Diary—by default includes PHR Appointments/Entries/Reminders
      NO PHR will be merged, transferred and/or Synchronised unless Target Diary System has HL7 Gateway (HL7g)
      PHR Appointments/Entries/Reminders will show PHR Identification in Personal Diary
      If PHR Appointments/Entries/Reminders are set from other Diaries (Business/Household), they will show only P Identification (Id) & Colour Coded (CC) in the Diary set from
    b. PHR Diary—can be set as a separate PHR Diary if required by User
      Once a Child has a required Medicare number, a separate PHR Diary may be created and used within a Parent's Diary
      This Child's PHR Diary is Automatically Synchronised between Parent PHR Diaries
    c. Household Diary—All Users Access
      Each User has their Entries Colour Coded to the same Defaulted Colour—This Colour can be changed by the User
      Business and Household Diaries can be set to have Personal (P) and Personal Health Records (PHR) Appointments/Entries/Reminders made from within and marked either P(CC) or PHR (CC). In these cases, they will automatically insert (as pre-set) with Default Tag Eg.—
      P—"9:00 am P(CC)"—Available in Business and Household Diaries
      PHR—"9:00 am PHR(CC)"—Available in Household Diary
      PHR Diary Entries can be made by the User/Patient from a Class 1 Contact Screen; Personal Diary; PHR Diary; Household Diary or Business Diary providing they are available from within the HHP device ii. Single Entry—means each time an Appointments/Entries/Reminders is entered into User/Patient Diary with a Class 1—HCP Contact, the entry (if pre-set to do so) will not be simultaneously Parallel Entered (mirror) entered into other User/Patient Diaries 12.5 Entry of Personal Health Records (PHR)

12.5.1 Manual Entry via User/Patient Personal Diary—At any time are entered via either User/Patient M/APP or The Main System by selecting PHR, which are then tagged as PHR i. Included Details from the Chronic Condition Module/s Specific Integration Interface—Section 10.10 (if Pre-set in System Set-up)

12.5.2 Entry of Personal Health Records (PHR)—Synchronise User/Patient M/APP with HealthCare Provider PMS (79)

This functionality is subject to the level of system integration provided by each Healthcare Provider's PMS a. Prior to Consultation—Electronic Package Transfer (Secured data) via internet b. Prior to Consultation—Synchronisation between User/Patient M/APP & Healthcare Provider PMS (79) at Healthcare Provider reception prior to consultation via BlueTooth (85) or USB (86) Interface c. During Consultation—Synchronisation between User/Patient M/APP & Healthcare Provider PMS (79) via BlueTooth (85) or USB (86) Interface All Synchs—Time and Date Stamped 12.5.3 System Responses/Intervention Actions are set-up by User/Patient in consultation with the Providing GP and/or Specialist. Parameters are set to match the individual medical condition and User/Patient needs with some System Responses requiring Interaction Access including Notification/ALERT sends to Providing GP and/or Specialist and/or Other Nominated Party via Predetermined Prioritised System Method/s.

Response available:

i. User Response/No System Response—Time/Date Stamped ii. Send SMS Notification to Providing GP and/or Specialist of User Response—Time/Date Stamped iii. Send SMS ALERT to Providing GP and/or Specialist of User Response—Time/Date Stamped iv. Send SMS Notification to Other Nominated Party of User Response—Time/Date Stamped v. Send SMS ALERT to Other Nominated Party of User Response—Time/Date Stamped vi. Send Email Notification to Providing GP and/or Specialist of User Response—Time/Date Stamped vii. Trigger Further Follow-up System Responses 12.6 Documents Intake & Manager—Referrals/Prescriptions/Provider Assessments/Healthcare Plans/Case Plans/Discharge Details Saved in Sub-directory folder with File Names held by default as the URL link to provider and/or Institution 12.6.1 Manual Save attached Documents—Saved in Sub-directory folder 12.6.2 Auto Intake attached Documents following Synchronisation with HealthCare Provider PMS (79)

12.7 Prescription (PBS) Tracking 12.7.1 Automated Synchronise/Medication and Dispensing Details through Pharmacy using Pharmacy Point of Sale System (78).

This functionality is subject to M/APP use and the level of system integration provided by each Pharmacy Point of Sale System i. All Details of Prescribed Medications dispensed a. Prescribed—PBS/Drug ID (DID)/Time/Date Stamped b. Dispensed—PBS/DID/Time/Date Stamped ii. Medication Reminders set for the User/Patient through User/Patient Diary Alarms, of Medication Dispensing Times and Dosages a. Personal Dispensing—PBS/DID/Time/Date Stamped 12.7.2 Manual Entry/Medication and Dispensing Details through entry of Medication and Dispensing Details Screen i. All Details of Prescribed Medications dispensed a. Prescribed—PBS/Drug ID (DID)/Time/Date Stamped b. Dispensed—PBS/DID/Time/Date Stamped ii. Medication Reminders set for the User/Patient through User/Patient Diary Alarms, of Medication Dispensing Times and Dosages a. Personal Dispensing—PBS/DID/Time/Date Stamped 12.7.3 Web Portal (82) institutional Synchronisation (Only anticipated if M/APP not in use and subject to Government tracking of Dispensed Pharmaceuticals as relevant.)

i. All Details of Prescribed Medications dispensed a. Prescribed—PBS/Drug ID (DID)/Time/Date Stamped b. Dispensed—PBS/DID/Time/Date Stamped ii. Medication Reminders set for the User/Patient through User/Patient Diary Alarms, of Medication Dispensing Times and Dosages a. Personal Dispensing—PBS/DID/Time/Date Stamped 12.8 Prescription (PBS) Re-order Reminder provides the User/Patient with System Sequenced Reminders/Actions according to parameters set in consultation with Prescribing GP or Specialist—Triggered Manually by the User/Patient following—

Re-order Reminder Actions:

i. Alarm Reminder—No Interactions ii. Alarm Reminder Integrated Improvement Tracking: Tracks Changes in Symptoms and/or Overall Condition 12.8.1 Alarm Reminder—No Interactions i. Following Synchronised Setting via Pharmacy Point of Sale System (78). The System will offer to remind User/Patient through User Diary Alarms of Re-order or Re-Prescribing Dates if further Medications are necessary according to Prescribing GP or Specialist advice This functionality is subject to M/APP use and the level of system integration provided by each Healthcare Provider's PMS 12.8.2 Prescription Re-order Reminder—Actions Sequence
i. Reminder/No Reminder
ii. Dispensed—PBS/Drug ID (DID)/Time/Date Stamped
iii. Notice Required/Days
   If The System has been set for a PBS Re-order Reminder against this Prescribing Event, at required notice of completion of the Prescribed Medication Course, The System will according to Prescribing GP or Specialist advice, remind the User/Patient through User Diary Alarms of Re-order Dates if further Medications are necessary
   These Prescribing Re-order Reminders can also be set to be activated through Integrated Improvement Tracking Only if No Improvement of Symptoms or Overall Condition has been acknowledged through Improvement Tracking functionality of The System—Responses based on Prescribing GP or Specialist advice 12.8.3 Following Manual Setting, The System will offer to remind User/Patient through User Diary Alarms of Re-order or Re-Prescribing Dates if further Medications are necessary according to Prescribing GP or Specialist advice
i. Reminder/No Reminder
ii. Dispensed—PBS/Drug ID (DID)/Time/Date Stamped
iii. Notice Required/Days
   If The System has been set for a PBS Re-order Reminder against this Prescribing Event, at the required notice of completion of Prescribed Medication Course, The System will according to Prescribing GP or Specialist advice, remind the User/Patient through User Diary Alarms of Re-order Dates if further Medications are necessary
   These Prescribing Re-order Reminders can also be set to be activated through Integrated Improvement Tracking Only if No Improvement of Symptoms or Overall Condition has been acknowledged through Improvement Tracking functionality of The System—Responses based on Prescribing GP or Specialist advice 12.9 Symptom Tracking—Tracking Changes in Symptoms and/or Overall Condition Using specific Symptom Related Questions and Answers, the System can be set to Record Answers and to also Suggest Prescription Re-order and if necessary, Notify HealthCare Provider of Specific Symptom Changes.

12.9.1 Set-up In Provider PMS (79) by Provider GP or Specialist during Consultation to trigger at—
i. Independent Set Times/Dates
ii. Integrated to Prescription Re-order Reminders
   This functionality is subject to the level of system integration provided by each Healthcare Provider's PMS
   Triggers Symptoms Change Questions—asked of the User/Patient by The System
   If The System has been set for Improvement Tracking
   If Trigger Parameters and Question/s have been Pre-set 12.9.2 Set-up Manually by User/Patient during Consultation or following Provider GP or Specialist Consultation
   Triggers Symptoms Change Questions—asked of the User/Patient by The System
   If The System has been set for Improvement Tracking
   If Trigger Parameters and Question/s have been Pre-set 12.10 Exercise Management
All Functionality available on HHP device (60)
Exercise Management provides User/Patient the ability to develop or be invited to and to manage, Personal and/or Group Exercise Activities and/or Regimes.

12.10.1 Manually Planning using the Contacts and Diaries module (Sec. 5.8.4) allows the User to plan any Individual Exercise Activity and to also create Default Exercise Activities, which can then be selected from a drop-down list each with preset default factors applied.
i. Preferred Day/Time/Period 12.10.2 Receiving Invitation for an activity planned by another Contact/User will on acceptance, be is inserted into the User Diary module applying the preset default factors 12.10.3 Exercise Type can be set as a Planning preset default factor or otherwise left fir Manual Entry 12.10.4 Exercise Intensity can be set as a Planning preset default factor of Exercise Type or otherwise left for Manual Entry 12.10.5 Physical Outcome is triggered for Response if Alarm is Set and can be set as a Planning preset default factor or otherwise left for Manual Entry.

12.10.6 Recovery Action/Time can be set as a Planning preset default factor of Exercise Type or otherwise left for Manual Entry 12.10.7 All Exercise Completed will become Exercise Diary Records and will remain part of User/Patient Available PHR—They can be minimised from Record View and if required, Made Viewable and Reportable
In the case of the User/Patient using a Chronic Condition Module, Exercise Management and Chronic Condition integrated functionality will be used where required.

12.11 Dietary Management
Dietary Management integrates to the Recipe' Library; Exercise Management and Diaries to help User better manage Food Consumption and Dietary Requirements based on Pre-defined User Preferences.
Dietary Management integrates to functions within Household Ordering and Inventory Module—Recipe' Library (Sec. 13.3)

12.11.1 Target Weight provides User the opportunity to target a specific weight allowing the User to more easily maintain the target weight or work towards achieving the target weight 12.11.2 Personal Calorie Target—will allow User to set Personal Calorie Targets
This function can also be set from Household Ordering and Inventory Module—Recipe' Library (Sec. 13.3.4)

12.11.3 Calorie Counter—will allow User to—
i. Apply Personal Calorie Target
ii. Calculate Calorie Totals for Any Recipe' within a Personal or Household Recipe' Library or Portions of the same Recipe'
iii. Search for Recipes' within the Recipe' Library containing Portions of certain Calorie Totals iv. Count the Calorie Totals of Recipe' Portions served to 12.11.4 Personal Calorie Counter—will allow User to Plan Recipe' Regime based on—
  i. Personal Calorie Target
  ii. Favoured ingredients
  iii. Portion Pre-defined Nutrient Targets 12.11.5 Dietary Requirements—will allow User to Pre-define for Meal Planning and Food Consumption purposes.
  i. Excluded or Restricted by Portion—Foods and/or Food Types such as Carbohydrates; Proteins; Sugars; Fats—Saturated/Unsaturated
  ii. Favour by Portion Nutrient Rich Targets such as Carbohydrates and Proteins 12.11.6 Food and Recipe' Planner—will allow User to plan Meals as Activities based on Pre-defined Preferences such as Calorie Targets and Dietary Requirements into either—
  a. Personal Diary
  or
  b. Household Diary 12.12 Chronic Condition Module is for those Users/Patients who have a Chronic Illness/Condition such as Diabetes Assignment to a Career where required
  12.12.1 Each module will be developed in partnership with either Chronic Condition Associations and/or Chronic Illness Specialists with functionality and parameters that are Condition Specific.
    i. Intake of Summary Case Plan
    ii. Intake of Multiple Assessments
      When installed, the module will have changed some interactions with certain functionality depending on the requirements and parameters necessary to be Illness Specific such as Prescription Re-order Reminder; Improvement Tracking; Wellbeing Status Requests and System Responses
      The Diabetes Module is well underway and likely to be the first Chronic Condition Module to be implemented due to Doug's personal health condition and understanding. The module will also include a section of Predictive Modelling to project User/Patient BSL
  12.12.2 Wellbeing Status Requests can be used both with M/APP and Main System if there are Individuals residing with Illnesses such as Diabetics, Asthmatics and alike that may at certain times require or benefit from System Responses/intervention Action/s
    These Status Requests and Interventions have Parameters also requiring set-up in consultation with Providing GP and/or Specialist and the User/Patient due to System Responses in some cases requiring interaction access with Providing GP and/or Specialist.
      i. Request Parameters—Medical Condition Dependant—Set-up by the User/Patient to define their own Parameters
        EG. For Diabetics—Logic Questions to be asked by The System to determine possible Low/High Blood Sugar—System Responses/Intervention Actions can be set-up as previously stated.

12.13 Personally Controlled Electronic Health Records (PCEHR) Web Portal (83) Merging, Transfer and/or Synchronisation—This will be done via Pre-set Web Portal Icon configured to only call up and log onto the Pre-set PCEHR Web Portal.

User/Patient Log-in—User/Patient Must Be already Logged-in to the Main System 12.13.1 Function Activation—User/Patient selects Web Portal Icon—logs User/Patient into PHR from Main System with their personal System Profile (User name) and Password 12.13.2 User/Patient is then asked to confirm merging, transfer and/or Synchronisation with their PHR Validation Log-in (secondary) PHR Validation Code
  Although not recommended, this can be made unnecessary if preferred 12.13.3 User/Patient PCEHR now available for Merging, Transfer and/or Synchronisation 12.14 Institutional Web Portal (84) Synchronisation—This will be done via Pre-set Web Portal Icon configured to only call up and log onto the Pre-set Institution Web Portals.
  This functionality is subject to the level of system integration provided by each Institution
  This Function can also be Triggered Only from inside the Personal Healthcare Module 12.14.1 User/Patient Log-in—User/Patient Must Be already Logged-in to the Main System 12.14.2 Function Activation—User/Patient selects Web Portal Icon—logs User/Patient into PHR from Main System with their personal System Profile (User name) and Password 12.14.3 User/Patient is then asked to Log-in with their PHR Validation Log-in (secondary) PHR Validation Code
  Although not recommended, this can be made unnecessary if preferred 12.14.4 De-Identified PHR Datashare (dIDPHR) (Proprietary Standard) is available for merging, transfer and/or Synchronisation with certain institutions. This function is only offered where the institution requesting PHR Datashare by Electronic Request, provides the dIDPHR Request. dIDPHR is activated by selecting the dIDPHR Tick Select option in System Pop-up following the Institution dIDPHR request.

12.14.5 User/Patient Personal Health Records now available for merging, transfer and/or Synchronisation 12.15 Privacy Control is set to limit availability of PHR to User/Patient Healthcare Providers based on Individual User/Patient personal or legal requirements at discretion of Individual User/Patient
  Privacy Control must be Set per Healthcare Provider
  12.15.1 No Default Setting
    i. If User/Patient attempts to merge, transfer and/or synchronise with a Healthcare Provider Practice Management System or an Institutional Management Information System prior to setting Privacy Control PHR Access Level for that Healthcare Provider or Institution, The System will Require User/Patient to set PHR Access Level before merging, transfer and/or Synchronisation
  12.15.2 Privacy Control Settings can be set from—
    i. Healthcare Providers Screen during Set-up—Main System/M/APP
    ii. Healthcare Provider's Screen prior to Consultation/s—Main System/M/APP
    iii. Reminder Screen Prior to Consultation/s—Main System/M/APP 12.16 Health Fund & Rebate Manager—via Main System only
  12.16.1 System Logs onto Health Fund Provider's Management System via Health Fund Provider's Web Portal (77)
    i. User/Patient Logs into Provider's Web Portal using Account Number and Password
      a. Details Logged and delivered each subsequent Log-in
    ii. Request Statements
      a. Request Financial Year/To/Date Statement—All Transactions Logged into Main System
      b. Request Previous Financial Year—All Transactions Logged into Main System
    iii. Rebate Claims
      a. Synchronise Claimable Transactions—Rebates against Claimable Items
    iv. Value For Money Calculation
      a. Calculate Current Fees Paid vs Rebates Paid
    v. Health Fund Level of Coverage Calculation
      a. List Specific Features of Other Coverage Plans Available
      b. Calculate against—Indicate most appropriate Coverage Offered by Provider
        1. Current YTD
        2. Last 2 Years
        3. Last 5 Years
    vi. Auto Logged into Main System
      a. Activation once Main System has logged-off Health Fund Provider's Web Portal (77)
      b. Rebates Made against Claimed Items Logged—Time/Date Stamped
12.17 Synchronise the Main System with M/APP creates the merging, transfer and/or Synchronisation of any Existing User/Patient PHR Diary Main System and M/APP data. Once HHP connected via standard Access Method, The System will confirm you are ready to merge, transfer and/or Synchronise both Systems
  If User/Patient is Logged-in to PHR within either the M/APP or Main System, the System will confirm, "Only PHR to be Synchronised"
  If PHR's are to be merged, transferred and/or Synchronised, User/Patient is then asked to confirm merging, transfer and/or Synchronisation with their PHR Validation Log-in (secondary) PHR Validation Code
    i. Once Approved, System will Synchronise
    ii. System will Alert when Synchronisation Complete
    iii. Disconnect HHP device
    iv. Disconnection Registered
12.18 Module Reporting
  All Reports are Date/Time Logged
  These reports will be subject to discussions with Health Departments, Medical and other Allied Health associations to establish what will be considered to be relevant and worthwhile
13.0 Household Ordering & Inventory Module
Module Overview:
  The Household Ordering & Inventory Module is specifically designed to be an aid in assisting Users better manage their personal time, meal planning and the cost of groceries to achieve and maintain better overall household budget control.
  The module will also help in maintaining a wide selection of food groups and types including maintaining of overall Nutritional Values of foods held, adding to better health management outcomes for the household members. This will make the management of weight loss and health conditions that are partly reliant on food consumption such as Diabetes considerably easier to manage.
  For Scanning Barcodes of products, the Main System will interface with $3^{RD}$ Party Barcode Scanning devices. In the situation where using the Module within the M/APP, the System will use the HHP Scanning capacity where available.
Module Functionality—
13.1 User Log-in:
  User Log-in for General Module Access is only necessary if User is NOT logging into the main system
  User Log-in provides—
    i. Records Access
    ii. User Recognition—Date/Time Logged
    iii. User & Household Inventory—Date/Time Logged
    iv. User & Household Ordering—Date/Time Logged
    v. Synchronisation to HHP device—Date/Time Logged
13.2 Enter Inventory—
  a. Manually via Items Detail Screen if no Scanner Function available
    Enter Inventory Manually is activated by the User selecting "Enter Product", which then activates a pop-up "Item Details Screen" if no Scanner Function available
  b. Using Scanner if Scanner Function available
    Enter Inventory Using Scanner Function is activated by the User selecting "Enter Product", which then activates a pop-up if a Scanner Function is detected, "Scanner Found" after which the "Scan Product Screen" will appear stating "Scan Product"
13.3 Recipes' Library—when selected by User provides
  13.3.1 New Recipe' Library—will allow User to create a New Library for—
    a. Personal—allows User to assign any Recipe' to—
      i. Personal Recipe' Library
      ii. Personal & Household Recipe' Libraries
    b. Household—means All Users within the Household System will have access to use—
      i. All Existing Recipes'
      ii. New Recipes' Created from Household Library are assigned by default to Household Library
  13.3.2 Existing Recipe' Library—will allow User to access all Recipes' within—
    a. Personal Recipe' Library
    b. Household Recipe' Library
  13.3.3 New Recipe' Create—will allow User to create New Recipes' including Cooking Instructions
  13.3.4 Personal Calorie Target—will allow Users to set Personal Calorie Targets
    This function can also be set from Healthcare Management Module—Dietary Management (Sec. 12.11.2)
  13.3.5 Calorie Counter—will allow User to—
    a. Apply Personal Calorie Target
    b. Calculate Calorie Totals for Any Recipe' within a Personal or Household Recipe' Library or Portions of the same Recipe'
    c. Search for Recipes' within the Recipe' Library containing Portions of certain Calorie Totals
    d. Count the Calorie Totals of Recipe' Portions served
  13.3.6 Personal Calorie Counter—will allow User to Plan Recipe' Regime based on—
    i. Personal Calorie Target
    ii. Favoured Ingredients
    iii. Portion Pre-defined Nutrient Targets 13.3.7 Dietary Requirements—will allow User to Pre-define
  i. Excluded or Restricted by Portion—Foods and/or Food Types such as Carbohydrates; Proteins; Sugars; Fats—Saturated/Unsaturated
  ii. Favour by Portion Nutrient Rich Targets such as Carbohydrates and Proteins
13.3.8 Recipe' Planner—will allow User to plan meals as Activities into either—
  a. Personal Diary
  or
  b. Household Diary
13.3.9 Ingredient Check—will provide an Inventory Status on Recipe' Ingredients with option to Add Items to—
  a. Existing Shopping List
  or
  b. Created Shopping List
13.4 Shopping List Creator—when selected by User will create Shopping List made up from "Pre-set Minimum Inventory Hold"
13.5 Product Ordering will create the Shopping List and convert to—
  a. Print Shopping List—System will send a print request to the Local Printer
  b. Hold Order in Pending—System will Save Order in Pending File
  c. Place Web Order—System will log onto the Product Order fulfillment Web Portal (81) using Account Number and Password
13.6 Current & Projected Usage & Costing (Via PUP) will calculate—
  13.6.1 Current Usage & Costing
  13.6.2 Projected Usage & Costing over Nominated Period
  13.6.3 Product Comparison Testing—will compare Stocked Food Items or Other Products by User Selection
    i. The System will deliver by request various Product Comparisons
      Outcome Results will be Logged and Saved in Household Inventory
13.7 Synchronise the Main System with M/APP creates the Synchronisation of any Existing User specific Ordering and Inventory file Main System and M/APP data. Once HHP connected via standard Access Method, The System will confirm you are ready to Synchronise both Systems
  i. Once Approved, System will Synchronise
  ii. System will Alert when Synchronisation Complete
  iii. Disconnect HHP device
  iv. Disconnection Registered
13.8 Module Reporting:
  All Reports are Date/Time Logged
  System will report on—
    i. Current Inventory
    ii. Items Held
    iii. Value
    iv. Restocking History
      1. Dates; Order items & Values
    v. Previous Orders
      1. Dates; Order Items & Values MOBILE APPLICATION as Stand-Alone Product Run on a Hand Held Peripheral Device (M/APP)

Also Providing Complete Integration to RESIDENTIAL MANAGEMENT SYSTEM

System Statement—Inc. Specified Functions

System Introduction:
  The overall Mobile Application will help individual users with the modules they choose to use independently of the Residential Management System and/or as an integrated User Interface capable of merging information with the Residential Management System and HealthCare Systems.
  The Mobile Application will help the User with areas of Personal Management that due to technology, are now more easily and more practically managed through this technology. The management advantages the technology delivers in each area of the System are seen as Functional Management; Budgetary Management in both Savings to be made from more prudent Consumption and also Planning and the final, Personal Health Management.
  The HHP must provide a sufficient level of Log-on Password Security
  Many system functions require direct Internet Access
  Terminology and Standards
  a. System Design and Structure:
    Database Structure will be—
      SQL Relational Database
  b. Terminology:
    User and/or User Patient refers to User, the System is Registered to
    HCP refers to HealthCare Provider of User/Patient, the System is Registered to
      This can include both Public Institutions: Hospitals & Clinics and Private Institutions; Hospitals; Clinics & Private Practices
    Institutional De-Identified PHR Datashare (dID-PHR)—Only available to Preset Institutions
    PHR refers to Personal Health Records of User/Patient
    R/T refers to Real-Time
  c. System Principals:
    Access/Data/Entry Principals
      All Access/Data Entries/Data Changes/Data Merging/Date Transfer/Data Synchronisation only made by Approved Level Access
      All Diary Entries/Changes—ID/Time/Date Logged to establish Audit Trail
      All PHR Diary Entries/Changes—ID/Time/Date Logged, maintained and available as PHR
  d. System Integration:
    $3^{RD}$ Party Systems Integration
      Voice Recognition System—Only if HHP has installed
      PDF Writer—Only if HHP has installed
      Email and Calendar System
      Barcode Scanner—Only if HHP has installed
  e. Diary System:
    Diary System offers—
      Personal Diary—by default includes PHR Appointments/Entries/Reminders
        NO PHR will be merged, transferred and/or Synchronised unless Target Diary System has HL7 Gateway (HL7g)

PHR Appointments/Entries/Reminders will show PHR Identification in Personal Diary
If PHR Appointments/Entries/Reminders are set from other Diaries (Business/Household), they will show only P Identification (Id) & Colour Coded (CC) in the Diary set from
PHR Diary—can be set as a separate PHR Diary if required by User
Once a Child has a required Medicare number, a separate PHR Diary may be created and used within a Parent's Diary
This Child's PHR Diary is Automatically Synchronised between Parent PHR Diaries
Business Diary—Can be set to Synchronise on Demand with Office Diary
Household Diary—Single User Access only
User has their Entries Colour Coded to the same Defaulted Colour—This Colour can be changed by the User and would ideally use the same Default Colour selected for the Main Household System
All Diaries can be set to have Personal Diary entries Inserted and marked P(CC)
Business and Household Diaries can be set to have Personal (P) and Personal Health Records (PHR) Appointments/Entries/Reminders made from within and marked either P(CC) or PHR (CC)
In these cases, they will automatically insert (as pre-set) with Default Tag Eg.—
P—"9:00 am P(CC)"—Available in Business and Household Diaries
PHR—"9:00 am PHR(CC)"—Available in Household Diary
When Multiple Diaries are used by the User, All Diary Entries outside their Specified Diary and if pre-set to show, are Default Tagged by the User: P (Personal); PHR (Personal Health Records); B (Business) and HH (Household)
f. Synchronisation:
Synchronisation of—
i. All Diary Records including—
User Personal Diary carrying PHR/PBS Records
PHR Diary carrying PHR/PBS Records
Business Diary
Household Diary
ii. Other Standard Communication and Information Synchronisation
Synchronisation of M/APP with:
Main System—HL7 Gateway—PBS/PHR
Healthcare Provider's Practice Management System—HL7 Gateway—PBS/PHR
Pharmacy Point of Sale System—HL7 Gateway—PBS
Any PHR Merging, Transfer and/or Synchronisation will require the User/Patient to confirm Merging, Transfer and/or Synchronisation with their PHR Validation Log-in (secondary) PHR Validation Code
Synchronisation Access Method
Synchronisation via USB Cable
Synchronisation via Bluetooth
Synchronisation via Web Portal—Only available to Preset Institutions
Synchronisation/Communication/Integration Standard
HL7 Gateway
Australia—NEHTA prescribed: Standards Australia Point to Point Secure Messaging Standards
De-Identified PHR Datashare (dIDPHR) (Proprietary Standard)
Point to Point Secure Messaging—National (Country Dependent) or International Standards (ISO)

Please Note—

This invention relates to the overall Personal and Healthcare management of The User including in as many areas as seen practical, employing Artificial Intelligence including again in the areas seen practical, Voice Controlled through User Voice Recognition to both facilitate and encourage use, security and functionality of the system.

This is a unique use of such features within the everyday use of any type of management system.

The system provides many areas of Individual Personal and Healthcare Management.

The system covers the following areas of management—
Module Index—
1. Mobile Contacts & Diaries
2. Mobile Accounts
3. Mobile Security
4. Mobile Travel
5. Mobile Electronic Vehicle Log Book (eVLB)
6. Mobile Personal Healthcare
7. Mobile Ordering & Inventory 1.0 Mobile Contacts & Diaries:
Module Overview:
The Mobile Contacts & Diaries Module provides the User with the means to keep accurate records of personal and shared Contacts also providing the ability to manage Personal. Healthcare, Shared Household and Business Activities through Personal and/or Common Diaries (where used).

The System also provides the ability to track and record details for Incoming and Outgoing Calls.
Module Functionality—
1.1 User Log-in:
User Log-in for General Module Access is only necessary if User is NOT logging into the HHP device system
User Log-in provides—
 i. Records Access
 ii. User Recognition—Date/Time Logged
 iii. User Contacts and Interaction—Date/Time Logged
 iv. User Diaries and Interaction: std Personal/PHR Diary; Business Diary and Household (where used)—Date/Time Logged
 v. Synchronisation to Main System—Date/Time Logged
1.2 User & Household Contacts
 1.2.1 Referred Contacts—Means if the User receives an MS Outlook Contact, The System will import this Contact's Details and request of the User that Contact Class be nominated.
 1.2.2 User & Household Contact Classes—Record and Management of Household classified and individually classified and Maintained Contacts.
  i. Class 1 (C1)—HCP (HealthCare Providers)—Contacts listed as Medical and HealthCare Providers to the Individual User can be Assigned/Referred to another User within the Household (Main) system though will only assign/refer basic Contact Details. A Full Contact History and Associated Attachments will be retained only within the referring User's Contacts and Diary Records as they are retained as "Class 1—HCP" records.

a. Class 1 Contacts and any Activities pertaining to or associated with Class 1 Contacts will become and remain part of the User/Patient Personal Health Records (PHR)

b. If User has Dependant Child PHR File attached, (as referred to in 1.0/Main Sys/b)/ii)/a)/ii)), C1 Contacts are also Associated to that specific Dependant Child PHR File Class 1 Contacts require a Provider Number that is obtained from the HealthCare Provider ii. Class 2 (C2)—Contacts held within the Household Contact List and can be common to each Individual User within the Household holding a Full Contact History and Associated Attachments.

iii. Class 3 (C3)—Contacts held by a specific User within the Household (Main) system holding a Full Contact History and Attachments.

iv. Class 4 (C4)—Contacts held by a specific User within the Household holding a Full Contact History and Attachments—May have a limitation.

1.3 Caller ID Recognition for Inbound Calls will only be available to M/APP if the HHO device is a Mobile Phone. This functionality will be dependant on the Mobile Phone manufacturer and whether or not an interface can be developed from the Device's incumbent Caller ID to the User Diary; the User Contacts System and their functionality.

If this interface is developed, the following will apply—

ID the source number of calls made to the Device where available and Caller provides Phone Number ID available Inbound Call History will be kept against All Contacts within the System and available for anytime view by the User 1.3.1 When Caller ID is Provided—System will Search Contact Records for Identified Number i. If Contact Record Found—System will create Call Received Pop-up Showing "User Name" of whom the ID In-Coming Caller belongs within the System; Caller/Contact Name of Identified Number—with Call Reason Field to record any information by User ii. If Contact Record Not Found—If Option Pre-set, System will provide Optional New Contact Pop-up to Record Contact Details—Name; User; Company; Address; Phone Numbers; Emails 1.4 The User Diary will maintain a Complete Diary of any User Activities also with a History maintained against any User Contacts within the Contacts and User Diary Module associated with that Activity 1.4.1 The Activity Planner as outlined in eVLB module allows the user to plan any Individual Activity and to also create Default Activities, which can then be selected from a drop-down list each with preset default factors applied including Exercise that will apply default factors from the Healthcare Management Module (Personal Health Records)—Exercise Management (sec. 6.10) if the module is used by the User creating the Activity in which case the Exercise components of the Activity will become part of the User PHR.

1.4.2 Vehicle Scheduling Diary (VSD) as outlined in eVLB—If a vehicle has Multiple Users, it can also carry its own Vehicle Scheduling Diary (VSD). This VSD will be directly Associated to the Vehicle Specific eVLB and be Synchronised simultaneously with All Other eVLB Records. Any Associated Vehicle User can create a Vehicle Booking for the Specific Vehicle within the VSD. This Booking will then require Booking Approval by the Vehicle Administrator, which will then Schedule the Vehicle Booking within the VSD. This Booking Approval will be requested and can be answered via the System.

a. If approved by the Vehicle Administrator, the Vehicle Booking will be highlighted as an Approved Booking in both VSD and Booking User Diary—If Booking User holds more than one Diary, Diary selection takes place at time of Booking.

b. If not approved by the Vehicle Administrator, the Vehicle Booking will be highlighted as an Un-Approved Booking in both the VSD and Booking User Diary.

At time of Approval Request, the Vehicle Administrator then has the option of— i. Creating a Vehicle Booking under their own name or another Associated User.

ii. Creating a Waiting List with the Requesting User as No. 1 including option of adding other Associated Users.

1.4.3 Travel Planner as outlined in eVLB module, allows User to add/create details such as Travel Destination; Projected and/or Expected Travel & Sundry Costs (Public or Private Transport inc. Vehicle Allocation via Vehicle Scheduling Diary) and Costs to a New or Existing Vehicle Allocation Entry via Vehicle Scheduling Diary: User Personal and/or Business Diary by— i. Creating New Details or ii. Recalling Existing Details from a Previous or Coming Activity 1.4.4 Fuel Cost Planner as outlined in eVLB module, allows User to add/create Fuel Costs to a New or Existing Diary Activity/Vehicle Allocation Entry by Estimation or by triggering Distance Plotter 1.4.5 Distance Plotter as outlined in eVLB module, is triggered from within either— i. The Fuel Cost Planner as the next step to complete Fuel Cost Planning or ii. Any Activity as a component of planning process Distance Plotter will calculate distances using— a. "Google Maps" by selecting button where internet access available or b. Other $3^{rd}$ party systems available by selecting button where internet access available iii. Manually Enter Address into Google Maps or other Address Field or iv. Select from Contact List will populate the Google Map or other Address Field with Existing Address v. System will calculate Distance to be Travelled then by request, against a specific Motor Vehicle included in Vehicle Scheduling Diary and Associated to User using Current Mileage 1.4.6 Conventional Vehicle Projected Mileage to as outlined in eVLB module, Purchase Fuel providing the means to project the mileage based on Historical/Current Mileage 1.4.7 Hybrid or Electric Vehicle Projected Mileage to as outlined in eVLB module, Purchase Fuel and/or Plan Battery Charges providing the means to project the mileage based on Historical/Current Mileage 1.4.8 Projected Costs including Motor Vehicle Service Costs as outlined in eVLB module, which are calculated from existing Specific Vehicle History and amortised over the projected distance the Specific Vehicle is likely to drive for the period nominated for the calculation 1.4.9 Road and Driving Conditions as outlined in eVLB module, will estimate Travel Time based on Expected Road, Weather and Traffic Conditions plus Expected Average Speed 1.4.10 Fuel Type Price Variance/Value Threshold calculates the different consumption rates of different Fuel Octane Level Types, which will vary from vehicle to vehicle. With the different Consumption Levels recorded against the different Mileages, the system calculates a Variance/Value Threshold.

1.5 SMS Contact Messaging where available through Telecommunications Provider, System allows User the ability to enter and send SMS and MMS Messages to Contacts within System with recorded mobile phone numbers and active mobile phones 1.6 Synchronise the M/APP with Main System—Once connected via standard Access Method, The System will confirm you are ready to Synchronise both Systems If User is Logged-in to PHR within either the Main System or M/APP, the System will confirm, "Only PHR to be Synchronised"

If PHR's are to be Merged, Transferred and/or Synchronised, User/Patient is then asked to confirm Merging, Transfer and/or Synchronisation with their PHR Validation Log-in (secondary) PHR Validation Code
  i. Once Approved, System will Synchronise
  ii. System will Alert when Synchronisation Complete
  iii. Disconnect HHP device
  iv. Disconnection Registered 1.7 Module Reporting—Only available from Main System 2.0 Mobile Accounts Module Overview:

The Mobile Accounts Management Module provides the User with the ability to create Accounts and Sub-accounts to represent Expenses; Income; various credit accounts such as Superannuation; Investments; Savings Accounts various debit accounts such as Credit Cards; Loans and Mortgages and also ATM Transactions. The Accounts Management module then allows the recording of Personal and Family Financial Account Transactions within such accounts all with Web Portal Interface capability. The system also provides Statements and Reconcillations for each Account and Sub-account.

This functionality requires direct Internet Access

This functionality is subject to the level of system integration provided by each Financial Institution Module Functionality—

2.1 User Log-in

User Log-in—User Must Be already Logged-in to the Main System 2.1.1 Module Log-in—User selects Mobile Accounts Icon—logs User into Mobile Accounts module with their personal System Profile (User name) and Password User Log-in provides—
  i. Records Access
  II. User Recognition—Date/Time Logged
  iii. All Functionality—Date/Time Logged 2.2 Create Account/s Create Account/s provides the user with the ability to create an Account or Sub-account for the following—

2.2.1 Income—Multiple possible
2.2.2 Expense—Multiple possible
2.2.3 Credit—Multiple possible
2.2.4 Debit—Multiple possible 2.3 Account Transaction Synchronizing Account Transaction Synchronizing provides the user with the ability to Synchronise all Account and Sub-account Transactions with Mobile Accounts.

This functionality is only available to Users within the Main Household System.

2.4 Web Portal Account Synchronisation—This will be done via Pre-set Web Portal Icon configured to only call up and log onto the Pre-set Financial Institution Web Portals (80).

This functionality is subject to the level of system integration provided by each Financial Institution This functionality can also be Triggered Only from outside the Mobile Accounts Module 2.4.1 User Log-in—User Must Be already Logged-in to Mobile Accounts 2.4.2 Function Activation—User selects Specific Institution Icon—logs User into the Financial Institution Account from Mobile Account System with their personal Financial Institution Account System Profile (User name) and Password 2.4.3 User is then asked to Log-in using their Mobile Accounts' Validation Log-in (secondary) Mobile Accounts' Validation Code Although not recommended, this can be made unnecessary if preferred 2.4.4 User specific account details now available for Synchronisation 2.4.5 Log Off discontinues any Synchronisation and disconnects Web Portal session 2.5 System Account Statements and Reconciliations System Account Statements and Reconciliation provides the user with the ability to create—

2.5.1 Statements
  i. To Date Statements
  ii. Financial Year Statements 2.5.2 Reconciliations
  i. Account Reconciliations 2.6 Module Reporting All Reports are Date/Time Logged System will report on all Created Accounts—
  i. Income
  ii. Expense
  iii. Credit
  iv. Debit 3.0 Mobile Security Module Overview:

The Mobile Security module provides the User with the means to Monitor, Control and Report on Security of their Household, Motor Vehicles and Personal.

Module Functionality—

3.1 Web Portal to Integrate with $3^{rd}$ Party Household Alarm System and 3 Part Motor Vehicle Alarm System—This will be done via a pre-set Web Portal Icons configured to only call up and log onto pre-set $3^{rd}$ Party Household Alarm System and $3^{rd}$ Party Motor Vehicle Alarm System Web Portals.

This functionality is subject to each $3^{rd}$ Party Household Alarm and $3^{rd}$ Part Motor Vehicles Systems matching the defined Security Interface This functionality can't be Triggered from outside the HHP Security System/Module and may require a secondary security login This functionality requires direct Internet Access 3.1.1 User Log-in—User Must Be already Logged-in to Security Module 3.1.2 Function Activation—User selects Specific Household or Motor Vehicle Security module Icon—logs User into either Security Account via specific Security System Web Portal Interface (95) with their personal Security Account System Profile (User name) and Password 3.1.3 User is then asked to Log-in using their Mobile Securities' Validation Log-in (secondary) Mobile Accounts' Validation Code Although not recommended, this can be made unnecessary if preferred 3.1.4 User specific account details now available for Synchronisation 3.1.5 Log Of discontinues any Synchronisation and disconnects Web Portal session 3.2 Household provides the User the ability to login to a Web Service providing—
  i. Remote Monitoring
  ii. Remote Control 3.3 Motor Vehicles
  i. Remote Monitoring
  ii. GPS Locator
  iii. Remote Control 3.4 Personal
  i. Emergency Alarm
  ii. GPS Locator
  iii. Alert Notification 3.5 Module Reporting
  All Reports are Date/Time Logged
  i. Household
  ii. Motor Vehicles
  iii. Personal 4.0 Mobile Travel Module Overview:

The Travel Module provides the User with a selection of local Compatible ATM's: a Currency Conversion Calculator and an ATM Transactions Table.

This functionality requires direct Internet Access

Module Functionality—

4.1 Web Portal Interface (101) to call up $3^{rd}$ Party ATM Locator web service application.

4.2 Module to interface with $3^{rd}$ Party ATM Locator web service application and $3^{rd}$ Party GPS Locator to identify the location of various ATM Machines within a designated range.

4.3 Currency Conversion converts any inputted Exchange Rate between any designated currencies and hold this Exchange Rate until User decides to delete or override.
  4.3.1 Conversion Transactions allows the User to Associate a Currency Conversion action to an ATM transaction.

4.4 ATM Transactions allows the User to record any ATM Transactions by recording—
  i. ATM Locations
  ii. Account Used
  iii. Amount in Home Currency 4.5 Travel Budget allows the User to set a specific monetary Travel Budget in the Home Currency or a local Destination Currency.
  4.5.1 The Travel Budget may be started by—
    i. Selecting an Activity (Sect. 5.5.1) or Travel Plan (Sect. 5.5.3)
    ii. Select Start Budget icon
  4.5.2 User can maintain an ongoing Budget Balance to match Accounts Used by updating Account Transactions as they are made via ATM or other means such as Credit Card or Internet transactions
  4.5.3 User can invite another recorded Contact to take part in the Travel Budget 4.6 Module Reporting
  i. Transactions Made
  ii. Budget Status 5.0 Mobile Electronic Vehicle Log Book: (eVLB)

Module Overview:

The Electronic Vehicle Log Book (eVB) is an Electronic Log of all use and history of Specific Motor Vehicles.

The eVLB is a stand alone file that is designed to be a Fixed Electronic Record of the Vehicle's Ongoing History. At the time the file is commenced, the file set-up will require a Vehicle Identification Number/Chassis Number (VIN/CN) from which the System will create a Unique Electronic Signature that can't be changed and will remain perpetually assigned to the VIN/CN. This eVLB can be a multi-user eVLB or a single user eVLB. The Registered Owner of the Motor Vehicle is set-up as Vehicle Administrator of the Vehicle Specific eVLB and has Administrative Rights over that Vehicle Specific eVLB. The Vehicle Administrator can Associate and Un-associate any Resident/User to their Vehicle's eVLB as a Vehicle User. Each Associated Vehicle User within the Household/Main System has access to their Personal Version of the Vehicle Specific eVLB inc. Vehicle Scheduling Diary (VSD) if provided by and at the discretion of Vehicle Administrator. Each Personal Vehicle Specific eVLB is Synchronised with the Main System with All Vehicle History accessible through each Personal Vehicle Specific eVLB and by all Vehicle Users through the Main System eVLB.

Module Functionality—

5.1 User Log-in:

User Log-in for General Module Access occurs automatically once User is logged into the HHP device User Log-in provides—
  i. Records Access
  ii. User Recognition—Date/Time Logged
  iii. Approved eVLB Access—Date/Time Logged
  iv. Synchronisation to Main System—Date/Time Logged 5.2 Create eVLB:

Create eVLB provides the Registered Owner (Vehicle Administrator) of a Vehicle the ability to—
  5.2.1 Create an eVLB, which provides the means for the Registered Owner (Vehicle Administrator) of a Vehicle to—
    i. Capture and log their specific use of the Specific Motor Vehicle into an Electronic Vehicle Log Book format. The eVLB is a stand alone file that is a Fixed Electronic Record of the Vehicle's Ongoing History.
    ii. At the time the file is commenced, file set-up will require a Vehicle Identification Number/Chassis Number (VIN/CN) from which the System will create a Unique Electronic Signature, which can't be changed and will remain perpetually assigned to the VIN/CN.
    iii. At the time the file is commenced, file set-up will require the Vehicle Administrator (Registered Owner) of the Vehicle. Motor Vehicle Drivers License number, which will be taken by default from the Main System. If the Vehicle Administrator does not have their Motor Vehicle Drivers License number registered in the Main System, the System will require this before commencing the file.

iv. Allocate User Rights of the eVLB for the purpose to View and/or Add to
  a. User Recognition/Notification—Date/Time/Kms Logged
  b. Vehicle Scheduling Diary—View & Request
  c. Fuel/Oil Purchases—Date/Time/Kms Logged
An Allocated User of a Specific Vehicle may potentially hold this eVLB file on their individual HHP device 5.3 Vehicle Scheduling Diary (VSD):
  If a vehicle has Multiple Users, it can also carry its own Vehicle Scheduling Diary (VSD). This VSD will be directly Associated to the Vehicle Specific eVLB and be Synchronised simultaneously with All Other eVLB Records. Any Associated Vehicle User can create a Vehicle Booking for the Specific Vehicle within the VSD. This Booking will then require Booking Approval by the Vehicle Administrator, which will then Schedule the Vehicle Booking within the VSD. This Booking Approval will be requested and can be answered via the System.
    a. If approved by the Vehicle Administrator, the Vehicle Booking will be highlighted as an Approved Booking in both VSD and Booking User Diary—If Booking User holds more than one Diary, Diary selection takes place at time of Booking.
    b. If not approved by the Vehicle Administrator, the Vehicle Booking will be highlighted as an Un-Approved Booking in both the VSD and Booking User Diary.
      At time of Approval Request, the Vehicle Administrator then has the option of—
      i. Creating a Vehicle Booking under the Vehicle Administrator name or another Associated User.
      ii. Creating a Waiting List with the Requesting User as No. 1 including option of adding other Associated Users.

5.4 Travel Planner:
  Travel Planner allows User to add/create details such as Travel Destination; Projected and/or Expected Travel & Sundry Costs (Public or Private Transport inc. Vehicle Allocation via Vehicle Scheduling Diary) and Costs to a New or Existing Vehicle Allocation Entry via Vehicle Scheduling Diary; User Personal and/or Business Diary by—
    i. Creating New Vehicle Allocation Entry
    or
    ii. Recalling Existing Details from a Previous or Coming Vehicle Allocation Entry
  5.4.1 Fuel Cost Planner allows User to add/create Fuel Costs to a New or Existing Diary Activity/Vehicle Allocation Entry by Estimation or by triggering Distance Plotter
    The Fuel Cost per Litre can be entered either—
    i. Manually
    or
    ii. Selected via Fuel Watch (or equivalent) Web Portal Interface as described in Item—9.5 Update Fuel Prices
  5.4.2 Distance Plotter is triggered from within either—
    i. The Fuel Cost Planner as the next step to complete Fuel Cost Planning
    or
    ii. Any Vehicle Allocation Entry as a component of planning process Distance Plotter will calculate distances using—
      a. "Google Maps" by selecting button where internet access available
      or
      b. Other 3$^{rd}$ party systems available by selecting button where internet access available
    iii. Manually Enter Address into Google Maps or other Address Field
    or
    iv. Select from Contact List will populate the Google Map or other Address Field with Existing Address
    v. System will calculate Distance to be Travelled then by request, against a specific Motor Vehicle included in Vehicle Scheduling Diary and Associated to User using Current Mileage
  5.4.3 Conventional Vehicle Projected Mileage to Purchase Fuel providing the means to project the mileage based on Historical/Current Mileage
  5.4.4 Hybrid or Electric Vehicle Projected Mileage to Purchase Fuel and/or Plan Battery Charges providing the means to project the mileage based on Historical/Current Mileage
  5.4.5 Projected Costs including Motor Vehicle Service Costs, which are calculated from existing Specific Vehicle History and amortised over the projected distance the Specific Vehicle is likely to drive for the period nominated for the calculation
  5.4.6 Road and Driving Conditions will estimate Travel Time based on Expected Road, Weather and Traffic Conditions plus Expected Average Speed
  5.4.7 Fuel Type Price Variance/Value Threshold calculates the different consumption rates of different Fuel Octane Level Types, which will vary from vehicle to vehicle. With the different Consumption Levels recorded against the different Mileages, the system calculates a Variance/Value Threshold.

5.5 Update Fuel Prices via 'Fuel Watch' (or equivalent) Web Portal Interface (71) using an Internet Connection
  5.5.1 Fuel Cost Planner in conjunction with 'Fuel Watch' (or equivalent) price monitoring & distance calculations via GPS (or estimation) to—
    i. A nominated number of Closest Fuel Stations (to System Residence; Present Location; other Nominated Location or Plotted Journey via Item—9.4.2 Distance Plotter)
    ii. To calculate the Fuel Cost vs Klm's to travel to identify the most Financially Worthwhile station to purchase fuel from based on—
      a. Distance
      b. Projected Fuel Consumption
      c. Monitor & Input (User Selection)—'Fuel Watch' (or equivalent) will need to capture Trading Hours and confirm Fuel Availability at Time of Report
    This section remains subject to confirmations with 'Fuel Watch' (or equivalent) these Web Portal Interface functions are possible 5.6 Service and Maintenance Log:
  5.6.1 Motor Vehicle Servicing Program logs all Specific Vehicle Services and Costs into the Electronic Vehicle Log Book (eVLB) file.
    i. This is done by using the Vehicle Manufacturer's Prescribed Service Program as the template with alarms set to warn of upcoming Due Service including the Prescribed or Expected Costs.
    ii. The Alarms will also alert Vehicle Users of Pending Service Due falling during or near Planned Vehicle Usage logged as Activities within the Diary.

5.6.2 Motor Vehicle Service Booking logs onto the Service Centre Management Information System (MIS) Web Portal Interface (70) using an Internet Connection.
  i. The system will Synchronise Specific Vehicle History with the Service Centre Management Information System and requests a Vehicle Service according to the next Due Service according to the Vehicle Manufacturer's Prescribed Service Program.
  ii. The Service Centre Management Information System will provide the Next Available Service Time according to the Time Prescribed for such a service.
  iii. The User will then be given the opportunity to Accept or Reject the Service Booking.
5.6.3 Service Centre Synchronisation creates the Synchronisation of Specific Vehicle eVLB Service Data with the Service Centre Management Information System (MIS) (75).
5.7 Synchronise the M/APP with Main System creates the Synchronisation of any Vehicle Specific eVLB data through HHP's and Main System. Once connected via standard Access Method, The System will confirm you are ready to Synchronise both Systems
  i. Once approved, System will Synchronise
  ii. System will alert when Synchronisation Complete
  iii. Disconnect HHP device
  iv. Disconnection Registered
5.8 Module Reporting:
  All Reports are Date/Time Logged
  System will report on—
  5.8.1 eVLB
    i. Specific Vehicle Fuel/Oil Purchases
    ii. Total Vehicles Fuel/Oil Purchases
    iii. Specific Vehicle Current Mileage
    iv. Total Vehicles Current Mileage
  5.8.2 Vehicle Scheduling Diary
    i. Specific Vehicle Scheduled Diary
    ii. Total Vehicles Scheduled Diary
  5.8.3 Travel Planner
    i. User Planned Travel
    ii. Specific Vehicle Planned Travel
  5.8.4 Service and Maintenance Costing
    i. Previous Specific Vehicle Costs based on Historical Specific Period
    ii. Previous Total Vehicle Costs based on Historical Specific Period
    iii. Projected Specific Vehicle Costs based on Projected Mileage by either—
      a. Historical Specific Period Mileage
      b. Present Vehicle Allocation
  5.8.5 User Fuel/Oil Purchases
  5.8.6 Specific Vehicle Maintenance/Service Costs
  5.8.7 User/Specific Vehicle Maintenance/Service Costs
6.0 Mobile Personal Healthcare (Personal Health Records) Module Overview:

The Healthcare Management Module is specifically designed to be an aid in assisting Users to achieve and maintain better overall Health management through better Healthcare Records from birth through to aged care.

This will include the various immunisation periods of early childhood and adolescent years; ongoing sporting injuries; seasonal infections; PBS medications; specific Healthcare Provider communications and record of exposure to various diagnostic and treatment technologies, whether or not chronic or long-term illness is a factor.

Because of the nature of Personal Health Records (PHR) and the general circumstances surrounding where they can sometimes be created, added to or just accessed by the User/Patient and/or by any number of Healthcare Providers and/or Government Institutions, the System records many of these within the Personal Diary format. This allows the User/Patient to more easily relate to their own records based around dates and also Healthcare Provider Appointments and Communications.

The System provides such Personal Health Records in a mobile and self controlled structure to also integrate directly to any government's ongoing eHealth systems and initiatives where required, applying any government's eHealth standards to the module.

Module Functionality—
6.1 User/Patient Log-in—User/Patient Most Be already Logged-in to the HHP device
  i. Module Log-in—User/Patient selects Personal Health Records (PHR) Icon—logs User/Patient into PHR from General User Access
  ii. User/Patient is then asked to Log-in with their PHR Validation Log-in (secondary) PHR Validation Code
    Although not recommended, this can be made unnecessary if preferred
  iii. User/Patient Personal Health Records (PHR) Access including Merging, Transfer and/or Synchronisation Rights
6.2 Symptoms Entry
  6.2.1 Manual Entry—Symptoms Experienced—Time/Date Stamped
    These will then be highlighted to the Healthcare Provider following Synchronisation with the Healthcare Provider PMS (79):
    i. Synchronisation of User/Patient PHR to the Healthcare Provider—Time/Date Stamped when:
      This functionality is subject to the level of system integration provided by each Healthcare Provider's PMS
        a. Prior to Consultation—User/Patient elects to send Electronic Package Transfer (Secured data) via internet
        b. Prior to Consultation—Synchronisation between User/Patient M/APP & Healthcare Provider PMS (79) at Healthcare Provider reception prior to consultation via BlueTooth (85) or USB (86) Interface
        c. During Consultation—Synchronisation between User/Patient M/APP & Healthcare Provider PMS (79) via BlueTooth (85) or USB (86) Interface
        All Synchs—Time and Date Stamped
    ii. Symptoms Logged—Can be entered and/or Changed by User/Patient and/or the Healthcare Provider
      This functionality is subject to the level of system integration provided by each Healthcare Provider's PMS
    ii. Undiagnosed Symptoms are each automatically allocated a Unique Identifying Code, which will then be permanently attached to each symptom and will ID them along with a Time/Date Stamp of when they were Logged and/or Re-logged (if re-occurring) with any notes also attached.
      1 As ensuing symptoms are experienced and Logged by User/Patient, providing each falls within a pre-defined period (Eg. 1 week), each will by default be associated to the previously Logged Symptom/s. Each association by default can be easily overridden.

2 When the user meets with the appropriate Healthcare Provider, the symptoms are identified and consequently acknowledged and dealt with intern.
3 When the Healthcare Provider makes their final Condition Diagnosis, these Logged and Associated Symptoms can be easily but formally attached to the Condition by the Healthcare Provider or in User/Patient in Consultation with the Healthcare Provider.
4 These will remain as a part of User/Patient PHR so that a Healthcare Provider may look for any outstanding symptoms during consultations and as a matter of PHR, they will remain as part of User/Patient Available PHR.
b. Diagnosed Symptoms can be each delegated (tentatively) to Existing Conditions at entry and automatically allocated a Unique identifying Code, which will then be permanently attached to each symptom and will ID them along with a Time/Date Stamp of when they were Logged and/or Re-logged (if re-occurring) with any notes also attached
These will remain as part of User/Patient Available PHR.
6.2.2 Healthcare Provider Entry—Synchronised—Symptoms Experienced—Time/Date Stamped via PMS Patient Records (PHR) Synch allows Healthcare Provider to either:
Manually Enter Symptoms Experienced by User/Patient during Consultation
or
Synchronise PMS Patient PHR with User/Patient PHR via User/Patient M/APP:
This functionality is subject to the level of system integration provided by each Healthcare Provider's PMS
User/Patient is then asked to confirm Merging, Transfer and/or Synchronisation with their PHR Validation Log-in (secondary) PHR Validation Code
a. Prior to Consultation—Electronic Package Transfer (Secured data) via internet
b. Prior to Consultation—Synchronisation between User/Patient M/APP & Healthcare Provider PMS (79) at Healthcare Provider reception prior to consultation via BlueTooth (85) or USB (86) Interface
c. During Consultation—Synchronisation between User/Patient M/APP & Healthcare Provider PMS (79) via BlueTooth (85) or USB (86) Interface
All Synchs—Time and Date Stamped
6.3 Contacts (PHR)—Manages the contact details, some communications and references to User/Patient Healthcare Providers
6.3.1 Contact Classification—means as any Contact is entered into the System, a Classification is required for various reasons within The System use
  i. Class 1 (C1)—HCP (HealthCare Provider)—is the Classification used for any Contact used by User/Patient as a Healthcare Provider
  ii. Class 1 (C1)—HCP (HealthCare Providers)—Contacts listed as Medical and HealthCare Providers to the Individual User can be Assigned/Referred to another User within the Household (Main) system though will only assign/refer basic Contact Details.
A Full Contact History and Associated Attachments will be retained only within the referring User's Contacts and Diary Records as they are retained as "Class 1—HCP" records.
  iii. Class 1 Contacts and any Activities pertaining to or associated with Class 1 Contacts will become and remain part of the User/Patient Personal Health Records (PHR)
  iv. If User has Dependant Child PHR File attached, (as referred to in 1.0/Main Sys/b)/ii)/a)/ii)), C1 Contacts are also Associated to that specific Dependant Child PHR File
Class 1 Contacts require a Provider Number that is obtained from the HealthCare Provider
6.3.2 Referred Contacts:
  a. Means a Referred Contact the User/Patient receives electronically as an MS Outlook Contact file—
    i. If actioned by User/patient, the System will import this Contact's Details as a Contact and request of User/Patient that Contact Class be confirmed as Class 1—HCP (if pre-set to do so) with a "Referred By" field that requires manual entry
    ii. Any Class 1—HCP Contact will always carry the "Referred By" field as a visible reference on the Contact Screen
  or
  b. Means a Referred Contact the User/Patient enters manually as a Contact and Classed as Class 1—HCP with the "Referred By" field also completed
    i. Any Class 1—HCP Contact will always carry the "Referred By" field as a visible reference on the Contact Screen
6.4 Appointment Manager (PHR)—Sets and Manages Appointments/Entries/Reminders with Healthcare Providers through The User/Patient Diary
6.4.1 User/Patient Appointments/Entries/Reminders Diary Entries:
  i. Parallel Entry—means each time an Appointments/Entries/Reminders is entered into the User/Patient Diary with a Class 1—HCP Contact, the entry (if pre-set to do so) will be simultaneously Parallel Entered (mirror entered) into other User/Patient Diaries and tagged according to which Diary
    a. Personal Diary—by default includes PHR Appointments/Entries/Reminders
NO PHR will be Merged, Transferred and/or Synchronised unless Target Diary System has HL7 Gateway (HL7g)
PHR Appointments/Entries/Reminders will show PHR Identification in Personal Diary
If PHR Appointments/Entries/Reminders are set from other Diaries (Business/Household), they will show only P Identification (Id) & Colour Coded (CC) in the Diary set from
    b. PHR Diary—can be set as a separate PHR Diary if required by User
Once a Child has a required Medicare number, a separate PHR Diary may be created and used within a Parent's Diary
This Child's PHR Diary is Automatically Synchronised between Parent PHR Diaries
    c. Household Diary—All Users Access
Each User has their Entries Colour Coded to the same Defaulted Colour—This Colour can be changed by the User
Business and Household Diaries can be set to have Personal (P) and Personal Health Records (PHR) Appointments/Entries/Reminders made from within and marked either P (CC) or PHR (CC). In these cases, they will automatically insert (as pre-set) with Default Tag Eg.—

P—"9:00 am P(CC)"—Available in Business and Household Diaries

PHR—"9:00 am PHR(CC)"—Available in Household Diary

PHR Diary Entries can be made by the User/Patient from a Class 1 Contact Screen; Personal Diary; PHR Diary; Household Diary or Business Diary providing they are available from within the HHP device ii. Single Entry—means each time an Appointments/Entries/Reminders is entered into User/Patient Diary with a Class 1—HCP Contact, the entry (if pre-set to do so) will not be simultaneously Parallel Entered (mirror) entered into other User/Patient Diaries 6.5 Entry of Personal Health Records (PHR)
  6.5.1 Manual Entry via User/Patient Personal Diary—At any time are entered via User/Patient M/APP by selecting PHR which are then tagged as PHR
    i. Included Details from the Chronic Condition Module/s Specific Integration Interface—Section 10.10 (if Pre-set in System Set-up)
  6.5.2 Entry of Personal Health Records (PHR)—Synchronise User/Patient M/APP with Health Provider PMS (79)
    This functionality is subject to the level of system integration provided by each Healthcare Provider's PMS
      a. Prior to Consultation—Electronic Package Transfer (Secured data) via internet
      b. Prior to Consultation—Synchronisation between User/Patient M/APP & Healthcare Provider PMS (79) at Healthcare Provider reception prior to consultation via BlueTooth (85) or USB (86) Interface
      c. During Consultation—Synchronisation between User/Patient M/APP & Healthcare Provider PMS (79) via BlueTooth (85) or USB (86) Interface
      All Synchs—Time and Date Stamped
  6.53 System Responses/Intervention Actions are set-up by User/Patient in consultation with the Providing GP and/or Specialist. Parameters are set to match the individual medical condition and User/Patient needs with some System Responses requiring Interaction Access including Notification/ALERT sends to Providing GP and/or Specialist and/or Other Nominated Party via Predetermined Prioritised System Method/s.
    Response available:
      i. User Response/No System Response—Time/Date Stamped
      ii. Send SMS Notification to Providing GP and/or Specialist of User Response—Time/Date Stamped
      iii. Send SMS ALERT to Providing GP and/or Specialist of User Response—Time/Date Stamped
      iv. Send SMS Notification to Other Nominated Party of User Response—Time/Date Stamped
      v. Send SMS ALERT to Other Nominated Party of User Response—Time/Date Stamped
      vi. Send Email Notification to Providing GP and/or Specialist of User Response—Time/Date Stamped
      vii. Trigger Further Follow-up System Responses 6.6 Documents Intake & Manager—Referrals/Prescriptions/Provider Assessments/Healthcare Plans/Case Plans/Discharge Details—Saved in Sub-directory folder
  6.6.1 Manual Save attached Documents
  6.6.2 Auto Intake attached Documents following Merging, Transfer and/or Synchronisation with HealthCare Provider PMS (79)

6.7 Prescription (PBS) Tracking
  6.7.1 Automated Synchronise/Medication and Dispensing Details through Pharmacy using Pharmacy Point of Sale System (78)
    This functionality is subject to M/APP use and the level of system integration provided by each Pharmacy Point of Sale System
      i. All Details of Prescribed Medications dispensed
        a. Prescribed—PBS/Drug ID (DID)/Time/Date Stamped
        b. Dispensed—PBS/DID/Time/Date Stamped
      ii. Medication Reminders set for the User/Patient through User/Patient Diary Alarms, of Medication Dispensing Times and Dosages
        a. Personal Dispensing—PBS/DID/Time/Date Stamped
  6.7.2 Manual Entry/Medication and Dispensing Details through entry of Medication and Dispensing Details Screen
    i. All Details of Prescribed Medications dispensed
      a. Prescribed—PBS/Drug ID (DID)/Time/Date Stamped
      b. Dispensed—PBS/DID/Time/Date Stamped
    ii. Medication Reminders set for the User/Patient through User/Patient Diary Alarms, of Medication Dispensing Times and Dosages
      a. Personal Dispensing—PBS/DID/Time/Date Stamped
  6.7.3 Web Portal (82) Institutional Synchronisation
    (Only anticipated if M/APP not in use and subject to Government tracking of Dispensed Pharmaceuticals as relevant.)
      i. All Details of Prescribed Medications dispensed
        a. Prescribed—PBS/Drug ID (DID)/Time/Date Stamped
        b. Dispensed—PBS/DID/Time/Date Stamped
      ii. Medication Reminders set for the User/Patient through User/Patient Diary Alarms, of Medication Dispensing Times and Dosages
        a. Personal Dispensing—PBS/DID/Time/Date Stamped 6.8 Prescription (PBS) Re-order Reminder provides the User/Patient with System Sequenced Reminders/Actions according to parameters set in consultation with Prescribing GP or Specialist—Triggered Manually by the User/Patient following—
  Re-order Reminder Actions:
    1 Alarm Reminder—No Interactions
    2 Alarm Reminder—Integrated Improvement Tracking: Tracks Changes in Symptoms and/or Overall Condition
  6.8.1 Alarm Reminder—No Interactions
    i. Following Synchronised Setting via Pharmacy Point of Sale System (78), The System will offer to remind User/Patient through User Diary Alarms of Re-order or Re-Prescribing Dates if further Medications are necessary according to Prescribing GP or Specialist advice This functionality is subject to M/APP use and the level of system integration provided by each Healthcare Provider's PMS Prescription Re-order Reminder—Actions Sequence
1. Reminder/No Reminder
2. Dispensed—PBS/Drug ID (DID)/Time/Date Stamped
3. Notice Required/Days If The System has been set for a PBS Re-order Reminder against this Prescribing Event, at required notice of completion of the Prescribed Medication Course, The System will according to Prescribing GP or Specialist advice, remind the User/Patient through User Diary Alarms of Re-order Dates if further Medications are necessary These Prescribing Re-order Reminders can also be set to be activated through Integrated Improvement Tracking Only if No Improvement of Symptoms or Overall Condition has been acknowledged through Improvement Tracking functionality of The System—Responses based on Prescribing GP or Specialist advice ii. Following Manual Setting, The System will offer to remind User/Patient through User Diary Alarms of Re-order or Re-Prescribing Dates if further Medications are necessary according to Prescribing GP or Specialist advice—
1. Reminder/No Reminder
2. Dispensed—PBS/Drug ID (DID)/Time/Date Stamped
3. Notice Required/Days If The System has been set for a PBS Re-order Reminder against this Prescribing Event, at the required notice of completion of Prescribed Medication Course, The System will according to Prescribing GP or Specialist advice, remind the User/Patient through User Diary Alarms of Re-order Dates if further Medications are necessary These Prescribing Re-order Reminders can also be set to be activated through Integrated Improvement Tracking Only if No Improvement of Symptoms or Overall Condition has been acknowledged through Improvement Tracking functionality of The System—Responses based on Prescribing GP or Specialist advice 6.9 Symptom Tracking—Tracking Changes in Symptoms and/or Overall Condition Using specific Symptom Related Questions and Answers, the System can be set to Record Answers and to also Suggest Prescription Re-order and if necessary, Notify HealthCare Provider of Specific Symptom Changes.

6.9.1 Set-up in Provider PMS (79) by Provider GP or Specialist during Consultation to trigger at—
1 Independent Set Times/Dates
2 Integrated to Prescription Re-order Reminders This functionality is subject to the level of system integration provided by each Healthcare Provider's PMS Triggers Symptoms Change Questions—asked of the User/Patient by The System
If The System has been set for Improvement Tracking
If Trigger Parameters and Question/s have been Pre-set 6.9.2 Set-up Manually by User/Patient during Consultation or following Provider GP or Specialist Consultation Triggers Symptoms Change Questions—asked of the User/Patient by The System
If The System has been set for Improvement Tracking
If Trigger Parameters and Question/s have been Pre-set 6.10 Exercise Management
All Functionality available on HHP device (60)
Exercise Management provides User/Patient the ability to develop or be invited to and to manage, Personal and/or Group Exercise Activities and/or Regimes.

6.10.1 Manually Planning using the Contacts and Diaries module (Sec. 1.4.1) allows the User to plan any Individual Exercise Activity and to also create Default Exercise Activities, which can then be selected from a drop-down list each with preset default factors applied.
i. Preferred Day/Time/Period 6.10.2 Receiving Invitation for an activity planned by another Contact/User will on acceptance, be is inserted into the User Diary module applying the preset default factors 6.10.3 Exercise Type can be set as a Planning preset default factor or otherwise left for Manual Entry 6.10.4 Exercise Intensity can be set as a Planning preset default factor of Exercise Type or otherwise left for Manual Entry 6.10.5 Physical Outcome is triggered for Response if Alarm is Set and can be set as a Planning preset default factor or otherwise left for Manual Entry.

6.10.6 Recovery Action/Time can be set as a Planning preset default factor of Exercise Type or otherwise left for Manual Entry 6.10.7 All Exercise Completed will become Exercise Diary Records and will remain part of User/Patient Available PHR—They can be minimised from Record View and if required, Made Viewable and Reportable In the case of the User/Patient using a Chronic Condition Module, Exercise Management and Chronic Condition integrated functionality will be used where required.

6.11 Dietary Management
Dietary Management integrates to the Recipe' Library; Exercise Management and Diaries to help User better manage Food Consumption and Dietary Requirements based on Pre-defined User Preferences.

Dietary Management integrates to functions within Household Ordering and Inventory Module—Recipe' Library (Sec. 7.3)

6.11.1 Target Weight provides User the opportunity to target a specific weight allowing the User to more easily maintain the target weight or work towards achieving the target weight 6.11.2 Personal Calorie Target—will allow User to set Personal Calorie Targets
This function can also be set from Household Ordering and Inventory Module—Recipe' Library (Sec. 7.3.4)

6.11.3 Calorie Counter—will allow User to—
i. Apply Personal Calorie Target
ii. Calculate Calorie Totals for Any Recipe' within a Personal or Household Recipe' Library or Portions of the same Recipe'
iii. Search for Recipes' within the Recipe' Library containing Portions of certain Calorie Totals
iv. Count the Calorie Totals of Recipe' Portions served to 6.11.4 Personal Calorie Counter—will allow User to Plan Recipe' Regime based on—
  i. Personal Calorie Target
  ii. Favoured Ingredients
  iii. Portion Pre-defined Nutrient Targets
6.11.5 Dietary Requirements—will allow User to Pre-define for Meal Planning and Food Consumption purposes.
  i. Excluded or Restricted by Portion—Foods and/or Food Types such as Carbohydrates; Proteins; Sugars; Fats—Saturated/Unsaturated
  ii. Favour by Portion Nutrient Rich Targets such as Carbohydrates and Proteins
6.11.6 Food and Recipe' Planner—will allow User to plan Meals as Activities based on Pre-defined Preferences such as Calorie Targets and Dietary Requirements into either—
  a. Personal Diary
  or
  b. Household Diary
6.12 Chronic Condition Module is for those Users/Patients who have a Chronic Illness/Condition such as Diabetes Assignment to a Carer where required
  6.12.1 Each module will be developed in partnership with either Chronic Condition Associations and/or Chronic Illness Specialists with functionality and parameters that are Condition Specific.
    i. Intake of Summary Case Plan
    ii. Intake of Multiple Assessments
    When installed, the module will have changed some interactions with certain functionality depending on the requirements and parameters necessary to be Illness Specific such as Prescription Re-order Reminder; Improvement Tracking; Wellbeing Status Requests and System Responses
    The Diabetes Module is well underway and likely to be the first Chronic Condition Module to be implemented due to Doug's personal health condition and understanding. The module will also include a section of Predictive Modelling to project User/Patient BSL
  6.12.2 Wellbeing Status Requests can be used both with M/APP and Main System if there are Individuals residing with Illnesses such as Diabetics, Asthmatics and alike that may at certain times require or benefit from System Responses/intervention Action/s
    These Status Requests and Interventions have Parameters also requiring set-up in consultation with Providing GP and/or Specialist and the User/Patient due to System Responses in some cases requiring interaction access with Providing GP and/or Specialist.
      i. Request Parameters—Medical Condition Dependant—Set-up by the User/Patient to define their own Parameters
      EG. For Diabetics—Logic Questions to be asked by The System to determine possible Low/High Blood Sugar—System Responses/Intervention Actions can be set-up as previously stated.
6.13 Personally Controlled Electronic Health Records (PCEHR) Web Portal (83) Synchronisation—This will be done via Pre-set Web Portal Icon configured to only call up and log onto the Pre-set PCEHR Web Portal.
User/Patient Log-in—User/Patient Must Be already Logged-In to the Main System
  6.13.1 Function Activation—User/Patient selects Web Portal Icon—logs User/Patient into PHR from Main System with their personal System Profile (User name) and Password
  6.13.2 User/Patient is then asked to confirm Merging, Transfer and/or Synchronisation with their PHR Validation Log-in (secondary) PHR Validation Code
    Although not recommended, this can be made unnecessary if preferred
  6.13.3 User/Patient PCEHR now available for Merging, Transfer and/or Synchronisation
6.14 Institutional Web Portal (84) Synchronisation—This will be done via Pre-set Web Portal Icon configured to only call up and log onto the Pre-set Institution Web Portals.
  This functionality is subject to the level of system integration provided by each Institution
  This Function can also be Triggered Only from inside the Personal Healthcare Module
  6.14.1 User/Patient Log-in—User/Patient Must Be already Logged-in to the Main System
  6.14.2 Function Activation—User/Patient selects Web Portal Icon—logs User/Patient into PHR from Main System with their personal System Profile (User name) and Password
  6.14.3 User/Patient is then asked to confirm Merging, Transfer and/or Synchronisation with their PHR Validation Log-in (secondary) PHR Validation Code
    Although not recommended, this can be made unnecessary if preferred
  6.14.4 De-Identified PHR Datashare (dIDPHR) (Proprietary Standard) is available for Merging, Transfer and/or Synchronisation with certain institutions. This function is only offered where the institution requesting PHR Datashare by Electronic Request, provides the dIDPHR Request. dIDPHR is activated by selecting the dIDPHR Tick Select option in System Pop-up following the Institution dIDPHR request.
  6.14.5 User/Patient Personal Health Records now available for Merging, Transfer and/or Synchronisation
6.15 Privacy Control is set to limit availability of PHR to User/Patient Healthcare Providers based on Individual User/Patient personal or legal requirements at discretion of Individual User/Patient
  Privacy Control must be Set per Healthcare Provider
  6.15.1 No Default Setting
    i. If User/Patient attempts to Merge, Transfer and/or Synchronise with a Healthcare Provider Practice Management System or an Institutional Management Information System prior to setting Privacy Control PHR Access Level for that Healthcare Provider or Institution, The System will Require User/Patient to set PHR Access Level before Merging, Transfer and/or Synchronisation
  6.15.2 Privacy Control Settings can be set from—
    i. Healthcare Providers Screen during Set-up—M/APP
    ii. Healthcare Provider's Screen prior to Consultation/s—M/APP
    iii. Reminder Screen Prior to Consultation/s—M/APP 6.16 Health Fund & Rebate Manager—via Main System only
  6.16.1 System Logs onto Health Fund Provider's Management System via Health Fund Provider's Web Portal (77)
    i. User/Patient Logs into Health Fund Provider's Web Portal using Account Number and Password
      a. Details Logged and delivered each subsequent Log-in
    ii. Request Statements
      a. Request Financial Year/To/Date Statement—All Transactions Logged into Main System
      b. Request Previous Financial Year—All Transactions Logged into Main System
    iii. Rebate Claims
      a. Synchronise Claimable Transactions—Rebates against Claimable Items
    iv. Value For Money Calculation
      a. Calculate Current Fees Paid vs Rebates Paid
    v. Health Fund Level of Coverage Calculation
      a. List Specific Features of Other Coverage Plans Available
      b. Calculate against—Indicate most appropriate Coverage Offered by Health Fund Provider
        1. Current YTD
        2. Last 2 Years
        3. Last 5 Years
    vi. Auto Logged into Main System
      1 Activation once Main System has logged-off Health Fund Provider's Web Portal (77)
      2 Rebates Made against Claimed Items Logged—Time/Date Stamped
6.17 Synchronise the M/APP; Main System or Health Provider's Practice Management System—Once connected via standard Access Method, The System will confirm you are ready to Synchronise both Systems
  If User/Patient is Logged-in to PHR within either the M/APP or Main System, the System will confirm, "Only PHR to be Synchronised"
  User/Patient is then asked to confirm Merging, Transfer and/or Synchronisation with their PHR Validation Log-in (secondary) PHR Validation Code
6.18 Module Reporting
  All Reports are Date/Time Logged
    These reports will be subject to discussions with Health Departments, Medical and other Allied Health associations to establish what will be considered to be relevant and worthwhile
7.0 Mobile Ordering & Inventory
Module Overview:
  The Ordering & Inventory Module is specifically designed to be an aid in assisting Users better manage their personal time, meal planning and the cost of groceries to achieve and maintain better overall household budget control.
  The module will also help in maintaining a wide selection of food groups and types including maintaining of overall Nutritional Values of foods held, adding to better health management outcomes for the household members. This will make the management of weight loss and health conditions that are partly reliant on food consumption such as Diabetes considerably easier to manage.
  For Scanning Barcodes of products, the Main System will interface with 3$^{rd}$ Party Barcode Scanning devices. In the situation where using the Module within a M/APP, the System will use the M/APP Scanning capacity where available.

Module Functionality—
7.1 User Log-in:
  User Log-in for General Module Access is automatic once module is selected after HHP device log-in.
  User Log-In provides—
    i. Records Access
    ii. User Recognition—Date/Time Logged
    iii. User & Inventory—Date/Time Logged
    iv. User & Ordering—Date/Time Logged
    v. Synchronisation to Main Household System—Date/Time Logged
7.2 Enter Inventory—
  a. Manually via Items Detail Screen if no Scanner Function available
    Enter Inventory Manually is activated by the User selecting "Enter Product", which then activates a pop-up "Item Details Screen" if no Scanner Function available
  b. Using Scanner if Scanner Function available
    Enter Inventory Using Scanner Function is activated by the User selecting "Enter Product", which then activates a pop-up if a Scanner Function is detected, "Scanner Found" after which the "Scan Product Screen" will appear stating, "Scan Product"
7.3 Recipes' Library—when selected by User provide
  7.3.1 New Recipe' Library—will allow User to create a New Library for—
    a. Personal—allows User to assign any Recipe' to—
      i Personal Recipe' Library
      ii Personal & Household Recipe' Libraries
    b. Household—means All Users within the Household System will have access to use—
      i. All Existing Recipes'
      ii. New Recipes' Created from Household Library are assigned by default to Household Library
  7.3.2 Existing Recipe' Library—will allow User to access all Recipes' within—
    a. Personal Recipe' Library
    b. Household Recipe' Library
  7.3.3 New Recipe' Create—will allow User to create New Recipes' including Cooking Instructions
  7.3.4 Personal Calorie Target—will allow Users to set Personal Calorie Targets
    This function can also be set from Healthcare Management Module—Dietary Management (Sec. 6.11.2)
  7.3.5 Calorie Counter—will allow User to—
    a. Apply Personal Calorie Target
    b. Calculate Calorie Totals for Any Recipe' within a Personal or Household Recipe' Library or Portions of the same Recipe'
    c. Search for Recipes' within the Recipe' Library containing Portions of certain Calorie Totals
    d. Count the Caloric Totals of Recipe' Portions served
  7.3.6 Personal Calorie Counter—will allow User to Plan Recipe' Regime based on—
    i. Personal Calorie Target
    ii. Favoured Ingredients
    iii. Portion Pre-defined Nutrient Targets
  7.3.7 Dietary Requirements—will allow User to Pre-define for Meal Planning and Food Consumption purposes.
    i. Excluded or Restricted by Portion—Foods and/or Food Types such as Carbohydrates; Proteins; Sugars; Fats—Saturated/Unsaturated
    ii. Favour by Portion Nutrient Rich Targets such as Carbohydrates and Proteins 7.3.8 Food and Recipe' Planner—will allow User to plan Meals as Activities based on Pre-defined Preferences such as Calorie Targets and Dietary Requirements into either—
  a. Personal Diary
  or
  b. Household Diary
7.3.9 Ingredient Check—will provide an Inventory Status on Recipe' Ingredients with option to Add Items to—
  a. Existing Shopping List
  or
  b. Created Shopping List
7.4 Shopping List Creator—when selected by User will create Shopping List made up from "Pre-set Minimum Inventory Hold"
7.5 Product Ordering will create the Shopping List and convert to—
  a. Print Shopping List—System will send a print request to the Local Printer
  b. Hold Order in Pending—System will Save Order in Pending File
  c. Place Web Order—System will log onto the Product Order fulfillment Web Portal (81) using Account Number and Password
7.6 Current & Projected Usage & Costing (Via PUP) will calculate—
  7.6.1 Current Usage & Costing
  7.6.2 Projected Usage & Costing over Nominated Period
7.7 Product Comparison Testing—will compare Stocked Food Items or Other Products by User Selection
  iii. The System will deliver by request various Product Comparisons
  Outcome Results will be Logged and Saved in Household Inventory
7.8 Synchronise M/APP with Main System—Once connected via standard Access Method, The System will confirm you are ready to Synchronise both Systems
  7.8.1 Once Approved, System will Synchronise
  7.8.2 System will Alert when Synchronisation Complete
  7.8.3 Disconnect HHP device
  7.8.3.1.1.1 Disconnection Registered
7.9 Module Reporting:
  All Reports are Date/Time Logged
  System will report on—
  7.9.1 Current Inventory
    i. Items Held
    ii. Value
  7.9.2 Restocking History
    i. Dates; Order Items & Values
  7.9.3 Previous Orders
    i. Dates; Order Items & Values

What is claimed is:

1. A residential management system, the residential management system comprising;
    a system management module in communication with at least one operational module;
    wherein the system management module is adapted to send, via a network, instruction data to the at least one operational module and is adapted to receive operational data from the at least one operational module;
    wherein the at least one operational module comprises a resource module in communication with the system management module;
    wherein the resource module generates consumption or historical data representing the usage of a resource within a predetermined time period, with the predetermined time period being based on the operational data received by the system management module from the resource module;
    wherein the at least one operational module further comprises a contact and diary module in communication with the system management module via the network and adapted to generate an alert if the usage of a resource exceeds a threshold, the contact and diary module logging a date and time stamp of the alert; and
    at least one computing device configured as a special-purpose machine on which the system management module, the at least one operational module, the resource module and the contact and diary module are implemented;
    wherein the system management module is in direct communication with a hand held device via at least one network, such that a date and time-stamped alert can be sent to an authenticated user of the system, and wherein the system management module does not issue the time-stamped alert to a user if the user is not authenticated by the system.

2. The system as claimed in claim 1, wherein the time-stamped alert prompts an intervention action from the user, a predetermined third person or the system.

3. The system as claimed in claim 1, wherein the at least one operational module is adapted to record usage data from at least one authenticated user.

4. The system as claimed in claim 1, wherein the at least one resource is at least one of the group of: a gas resource, an electricity resource, and a water resource.

5. The system as claimed in claim 1, wherein data can be stored by the system in a storage system as historical data and compared with current data by a user via a display device.

6. The system as claimed in claim 1, wherein the first module authenticates a user to allow for access control, and denies access to a user if a user is not authenticated.

7. The system as claimed in claim 1, wherein the at least one operational module further comprises a module selected from the group of: a household accounts module, a security management module, a telecommunications module, an Internet access management module, an intelligence for fun module, an electronic vehicle log book module, healthcare management module, and a household inventory and ordering module.

8. The system as claimed in claim 7, wherein the contact and diary module is adapted to record costs and actions associated with at least one planned activity or action of a user.

9. The system as claimed in claim 7, wherein the household inventory and ordering module is adapted for recording inventory data relating to at least one inventory of a household, in which inventory data is updated based on at least one of supply data and consumption data.

10. The system as claimed in claim 1, wherein the system further comprises a network interface such that the system can interact with at least one third party system or device.

11. The system as claimed in claim 1, wherein data generated by the system is at least one of date stamped and time stamped.

12. The system as claimed in claim 1, wherein the system further comprises a recipe library with direct interaction with a personal health records module, a household inventory and ordering module, and the contact and diary module to provide food planning for users.

13. The system as claimed in claim 1, wherein the system generates and outputs a report for display on a display device, the report being based on data generated by at least one module for at least one user profile.

14. The system as claimed in claim 1, wherein at least one module is adapted for multiple diaries per user with at the least of: personal health records, a business, a shared motor vehicle and a shared household diary.

15. The system as claimed in claim 1, wherein the system further comprises a network interface operably coupled to the Internet, for sending and receiving data, via the network interface, to a web service, wherein the web service comprises at least one of environmental, public weather forecasting, distance mapping, traffic conditions, public health department, health fund, product filament, internet, telecommunications, financial institution, residential security system and motor vehicle remote security system provider web services.

16. The system as claimed in claim 1, wherein the modules are adapted to communicate with each other either directly or via the network.

17. The system as claimed in claim 1, wherein the system is adapted to calculate at least one of an actual and a predicted carbon footprint for a residence and/or user based on the consumption data generated and sorted by the system.

18. The system as claimed in claim 1, wherein the system is adapted to back-up data onto a storage device, such that a user may transfer a user profile and associated data to another system.

19. The system as claimed in claim 1, wherein the system management module comprises a mobile application on a user device that communicates with the at least one operational module.

20. The system as claimed in claim 7, wherein the healthcare management module is adapted to use at least one of; HL7 Gateway data format, Point to Point Secure Messaging Standards, De-Identified PHR Datashare and International Standards.

* * * * *